US012753443B2

(12) United States Patent
Saper et al.

(10) Patent No.: US 12,753,443 B2
(45) Date of Patent: Oct. 6, 2026

(54) METHODS RELATING TO ANTI-IL-1 THERAPY AND ANTI-IL-6 THERAPY AND HYPERSENSITIVITY

(71) Applicants: The Board of Trustees of the Leland Stanford Junior University, Stanford, CA (US); The Regents of the University of California, San Francisco, CA (US)

(72) Inventors: Vivian E. Saper, Palo Alto, CA (US); Elizabeth D. Mellins, Palo Alto, CA (US); Jill Hollenbach, San Francisco, CA (US)

(73) Assignees: The Board of Trustees of the Leland Stanford Junior University, Stanford, CA (US); The Regents of the University of California, San Francisco, CA (US)

( * ) Notice: Subject to any disclaimer, the term of this patent is extended or adjusted under 35 U.S.C. 154(b) by 400 days.

(21) Appl. No.: 18/275,474

(22) PCT Filed: Feb. 11, 2022

(86) PCT No.: PCT/US2022/016167
§ 371 (c)(1),
(2) Date: Aug. 2, 2023

(87) PCT Pub. No.: WO2022/174067
PCT Pub. Date: Aug. 18, 2022

(65) Prior Publication Data

US 2024/0093299 A1 Mar. 21, 2024

Related U.S. Application Data

(60) Provisional application No. 63/148,554, filed on Feb. 11, 2021.

(51) Int. Cl.
*C12Q 1/68* (2018.01)
*C07H 21/04* (2006.01)
*C12Q 1/6883* (2018.01)

(52) U.S. Cl.
CPC ..... *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2005/0032062 A1* 2/2005 Chibout ............... C12Q 1/6883 435/6.16
2012/0121513 A1* 5/2012 Frank ................. G01N 33/5011 424/9.2

OTHER PUBLICATIONS

Hollenbach et al. (MedRxiv preprint doi.org/10.1101/2020/08.10.20172338, Jan. 17, 2021—see IDS). (Year: 2021).*
Louthrenoo et al. (International J. of Immunogenetics, vol. 40, No. 2, pp. 126-120, Apr. 2013). (Year: 2013).*
Sugimori et al. (Experimental Hematology, vol. 35, pp. 13-20, 2007). (Year: 2007).*
Bharadwaj M, Illing P, Theodossis A, et al. Drug hypersensitivity and human leukocyte antigens of the major histocompatibility complex. Annu Rev Pharmacol Toxicol 2012;52:401-31.
Duong TA, Valeyrie-Allanore L, Wolkenstein P, et al. Severe cutaneous adverse reactions to drugs. Lancet 2017;390 (10106):1996-2011.
Yang CW, Cho YT, Hsieh YC, et al. The interferon-γ-induced protein 10/CXCR3 axis is associated with human herpesvirus-6 reactivation and the development of sequelae in drug reaction with eosinophilla and systemic symptoms. Br J Dermatol 2020;183(5):909-919.
Kim GY, Anderson KR, Davis DMR, et al. Drug reaction with eosinophilia and systemic symptoms (DRESS) in the pediatric population: A systematic review of the literature. J Am Acad Dermatol 2020.
Usui T, Naisbitt DJ. Human leukocyte antigen and idiosyncratic adverse drug reactions. Drug Metab Pharmacokinet 2017;32(1):21-30.
Mellins ED, Macaubas C, Grom AA. Pathogenesis of systemic juvenile idiopathic arthritis: some answers, more questions. Nat Rev Rheumatol. 2011;7(7):416-26.
Saper VE, Chen G, Deutsch GH, et al. Emergent high fatality lung disease in systemic juvenile arthritis. Ann Rheum Dis 2019;78(12):1722-31.
Efthimiou P, Kontzias A, Hur P. Rodha K, Ramakrishna GS, Nakasato P. Adult-onset Still's disease in focus: Clinical manifestations, diagnosis, treatment, and unmet needs in the era of targeted therapies. Seminars in Arthritis and Rheumatism. 2021;51(4):858-74.
Pardeo M, Rossi MN, Pires Marafon D, Sacco E, Bracaglia C, Passarelli C, et al. Early Treatment and IL1RN Single-Nucleotide Polymorphisms Affect Response to Anakinra in Systemic Juvenile Idiopathic Arthritis. Arthritis Rheumatol. 2021;73(6):1053-61.
Kaneko Y, Takeuchi T. Interleukin-6 inhibition: a therapeutic strategy for the management of adult-onset Still's disease. Expert Opinion on Biological Therapy. 2021:in press.
Ombrello MJ, Remmers EF, Tachmazidou I, et al. HLA-DRB1*11 and variants of the MHC class II locus are strong risk factors for systemic juvenile idiopathic arthritis. Proc Natl Acad Sci U S A 2015;112(52):15970-5.
Kardaun SH, Sekula P, Valeyrie-Allanore L, et al. Drug reaction with eosinophilla and systemic symptoms (DRESS): an original multisystem adverse drug reaction. Results from the prospective RegiSCAR study. Br J Dermatol 2013;169(5):1071-80.
Yang JJ, Lei DK, Ravi V, et al. Overlap between hemophagocytic lymphohistiocytosis and drug reaction and eosinophilia with systemic symptoms: a review. Int J Dermatol 2020.

(Continued)

*Primary Examiner* — Jeanine A Goldberg
(74) *Attorney, Agent, or Firm* — KDW Firm PLLC

(57) ABSTRACT

Provided herein are, inter alia, methods for treating subjects in need of an IL-1 inhibitor therapy or an IL-6 inhibitor therapy, and related methods. The methods include determining whether the subject is at risk for drug-related hypersensitivity by assaying for the presence of certain HLA alleles.

9 Claims, 14 Drawing Sheets

(56) References Cited

OTHER PUBLICATIONS

Wang J, Jelcic I, Mühlenbruch L, et al. HLA-DR15 Molecules Jointly Shape an Autoreactive T Cell Repertoire in Multiple Sclerosis. Cell 2020;183(5):1264-81.
Matzaraki V, Kumar V, Wijmenga C, et al. The MHC locus and genetic susceptibility to autoimmune and infectious diseases. Genomne Biol 2017;18(1):76.
Hetherington S, Hughes AR, Mosteller M, et al. Genetic variations in HLA-B region and hypersensitivity reactions to abacavir. Lancet 2002;359(9312):1121-2.
Barbaud A, Waton J, Herbeth B, et al. Comparison of cytokine gene polymorphism in drug-induced maculopapular eruption, urticaria and drug reaction with eosinophilia and systemic symptoms (DRESS). J Eur Acad Dermatol Venereol 2014;28(4):491-9.
Creary LE, Mallempati KC, Gangavarapu S, Caillier SJ, Oksenberg JR, Fernández-Viña MA. Deconstruction of HLA-DRB1*04:01:01 and HLA-DRB1*15:01:01 class II haplotypes using next-generation sequencing in European-Americans with multiple sclerosis. Mult Scler 2019;25(6):772-782.
Saper VE, Chen G, Khatri P, Mellins ED. Response to: 'Effectiveness and safety of ruxolitinib for the treatment of refractory systemic idiopathic juvenile arthritis like associated with interstitial lung disease: case report' by Bader-Meunier. Ann Rheum Dis 2020.
Altshuler DM, Gibbs RA, Peltonen L, et al. Integrating common and rare genetic variation in diverse human populations. Nature 2010;467(7311):52-8.
Hollenbach et al., "IL-1 and IL-6 inhibitor hypersensitivity link to common HLA-DRB1*15 alleles" Posted Jan. 17, 2021. medRxiv 2020.08.10.20172338; doi: https://doi.org/10.1101/2020.08.10.20172338.
Louthrenoo et al., "The genetic contribution of HLA-DRB5*01:01 to systemic lupus erythematosus in Thailand" International Journal of Immunogenetics, 2013, 40, 126-130.
Quartuccio et al., "Higher levels of IL!6 early after tocilizumab distinguish survivors from nonsurvivors in COVID-19 pneumonia: A possible indication for deeper targeting of IL!6" J Med Virol. 2020;92:2852-2856.
Saper et al., "Effect of Drug Withdrawal on Interleukin-1 or Interleukin-6 Inhibitor Associated Diffuse Lung Disease" [abstract]. Arthritis Rheumatol. 2021; 73 (suppl 10). https://acrabstracts.org/abstract/effect-of-drug-withdrawal-on-interleukin-1-or-interleukin-6-inhibitor-associateddiffuse-lung-disease/. Accessed Sep. 17, 2021.
Saper et al., "Characteristics of hla linked dress reactions to inhibitors of IL-1 and IL-6 in still's disease" Pediatric Rheumatology 2022, 20(Suppl 1):2.
Saper et al., "MAS and lung disease as complications of HLA-linked severe delayed reactions to inhibitors of IL-1 and IL-6 in still's disease".
Saper VE, et al. "Severe delayed hypersensitivity reactions to IL-1 and IL-6 inhibitors link to common HLA-DRB1* 15 alleles" Ann Rheum Dis 2021;0:1-10. doi:10.1136/annrheumdis-2021-220578.
Ter Haar, Nienke M et al. "Treatment to Target Using Recombinant Interleukin-1 Receptor Antagonist as First-Line Monotherapy in New-Onset Systemic Juvenile Idiopathic Arthritis: Results From a Five-Year Follow-Up Study." Arthritis & rheumatology (Hoboken, N.J.) vol. 71,7 (2019): 1163-1173.
Sousa-Pinto, Bernardo et al. "HLA and Delayed Drug-Induced Hypersensitivity." International archives of allergy and immunology vol. 170,3 (2016): 163-79.
International Search Report and Written Opinion for the International Application No. PCT/US22/16167, mailed Jun. 16, 2022, 8 pages.

* cited by examiner

FIG. 4

| 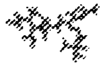 | 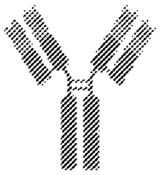 | 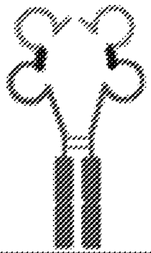 | 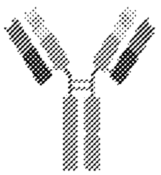 |
|---|---|---|---|
| Anakinra<br>Non-glycosylated form of human IL-1 receptor antagonist (IL-1RA) | Canakinumab<br>Human IgG1 monoclonal antibody, targeted to human IL-1β | Rilonacept<br>Dimeric glycosylated extracellular domains of IL-1 receptor 1 (IL-1R1, orange) and IL-1 receptor accessory protein (IL-1RAcP, green), fused to human IgG1 Fc region | Tocilizumab<br>Humanized IgG1 monoclonal antibody, targeted to soluble and membrane-bound IL-6 receptor 1 (IL-6R1) |

| Clinical finding during inhibitor treatment | Still's-DRESS | Still's controls | *P* value | OR (95% CI) |
|---|---|---|---|---|
| Peripheral eosinophilia | 57/64 (89%)[1] | 1/65 (2%) | $1.6 \times 10^{-27}$ | 521 (62-4366) |
| AST-ALT elevation | 49/65 (75%)[1] | 4/65 (6%) | $8.6 \times 10^{-17}$ | 47 (15-149) |
| Macrophage activation syndrome (MAS) | 42/66 (64%) | 2/65 (3%) | $1.2 \times 10^{-14}$ | 55 (12-246) |

| HLA allele | Ancestry | Still's-DRESS cases | Still's controls |
|---|---|---|---|
| HLA-DRB1*15:01 | Self-identified White, Hispanic, Asian/South Asian, or Black | 41/55 (75%) | 0/30 (0%) |
| HLA-DRB1*15:XX | | 45/55 (82%) | 2/30 (7%) |

METHODS RELATING TO ANTI-IL-1 THERAPY AND ANTI-IL-6 THERAPY AND HYPERSENSITIVITY

CROSS REFERENCE TO RELATED APPLICATIONS

This application is a national stage application, filed under 35 U.S.C. § 371, of International Application No. PCT/US2022/016167, entitled "METHODS RELATING TO ANTI-IL-1 THERAPY AND ANTI-IL-6 THERAPY AND HYPERSENSITIVITY," filed Feb. 11, 2022, which claims the benefit of priority under 35 U.S.C. § 119 (e) to U.S. Provisional Application No. 63/148,554 filed Feb. 11, 2021, each of which is incorporated herein by reference in its entirety.

BACKGROUND

Drug-related, delayed hypersensitivity reactions (DHR) were recently observed in association with various therapeutics that are otherwise efficacious for treating a variety of inflammatory conditions. The observed DHR were sometimes associated with a high fatality lung condition, diffuse lung disease (DLD). These findings were detected in patients with a particular type of juvenile arthritis, systemic juvenile idiopathic arthritis (sJIA) and its adult counterpart, adult-onset Still's disease (AOSD), collectively known as Still's disease. sJIA is defined as Still's onset before the 16$^{th}$ birthday and accounts for approximately 90% of Still's cases. sJIA with DHR, with or without DLD, is associated with particular human leukocyte antigen (HLA) class II alleles. Various HLA alleles have been associated with adverse drug-related reactions, including various forms of DHR.

Methods for identifying patients at increased risk of drug-related hypersensitivity reactions are needed to provide for safe and effective administration of therapeutics associated with such reactions in the treatment of inflammatory conditions. Disclosed herein, inter alia, are solutions to these and other problems in the art.

SUMMARY OF THE INVENTION

The present invention is based, in part, on the discovery of a genetic risk factor for severe delayed hypersensitivity reactions associated with anti-IL-1 and anti-IL-6 therapy. Accordingly, the invention provides methods of treating a subject receiving, or in need of, an anti-IL-1 or an anti-IL-6 therapy, the method comprising detecting a human leukocyte antigen (HLA)-DRB1*15 allele or HLA-DRB5*01:01 allele, or a genetically linked surrogate thereof, in a biological sample of the subject; and for the subject receiving an anti-IL-1 or an anti-IL-6 therapy, performing an action selected from (i) discontinuing the anti-IL-1 or anti-IL-6 therapy, (ii) administering an altered dose of the anti-IL-1 or anti-IL-6 therapy; or (iii) administering the anti-IL-1 or an anti-IL-6 therapy in combination with an additional therapy; or for the subject in need of an anti-IL-1 or an anti-IL-6 therapy, administering an alternative therapy to the subject.

The invention also provides methods of identifying a subject at risk of an anti-IL-1 or an anti-IL-6 therapy related hypersensitivity reaction, the method comprising detecting an HLA-DRB1*15 allele or HLA-DRB5*01:01 allele, or a genetically linked surrogate thereof, in a biological sample of a subject receiving, or in need of, an anti-IL-1 or an anti-IL-6 therapy, wherein the presence of an HLA-DRB1*15 allele, or genetically linked surrogate thereof, indicates the subject is at risk of a therapy related hypersensitivity reaction.

The invention also provides methods of analyzing a biological sample of a subject receiving, or in need of, an anti-IL-1 or an anti-IL-6 therapy, the method comprising detecting an HLA-DRB1*15 allele or HLA-DRB5*01:01 allele, or a genetically linked surrogate thereof, in the biological sample.

The invention also provides methods for preparing a deoxyribonucleic acid (DNA) fraction useful for genotyping from a subject receiving, or in need of, an anti-IL-1 or an anti-IL-6 therapy, the method comprising (a) extracting DNA from a biological sample of the subject; (b) producing a fraction of the DNA extracted in (a) thereby producing a DNA fraction; (c) determining whether the DNA fraction comprises an HLA-DRB1*15 allele or HLA-DRB5*01:01 allele.

In embodiments of the methods described here, the HLA-DRB1*15 allele is an HLA-DRB1*15:01 allele, HLA-DRB1*15:03 allele or an HLA-DRB1*15:06 allele. In embodiments, the HLA-DRB5*01:01 allele is detected.

In embodiments, the anti-IL-1 or anti-IL-6 therapy is anakinra, canakinumab, rilonacept, tocilizumab, sarilumab, or satralizumab therapy.

In embodiments the administering an altered dose of the anti-IL-1 or anti-IL-6 therapy comprises decreasing the dose or decreasing the frequency of administration, optionally wherein the decreased dose is 20% to 80% of the originally administered dose or the decreased frequency of administration is half the original frequency administered.

In embodiments, the administering an anti-IL-1 or anti-IL-6 therapy in combination with an additional therapy comprises one or more additional therapies selected from methotrexate therapy, corticosteriod therapy, and a disease-modifying antirheumatic drug (DMARD) therapy.

In embodiments, the alternative therapy comprises one or more therapies selected from intravenous gamma globulin (IVIG), a calcineurin inhibitor, a Janus kinase (JAK) inhibitor, a TNF inhibitor, a corticosteroid, a T-cell inhibitor, and an IL-5 inhibitor therapy. In embodiments, the calcineurin inhibitor is cyclosporine or tacrolimus. In embodiments, the Janus kinase inhibitor is tofacitinib, baricitinib, ruxolitinib, or upadacitinib. In embodiments, the TNF inhibitor is adalimumab. In embodiments, the T-cell inhibitor is abatacept.

In embodiments, the subject in need of an anti-IL-1 or anti-IL-6 therapy is a subject having an inflammatory disease. In embodiments, the inflammatory disease is selected from systemic juvenile idiopathic arthritis (sJIA), adult onset Still's disease (AOSD) or Kawasaki disease (KD). In embodiments, the inflammatory disease is selected from polyarthritis, rheumatoid arthritis, undifferentiated autoinflammatory disorder, giant cell arteritis, and COVID-19 related cytokine storm.

BRIEF DESCRIPTION OF THE FIGURES

FIG. 1A Variant pulmonary alveolar proteinosis/endogenous lipoid pneumonia has alveolar filling by proteinaceous material with cholesterol clefts. Arteries (a) with wall thickening are frequent. FIG. 1B Higher power of lung biopsy demonstrating scattered eosinophils (arrows) and cholesterol clefts (arrowhead). Increased eosinophils are consistent with DHR and also seen in various inflammatory diseases including rheumatologic conditions. FIG. 1C Example of a non-evanescent serpiginous pruritic rash with hyperpigmented borders, atypical for sJIA, in a case of sJIA-DHR/DLD during tocilizumab therapy. FIG. 1D Pruritic erythematous non-evanescent edematous rash over knees observed in sJIA-DHR/DLD during rilonacept treatment. FIG. 1E. Skin biopsy in sJIA-DHR with vacuolar interface dermatitis and eosinophils. As stated in Larson et al, the predominance of eosinophils favors an alternative diagnosis of an interface drug eruption including DHR. FIG. 1F Higher power images showing lymphocytes, vacuolation at the dermal-epidermal junction and focal dyskeratotic keratinocytes (asterix) (b) as well as numerous perivascular eosinophils (arrows) (c) FIG. 1G Similar pruritic erythematous non-evanescent edematous rash in sJIA-DHR without DLD during anakinra (biopsy shown in (FIGS. 1E-1F)) and FIG. 1H in KD-sAR during anakinra.

FIG. 2A shows sample accounting through the principal component analysis. FIG. 2B Principal components (PCs) were calculated using a linkage disequilibrium reduced set of intersecting SNPs between sJIA-DHR subjects, INCHARGE sJIA cases and controls, and subjects from the HapMap3 populations (grey boxes). PCs were plotted to identify subjects of European continental ancestry, marked by the black box, which were carried forward into round 2. FIG. 2C The second round of PCs were calculated for this reduced set of subjects and were plotted to exclude additional ancestrally dissimilar subjects. FIG. 2D The third round of PCs were calculated for the subset of subjects defined by round 2, and round 3 PCs were plotted to examine the structure of the final study population. Genomic control inflation factors were calculated for sJIA-DHR vs. sJIA GWAS (λGC=1.042) and sJIA-DHR vs. GWAS controls (λGC=1.056).

FIGS. 3A-3D HLA-DRB1*15 alleles: sequences, peptide-binding motifs and relevant structural detail. FIG. 3A Full length protein sequence alignment of HLA-DRB1*15 alleles. Full length protein sequence alignment according to IPDIMGT/HLA Release 3.41.0 (2020-07-13) is shown. The hyphen symbols represent positions where the amino acid (aa) residue is identical between the HLA-DRB1*15:01 sequence and the other HLA-DRB1*15 alleles shown. The single aa substitutions that distinguish each allele are indicated. Asterisk symbols in HLA-DRB1*15:06 protein indicate segments of sequence that have not been characterized yet. FIG. 3B Peptide binding motifs for the DRB1*15 alleles, indicating similarity between DRB1*15:01, 15:03 and 15:06, but not 15:02. The motifs were obtained using NetMHCIIpan 4.0 MOTIF VIEWER, which provides data visualization using Seq2Logo. Large-scale, eluted MHC II ligand mass spectrometry data sets used to develop the server were obtained from the Immune Epitope Database and analyzed using the NNAlign_MA machine learning framework. On the y-axis are shown the amino acid residues (in standard letter code) enriched (positive values) or depleted (negative values) at each position along the bound peptide, in order of predominance. The height of the letter reflects the relative enrichment. The amino acids are hydrophobic (black); polar; basic; acidic. The numbered positions along the X axis refer to residues along the bound peptide. Residues at positions 1, 4, 6, 9 are motif position residues whose side chains bind into pockets (e.g. P1 pocket) within the MHC class II molecule peptide-binding groove. Peptide oriented with the N-terminus to the left. FIG. 3C Structural details related to variations between DRB1*15:01, 15:03, 15:06 and 15:02. The figure shows part of the membrane-distal domain structure of HLA-DR 15:01 in complex with type IV collagen aa135-145 (GWISLWKGFSF). Data are from PDB ID 5V4M, and visualized by PyMol. HLA-DRa is removed for better visualization of bound peptide and amino acid side chains at allelically variant positions [aa 30, 50, 86 of DR beta, as indicated and in (FIG. 3A)]. The peptide is presented in full atomic detail. The peptide interacts with the binding groove mainly through 4 (bolded) residues, GWISLWKGFSF, at motif positions P1, P4, P6, P9. The N-terminus of the peptide is at the right in the figure. The surface contours of the peptide binding groove are indicated by the dashed line. Position DR beta 30 (β30) [tyrosine (shown) or histidine] is in the floor of the groove and mediates a hydrogen bond (black dotted line) with the peptide main chain between the P6 and P7 pockets. Position DR beta 50 (β50) [valine (shown) or alanine] is outside the groove. Neither of these residues influence peptide-binding in a sequence-specific manner. Position DR beta 86 (β86), however, which differs between DRB1*15:02 (glycine) and the other DRB1*15 alleles (valine), significantly changes the size of the P1 pocket, increasing its size in β86Gly containing alleles to accommodate larger side chains at P1 and thus influencing peptide binding motifs (above).

FIG. 4 Different chemical structures of cytokine blockers implicated in HLA-DRB1*15 associated DHR. Shown are diagrams of the structures of IL-1 inhibitors (anakinra, canakinumab, rilonacept) and an IL-6 inhibitor (tocilizumab), as described in references respectively. The diagrams reflect the relative sizes of the molecules, with the anakinra structure shown at 3× magnification to be visible. Anakinra blocks the biologic activity of IL-1α and IL-1 beta by competitive inhibition of binding to IL-1R1. Rilonacept acts as a decoy receptor ("trap") for IL-1 beta and, with lesser affinity, binds endogenous IL-1RA and IL-1α. Canakinumab binds IL-1 beta only, and tocilizumab inhibits IL-6 activity by blocking its binding to IL-6R1.

Similar numbers of Still's-DRESS (n=65+1 suspected delayed anakinra reaction Still's; see methods) and Still's controls (n=65) subjects were enrolled for case/control comparison and do not reflect the incidence of inhibitor-triggered DRESS in Still's disease. HLA genotyping was performed on the subset of patients with available sample or sequence data. All 19 Kawasaki disease subjects were enrolled in a Phase I/IIa clinical trial of anakinra in KD patients with coronary artery abnormalities (FIG. 6B) and were clinically scored as suspected anakinra reaction or drug-tolerant; all were HLA typed. Details of scoring and HLA genotyping are provided in methods and supplementary information. Still's Disease: sJIA, systemic onset juvenile idiopathic arthritis (Still's onset <16 yrs) and AOSD, adult-onset Still's Disease (Still's onset ≥16 yrs). RegiSCAR, a scoring system developed by a registry of experts assembled to clinically classify drug induced severe cutaneous reactions; DRESS, drug reaction with eosinophilia and systemic symptoms.

Figure 7:
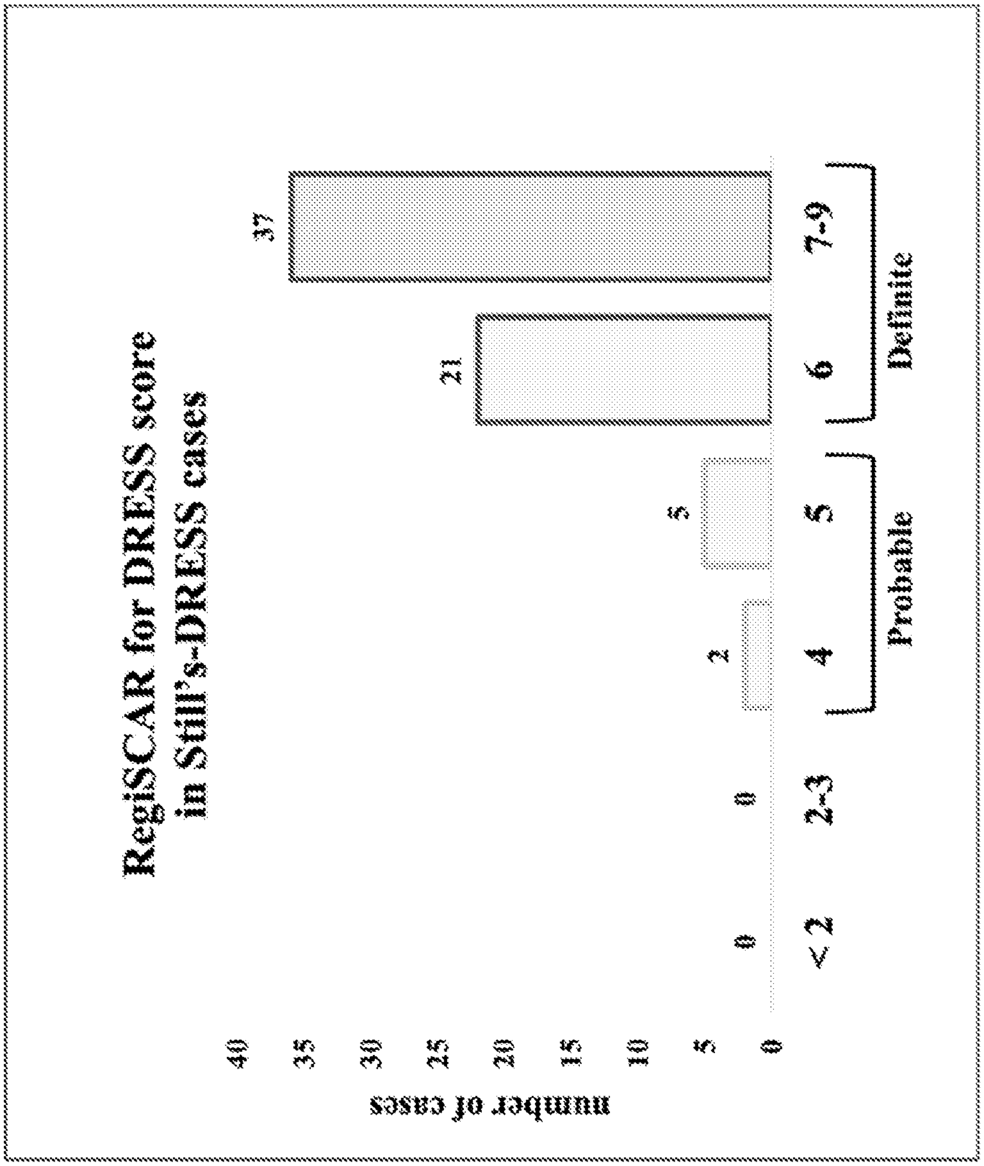

FIG. 7 is a bar graph depicting the RegiSCAR for DRESS scores in Still's-DRESS cases. Numbers of Still's-DRESS cases with RegiSCAR for DRESS scores of definite or probable are shown (n=65) in the graph. The Still's case with suspected delayed anakinra reaction is not included. RegiSCAR classifies a case as definite (6-9), probable (4-5), possible (2-3) or no case (0 to negative 4). For DRESS cases reacting to more than one IL-1/IL-6 inhibitor, the highest RegiSCAR value is shown. By definition, no drug-tolerant subject scored ≥4. RegiSCAR scoring elements are shown in supplementary information.

Figure 8:
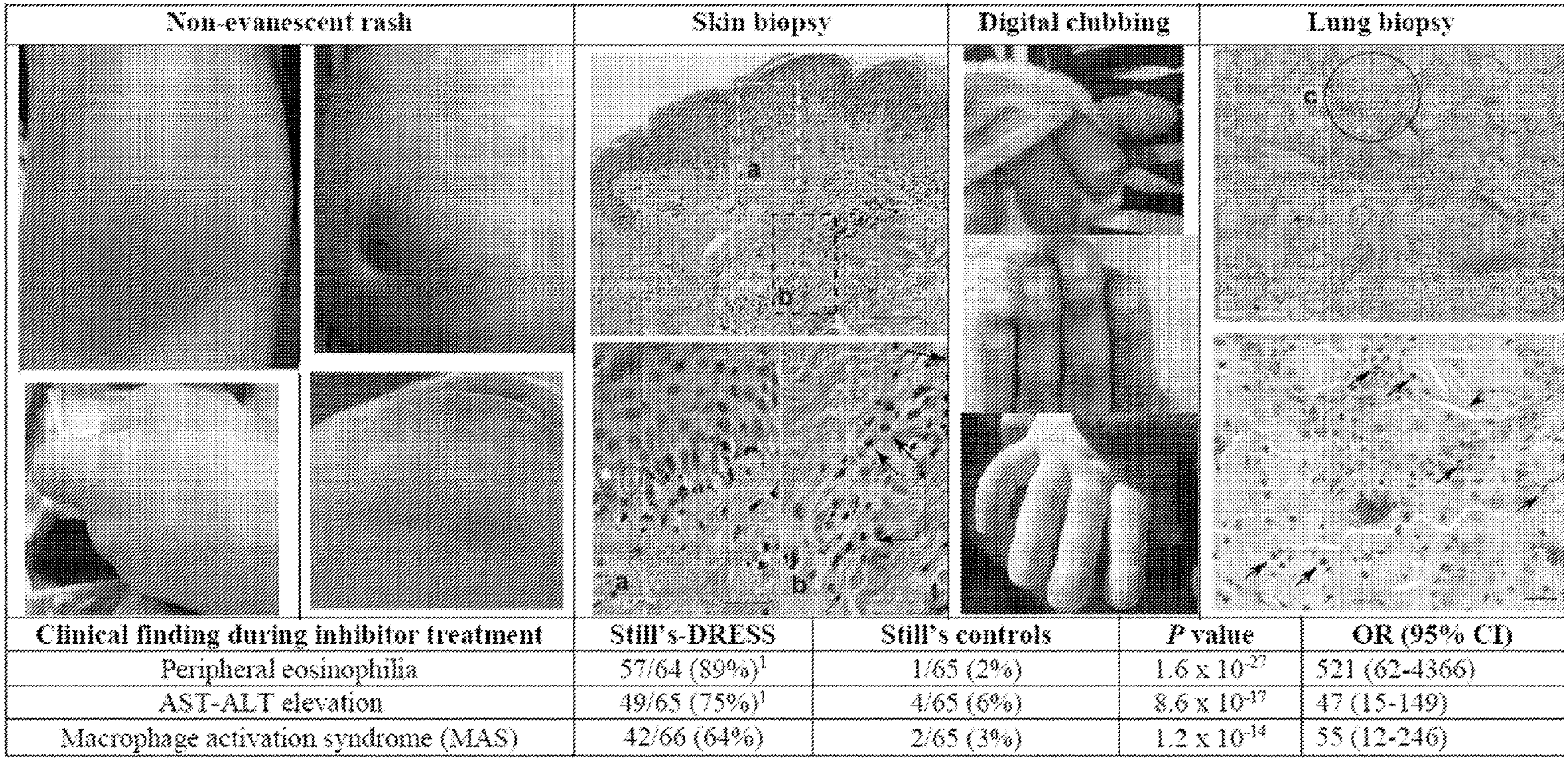

FIG. 8 are a series of images depicting unusual clinical features in inhibitor-treated Still's patients. Images of non-evanescent rash, typically pruritic, are shown. Upper left: On anakinra, erythema and prominent edema affecting knee; upper right: on tocilizumab, excoriated and areas of hyperpigmentation on abdomen; lower left: On canakinumab, erythematous, edematous rash on hand [similar rash on face and ear is not shown]; lower right: On anakinra, erythema, edema and non-herpetic vesiculation on face. Skin biopsy of drug-associated rash shows vacuolar interface dermatitis and eosinophils. Higher power images (sections a, b) show lymphocytes, vacuolation at the dermal-epidermal junction, focal dyskeratotic keratinocytes (asterisk) and perivascular eosinophils (arrows). Acute digital clubbing, often erythematous, was frequently the first indication of lung involvement in patients with DRESS and diffuse lung disease. Images of acute clubbing on tocilizumab (top), anakinra (middle), on canakinumab (bottom). Lung biopsy showing variant pulmonary alveolar proteinosis/endogenous lipoid pneumonia and arterial wall thickening (c). Higher power image (below) shows cholesterol clefts (arrowhead) and scattered eosinophils (arrows). 8/16 reviewed cases showed eosinophils in many fields (see supplementary methods). Increased lung eosinophils are consistent with DRESS and also seen in various inflammatory diseases. Table: In DRESS cases, median (interquartile range) of peak absolute eosinophil count was 1500/μl (980,3080) and peak eosinophil % of WBC was 18% (12,33). AST-ALT elevation was defined as aspartate aminotransferase (AST) or alanine aminotransferase (ALT) measuring >2× the upper limit of normal more than once, without alternative (e.g., non-drug) explanation. The frequency of DRESS reactions did not differ significantly when combined IL-1 inhibitors were compared to the IL-6 inhibitor (tocilizumab) or when each inhibitor was analyzed separately. Analyses of specific clinical findings yielded similar results when AOSD patients were omitted. DRESS, drug reaction with eosinophilia and systemic symptoms; MAS, macrophage activation syndrome, a form of secondary hemophagocytic lymphohistiocytosis. P value, by Fisher's exact; OR (95% CI), odds ratio (95% confidence interval) Eosinophil information was unavailable in 2 cases (n=64); AST-ALT values were unavailable in 1 case, (n=65).

Figure 9A:
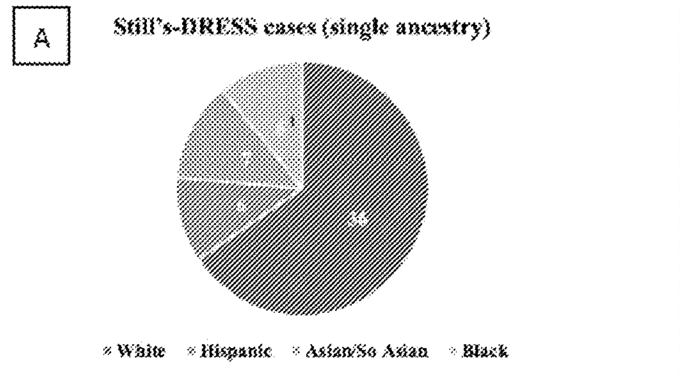
Figure 9B:
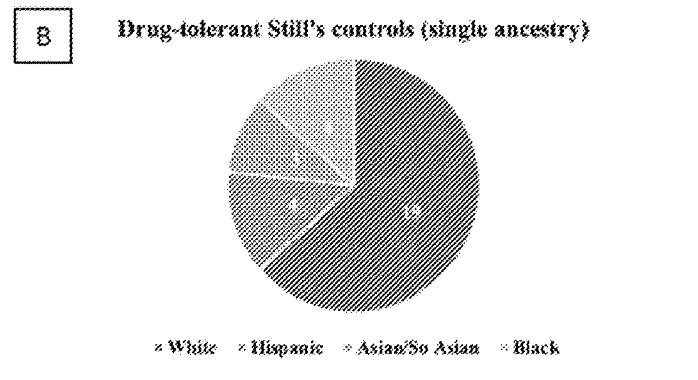
Figure 9C:
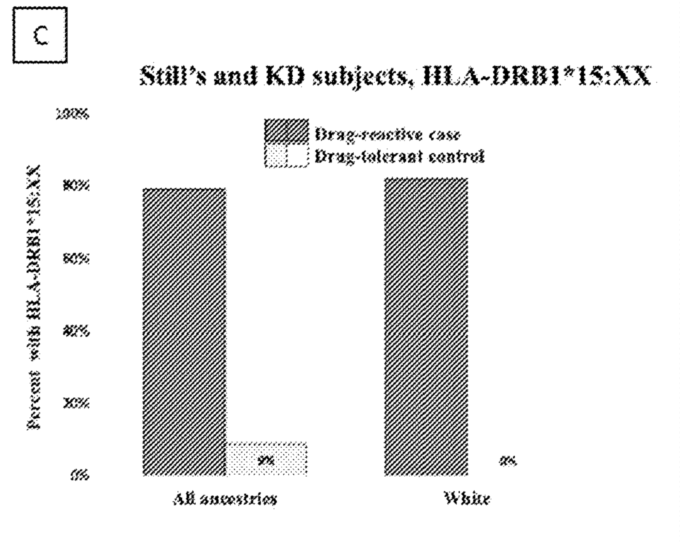
Figure 9D:
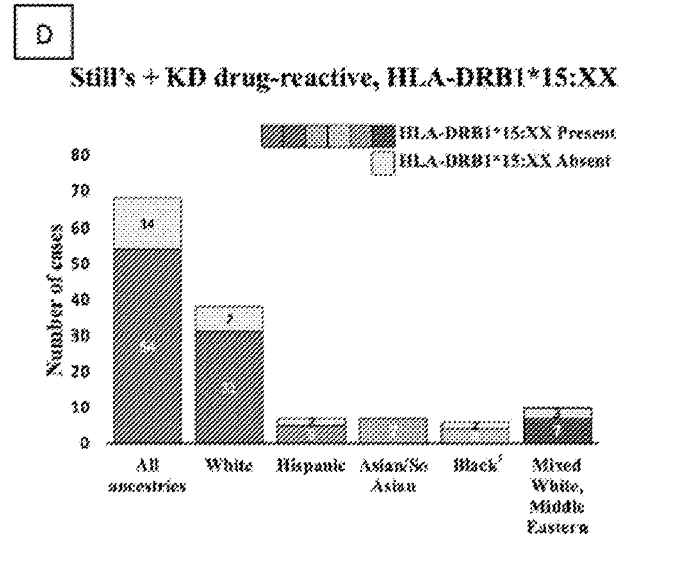

FIGS. 9A-9D are data showing that HLA-DRB1*15:XX appeared to be enriched in drug related delayed reactions across ancestries. The table shows carrier frequencies of HLA-DRB1*15:01 and HLA-DRB1*15:XX in Still's-DRESS cases and Still's controls. To compare groups with balanced ancestry, 9 Still's-DRESS cases were excluded from this analysis (leaving n=55), as they could not be matched with Still's controls (n=30). (FIG. 9A and FIG. 9B) Pie charts of cases (FIG. 9A) and controls (FIG. 9B) indicate the proportions of subjects with each self-identified ancestry; absolute numbers in each group are shown. The pie chart in FIG. 9A, shows proportionally, 36 white, 6 black, 7 Asian/So Asian and 6 Hispanic subjects; and the pie chart in FIG. 9B shows proportionally 19 white, 4 black, 3 Asian/So Asian, and 4 Hispanic subjects. As expected, this ancestry distribution is consistent with that of the US 2020 census data. FIG. 9C is a bar graph showing the percentages are of delayed hypersensitivity reaction cases and drug-tolerant controls with HLA-DRB1*15:XX, in Still's+KD subjects of all ancestries and in self-identified White subjects. FIG. 9D is a bar graph showing the number of cases in Still's disease+KD subjects (Still's-DRESS and KD-sAR) with and without HLA-DRB1*15:XX in all ancestries and in each indicated ancestry group are shown. All subjects with HLA-DRB*3/4/5 information (n=34) carry both HLA-DRB1*15 and HLA-DRB5*01:01. HLA-DRB1*15:XX, any HLA-DRB1*15; self-identified, self-reported ancestry; KD, Kawasaki disease, Mixed White, White+non-White ancestry. [1]Includes one Still's drug-reactive case with suspected delayed anakinra reaction.

DETAILED DESCRIPTION

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "gene" refers to a DNA sequence in a chromosome that codes for a product (either RNA or its translation product, a polypeptide). A gene contains a coding region and includes regions preceding and following the coding region. The coding region is comprised of a plurality of coding segments ("exons") and intervening sequences ("introns") between individual coding segments. A gene can also comprise a non-coding RNA product such as a miRNA or lncRNA gene.

The term "allele" refers to varying forms of the genomic DNA located at a given site. For example, "allele" refers to a genetic variant of a specific genomic location (locus). Alleles include silent nucleotide substitutions and nucleotide substitutions that alter the amino acid sequence of the encoded protein. In some instances, alleles may result in alternative RNA splicing.

"Genotype" refers to the chemical composition of polynucleotide sequences within the genome of an individual. For example, the genotype may include single-nucleotide variants (SNVs) and/or single nucleotide polymorphisms (SNPs).

As used herein, a "haplotype" is one or a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more genetic markers in a given chromosomal region in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minis satellites.

The term "human leukocyte antigen" or "HLA" refers to the complex of proteins encoded by the major histocompatibility complex gene complex in humans. The proteins are present on the surface of cells, and assist in regulating the immune system, for example, by presenting antigenic peptides. HLA genes encoding for the group of HLA proteins have different alleles, thus providing different functionality to the gene products. HLA proteins belonging to MHC class I (e.g. HLA-A, HLA-B and HLA-C) typically present peptides from within the cell (e.g. viral antigenic peptides). HLA proteins belonging to MHC class II (e.g. HLA-DP, HLA-DQ, HLA-DR) typically present peptides from outside of the cell. HLA MHC class II proteins occur on immune system cells including B cells, monocytes, dendritic cells, and activated T cells. MHC class II proteins include HLA-DP, HLA-DQ, and HLA-DR, heterodimer cell-surface receptors including an alpha-chain subunit and beta-chain subunit (e.g. HLA-DRB1 protein). HLA-DR beta chain is encoded by several loci, including the HLA-DRB1 locus.

The HLA-DRB1 locus encodes multiple HLA-DRB1 alleles, including but not limited to HLA-DRB1*15:01, HLA-DRB1*15:03, and HLA-DRB1*15:06.

HLA alleles may be referred using standard nomenclature well known in the art. For example, each HLA allele has a unique name including a number corresponding to up to four sets of digits separated by colons, where each set of digits includes two digits (e.g. 8 total digits). The digits before the first colon describe the allele type/family, which may correspond to the serological antigen carried by an allotype. The second set of digits list subtypes, with numbers assigned in the order in which DNA sequences have been determined. Alleles whose numbers differ in the two sets of digits differ in one or more nucleotide substitutions that alter the amino acid sequence of the encoded protein. Alleles that differ by synonymous nucleotide substitutions (e.g. silent or non-coding substitutions) within the coding sequence are distinguished by the use of the third set of digits. Alleles that differ by sequence polymorphisms in non-coding regions of the gene, for example in the introns, or in the 5' or 3' untranslated regions that flank the exons and introns, are distinguished by the use of the fourth set of digits. The naming of HLA alleles is standardized and is described in Hurley, C. K. Haming HLA diversity: A review of HLA nomenclature; Human Immunology, 2020.

HLA genes are highly polymorphic and genotyping may be used to determine alleles at each gene. Methods for genotyping HLA are well known and include serological antibody-based methods and DNA-based genotyping methods. Antibody tests may be used to genotype HLA at the two-digit level by determining antigen recognition of the alleles. For higher resolution genotyping (e.g. four-digit, six-digit, eight-digit, etc.) DNA based methods include, but are not limited to polymerase chain reaction (PCR) methods using sequence-specific oligonucleotide (SSO), Sanger sequencing-based typing (SBT), targeted amplicon sequencing (PCR-next generation sequencing, also known as PCT-NGS), whole-genome sequence (WGS) and whole-exome sequence (WES) methods. Thus, in embodiments, HLA genotyping is at the two-digit resolution level (e.g. identifying alleles associated with an antigen group). In embodiments, HLA genotyping is at the four-digit level (e.g. identifying alleles corresponding to a specific protein within an antigen group). In embodiments, HLA genotyping is at the six-digit level (e.g. identifying alleles with synonymous nucleotide substitutions, also known as silent or non-coding substitutions). In embodiments, HLA genotyping is at the 8-digit level (e.g. identifying alleles with polymorphisms in non-coding regions, for example exons, of the gene). Methods for genotyping HLA are well known in the art and described for example, by Wang C, Krishnakumar S, Wilhelmy J, et al. High-throughput, high-fidelity HLA genotyping with deep sequencing. *Proc Natl Acad Sci USA* 2012; 109(22): 8676-81; Thorstenson Y R, Creary L E, Huang H, et al. Allelic resolution NGS HLA typing of Class I and Class II loci and haplotypes in Cape Town, South Africa. *Hum Immunol* 2018; 79(12): 839-47; Huang Y, Yang J, Ying D, et al. HLAreporter: a tool for HLA typing from next generation sequencing data. *Genome Med* 2015; 7(1): 25; Li H, Durbin R. Fast and accurate long-read alignment with Burrows-Wheeler transform. *Bioinformatics* 2010; 26(5): 589-95; Warren R L, Holt R A. Targeted assembly of short sequence reads. *PLoS One* 2011; 6(5): e19816; Dilthey A T, Mentzer A J, Carapito R, et al. HLA*LA-HLA typing from linearly projected graph alignments. *Bioinformatics* 2019; 35(21): 4394-6; Li H. Aligning sequence reads, clone sequences and assembly contigs with BWA-MEM. *ArXiv e-prints,* 2013; Delcher A L, Phillippy A, Carlton J, Salzberg S L. Fast algorithms for large-scale genome alignment and comparison. *Nucleic Acids Res* 2002; 30(11): 2478-83.

For specific proteins described herein, the named protein includes any of the protein's naturally occurring forms, variants or homologs that maintain the protein activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "HLA-DRB1" or "HLA-DRB1 protein" as provided herein includes any of the recombinant or naturally-occurring forms of the human leukocyte antigen (HLA) DRB1 beta chain 1 protein, also known as HLA class II histocompatibility antigen DRB1 beta chain, human leukocyte antigen DRB1, HLA DRB1 beta chain 1 or variants or homologs thereof that maintain HLA DRB1 protein activity (e.g. within at least 50%, 80%, 90%, 95%, 96%, 97%, 98%, 99% or 100% activity compared to HLA DRB1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HLA DRB1 polypeptide. In embodiments, HLA DRB1 is the protein as identified by the UniProt sequence reference P01911, homolog or functional fragment thereof.

The term "HLA-DRB5" or "HLA-DRB5 protein" as provided herein includes any of the recombinant or naturally-occurring forms of the human leukocyte antigen (HLA) DRB5 beta chain protein, also known as HLA class II histocompatibility antigen DRB5 beta chain, DR beta-5, DR2-beta-2, MHC class II antigen DRB5 or variants or homologs thereof that maintain HLA DRB5 protein activity (e.g. within at least 50%, 80%, 90%, 95%, 96%, 97%, 98%, 99% or 100% activity compared to HLA DRB5). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring HLA DRB5 polypeptide. In embodiments, HLA DRB5 is the protein as identified by the UniProt sequence reference Q30154, homolog or functional fragment thereof.

A "therapeutic agent" as referred to herein, is a composition useful in treating or preventing a disease such as an inflammatory condition (e.g., sJIA or KD). In embodiments, the therapeutic agent is an anti-inflammatory agent. "Anti-inflammatory agent" is used in accordance with its plain ordinary meaning and refers to a composition (e.g. compound, drug, antagonist, inhibitor, modulator) that down-regulates or suppresses cytokine activity and/or leucocyte recruitment. In embodiments, an anti-inflammatory agent may treat or prevent an inflammatory condition. In embodiments, an anti-inflammatory agent may treat or prevent delayed hypersensitivity reactions (DHR). In embodiments, an anti-inflammatory agent is an IL-1 inhibitor. In embodiments, an anti-inflammatory agent is an IL-6 inhibitor. In embodiments, an anti-inflammatory agent is an agent approved by the FDA or similar regulatory agency of a country other than the USA, for treating an inflammatory condition. Anti-inflammatory agents include, but are not limited to ruxolitinib, etanercept, adalimumab, infliximab, certolizumab, pegol, golimumab, tocilizumab, siltuximab, sarilumab, olokizumab, sirukumab, rilonacept, canakinumab, anakinra, vedolizumab, natalizumab, dexamethasone, prednisone, fluticasone, hydrocortisone, tofacitinib, baricitinib, ustekinumab, briakinumab, guselkumab, tildrakizumab, Enaminone E121, JODI-18, JODI-19, TAK-242, C34 and C35.

The terms "anti-IL-1", in the context of a therapy, and "IL-1 inhibitor" are used interchangeably and refer to a molecule (e.g. compound, peptide, protein, nucleic acid, etc.) that downregulates or inhibits the activity or signaling of IL-1 or the IL-1 receptor relative to the absence of the compound. IL-1 inhibitors may be used to treat inflammatory conditions (e.g. rheumatic diseases). IL-1 inhibitors may bind to the IL-1 receptor (e.g. anakinra) or may directly bind to IL-1 (e.g. rilonacept and canakinumab). IL-1 inhibitors include, but are not limited to anakinra, canakinumab, and rilonacept.

The terms "anti-IL-6", in the context of a therapy, and "IL-6 inhibitor" are used interchangeably and refer to a molecule (e.g. compound, peptide, protein, nucleic acid, etc.) that downregulates or inhibits the activity or signaling of IL-6 or the IL-6 receptor relative to the absence of the compound. IL-6 inhibitors may be used to treat inflammatory diseases and cancers. IL-6 inhibitors may bind directly to IL-6 or the IL-6 receptor. IL-6 inhibitors include but are not limited to satralizumab, sarilumab, tocilizumab, siltuximab, olokizumab, and sirukumab.

The terms "disorder" or "disease" as provided herein are used interchangeably and refer to any deviation from the normal health of a mammal and include a state when disease/disorder symptoms are present, as well as conditions in which a deviation (e.g., chemical imbalance, infection, gene mutation, genetic defect, etc.) has occurred, but symptoms are not yet manifested or are not yet fully manifested. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, adult onset Still's disease (AOSD) or Kawasaki disease (KD), rheumatoid arthritis, undifferentiated autoinflammatory disorder, giant cell arteritis, COVID-19 related cytokine storm, diabetes mellitus type 1, graft-versus-host disease (GvHD), Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

The term "hypersensitivity" as provided herein is used according to its common meaning in the art and refers to an undesirable immune response (e.g. in response to a therapeutic agent). In embodiments, hypersensitivity is a delayed hypersensitivity reaction. Delayed hypersensitivity reaction (DHR), also referred to as Type IV hypersensitivity, refers to an immune-cell mediated response and is used according to its common meaning in the art, including pseudoallergic reactions resulting from an enhanced immunologic or inflammatory response. For example, presentation of antigenic peptides on antigen presenting cells stimulates proliferation of CD4+ T cells, thereby causing release of cytokines further mediating the immune response. Overproduction of cytokines caused by DHR may result in cell death and tissue damage. As provided herein, presence of certain HLA-DRB1*15 alleles in a subject may indicate the subject is at risk of DHR associated with certain therapeutic agents (e.g. anti-IL-1 therapy or anti-IL-6 therapy).

"Patient", "subject", or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" refers to a primary composition or therapy being administered at the same time as, or just prior to, or just after, the administration of one or more additional therapies, which may also be referred to as a "co-therapy" or "adjunctive" therapy. Co-administration is meant to include simultaneous or sequential administration.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

"Contacting" is used in accordance with its plain ordinary meaning and refers to the process of allowing at least two distinct species (e.g. antibodies and antigens) to become sufficiently proximal to react, interact, or physically touch. It should be appreciated; however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition, and a cell. In embodiments contacting includes, for example, allowing a pharmaceutical composition as described herein to interact with a cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

Methods

Applicants have discovered that particular HLA-DRB1*15 alleles are associated with risk of delayed hypersensitivity reactions (DHR) associated with certain classes of therapeutic agents. The therapeutic agents, IL-1 and IL-6 inhibitors, are used for treating a variety of inflammatory conditions. Thus, provided herein are, inter alia, methods of treating subjects in need of an anti-IL-1 or an anti-IL-6 therapy or are receiving an anti-IL-1 or an anti-IL-6 therapy. The method includes direct or indirect detection of an HLA-DRB1*15 allele. Indirect detection includes detection of genetically linked surrogates as appropriate for particular ethnicities (e.g. a haplotype) to HLA-DRB1*15 alleles or detection of alleles that may be proxy for HLA-DRB1*15 alleles. The method includes discontinuing administration of the anti-IL-1 or anti-IL-6 therapy, administering an altered dose of the anti-IL-1 or anti-IL-6 therapy, or administering the anti-IL-1 therapy and anti-IL-6 therapy in combination with an additional pharmaceutical composition. The methods provided herein, including embodiments thereof, are contemplated to decrease or prevent drug-associated delayed hypersensitivity reactions associated with HLA-DRB1*15 alleles. The methods are contemplated to treat or prevent inflammatory conditions (e.g. sJIA, KD, and Still's Disease, etc.) that are treated with anti-IL-1 or anti-IL-6 therapies.

Thus, in an aspect is provided a method of treating a subject receiving an anti-IL-1 therapy or an anti-IL-6 therapy. The method includes: (a) detecting an HLA-DRB1*15 allele in a biological sample received from the subject receiving the anti-IL-1 therapy or the anti-IL-6 therapy; and (b) discontinuing the anti-IL-1 therapy or the anti-IL-6 therapy, administering an altered dose of the anti-IL-1 therapy or the anti-IL-6 therapy to the subject, or administering the anti-IL-1 therapy or the anti-IL-6 therapy in combination with an additional pharmaceutical composition.

In embodiments, the method includes discontinuing the anti-IL-1 therapy or the anti-IL-6 therapy. Discontinuing the anti-IL-1 therapy or the anti-IL-6 therapy may include stopping administration of the anti-IL-1 therapy or the anti-IL-6 therapy. Discontinuing the anti-IL-1 therapy or the anti-IL-6 therapy may include stopping administration of the anti-IL-1 therapy or the anti-IL-6 therapy for a period of time and subsequently continuing administration the anti-IL-1 therapy or the anti-IL-6 therapy. Discontinuing the anti-IL-1 therapy or the anti-IL-6 therapy may include stopping administration of the anti-IL-1 therapy or the anti-IL-6 therapy for a period of time and subsequently continuing administration of an altered dose and/or an altered frequency of the anti-IL-1 therapy or the anti-IL-6 therapy. Discontinuing the anti-IL-1 therapy or the anti-IL-6 therapy may include stopping administration of the anti-IL-1 therapy or the anti-IL-6 therapy for a period of time and subsequently continuing administration of the anti-IL-1 therapy or the anti-IL-6 therapy in combination with an additional pharmaceutical composition.

In embodiments, the method includes administering an altered dose of the anti-IL-1 therapy or the anti-IL-6 therapy. In embodiments, administering an altered dose includes decreasing the dose or decreasing the frequency of administration of the anti-IL-1 therapy or the anti-IL-6 therapy.

In embodiments, the method includes administering an altered dose of the anti-IL-1 therapy or the anti-IL-6 therapy. In embodiments, administering an altered dose includes increasing the dose or increasing the frequency of administration of the anti-IL-1 therapy or the anti-IL-6 therapy. In accordance with these embodiments, the dose of the anti-IL-1 or anti-IL-6 therapy may be increased from about 2-times to about 25-fold compared to the original dose and/or the frequency of administration may be increased up to a continuous infusion. In accordance with these embodiments, the high dose and/or high frequency anti-IL-1 or anti-IL-6 therapy is sufficient to suppress the drug related hypersensitivity reaction. In embodiments, the high dose and/or high frequency anti-IL-1 or anti-IL-6 therapy is combined with at least one other anti-inflammatory therapy, such as steroid therapy.

In embodiments, administering an altered dose includes decreasing the dose of the anti-IL-1 therapy or the anti-IL-6 therapy. In embodiments, the decreased dose is 20% to 80% of the originally administered dose of the anti-IL-1 therapy or the anti-IL-6 therapy. In embodiments, the decreased dose is 25% to 80% of the originally administered dose of the anti-IL-1 therapy or the anti-IL-6 therapy. In embodiments, the decreased dose is 30% to 80% of the originally administered dose of the anti-IL-1 therapy or the anti-IL-6 therapy. In embodiments, the decreased dose is 35% to 80% of the originally administered dose of the anti-IL-1 therapy or the anti-IL-6 therapy. In embodiments, the decreased dose is 40% to 80% of the originally administered dose of the anti-IL-1 therapy or the anti-IL-6 therapy. In embodiments, the decreased dose is 45% to 80% of the originally administered dose of the anti-IL-1 therapy or the anti-IL-6 therapy. In embodiments, the decreased dose is 50% to 80% of the originally administered dose of the anti-IL-1 therapy or the anti-IL-6 therapy. In embodiments, the decreased dose is 55% to 80% of the originally administered dose of the anti-IL-1 therapy or the anti-IL-6 therapy. In embodiments, the decreased dose is 60% to 80% of the originally administered dose of the anti-IL-1 therapy or the anti-IL-6 therapy.

In embodiments, the decreased dose is 65% to 80% of the originally administered dose of the anti-IL-1 therapy or the anti-IL-6 therapy. In embodiments, the decreased dose is 70% to 80% of the originally administered dose of the anti-IL-1 therapy or the anti-IL-6 therapy. In embodiments, the decreased dose is 75% to 80% of the originally administered dose of the anti-IL-1 therapy or the anti-IL-6 therapy.

In embodiments, the decreased dose is 20% to 75% of the originally administered dose of the anti-IL-1 therapy or the anti-IL-6 therapy. In embodiments, the decreased dose is 20% to 70% of the originally administered dose of the anti-IL-1 therapy or the anti-IL-6 therapy. In embodiments, the decreased dose is 20% to 65% of the originally administered dose of the anti-IL-1 therapy or the anti-IL-6 therapy. In embodiments, the decreased dose is 20% to 60% of the originally administered dose of the anti-IL-1 therapy or the anti-IL-6 therapy. In embodiments, the decreased dose is 20% to 55% of the originally administered dose of the anti-IL-1 therapy or the anti-IL-6 therapy. In embodiments, the decreased dose is 20% to 50% of the originally administered dose of the anti-IL-1 therapy or the anti-IL-6 therapy. In embodiments, the decreased dose is 20% to 45% of the originally administered dose of the anti-IL-1 therapy or the anti-IL-6 therapy. In embodiments, the decreased dose is 20% to 40% of the originally administered dose of the anti-IL-1 therapy or the anti-IL-6 therapy. In embodiments, the decreased dose is 20% to 35% of the originally administered dose of the anti-IL-1 therapy or the anti-IL-6 therapy. In embodiments, the decreased dose is 20% to 30% of the originally administered dose of the anti-IL-1 therapy or the anti-IL-6 therapy. In embodiments, the decreased dose is 20% to 25% of the originally administered dose of the anti-IL-1 therapy or the anti-IL-6 therapy. In embodiments, the decreased dose is 20%, 25%, 30%, 35%, 40%, 45%, 50%, 55%, 60%, 65%, 70%, 75%, or 80% of the originally administered dose of the anti-IL-1 therapy or the anti-IL-6 therapy.

In embodiments, the decreased dose is 20% to 80% of the dose of anti-IL-1 therapy or the anti-IL-6 recommended for treating systemic juvenile idiopathic arthritis (sJIA) or adult-onset Still's Disease (AOSD), collectively known as Still's disease. In embodiments, the decreased dose is 25% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 30% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 35% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 40% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 45% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 50% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 55% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 60% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 65% to 80% of the dose of anti-IL-1 therapy or the anti-IL-6 recommended for treating systemic juvenile idiopathic arthritis (sJIA) or adult-onset Still's Disease (AOSD). In embodiments, the decreased dose is 70% to 80% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 75% to 80% of the dose of anti-IL-1 therapy or the anti-IL-6 therapy recommended for treating systemic juvenile idiopathic arthritis (sJIA) or adult-onset Still's Disease (AOSD).

In embodiments, the decreased dose is 20% to 75% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20% to 70% of the dose of anti-IL-1 therapy or the anti-IL-6 recommended for treating systemic juvenile idiopathic arthritis (sJIA) or adult-onset Still's Disease (AOSD). In embodiments, the decreased dose is 20% to 65% of the dose of anti-IL-1 therapy or the anti-IL-6 recommended for treating systemic juvenile idiopathic arthritis (sJIA) or adult-onset Still's Disease (AOSD). In embodiments, the decreased dose is 20% to 60% of the dose of anti-IL-1 therapy or the anti-IL-6 recommended for treating systemic juvenile idiopathic arthritis (sJIA) or adult-onset Still's Disease (AOSD). In embodiments, the decreased dose is 20% to 55% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20% to 50% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20% to 45% of the dose of anti-IL-1 therapy or the anti-IL-6 recommended for treating systemic juvenile idiopathic arthritis (sJIA) or adult-onset Still's Disease (AOSD). In embodiments, the decreased dose is 20% to 40% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20% to 35% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20% to 30% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20% to 25% of the dose of anti-IL-1 therapy or the anti-IL-6 therapy recommended for treating systemic juvenile idiopathic arthritis (sJIA) or adult-onset Still's Disease (AOSD). In embodiments, the decreased dose is 20%, 25%, 30%, 35%, 40%, 45%, 50%, 55%, 60%, 65%, 70%, 75% or 80% of the dose of anti-IL-1 therapy or the anti-IL-6 therapy recommended for treating systemic juvenile idiopathic arthritis (sJIA) or adult-onset Still's Disease (AOSD). In embodiments, the decreased dosage is 50% of anti-IL-1 therapy or the anti-IL-6 therapy recommended for treating sJIA or AOSD.

In embodiments, the decreased dosage is effective for treating or preventing an inflammatory disorder in the subject. In embodiments, the decreased dosage is effective for treating or preventing a monogenic inflammatory disorder in the subject. In embodiments, the decreased dosage does not cause hypersensitivity related to the anti-IL-1 therapy or the anti-IL-6 therapy in the subject.

In embodiments, altering the frequency includes decreasing the frequency of administration of the anti-IL-1 therapy or the anti-IL-6 therapy. In embodiments, the decreased frequency of administration is half the frequency of administration (e.g. instead of monthly administration, alternate monthly administration) recommended for the anti-IL-1 therapy or the anti-IL-6 therapy for treating sJIA or AOSD. In embodiments, the decreased frequency of administration is ¼ the frequency of administration recommended for the anti-IL-1 therapy or the anti-IL-6 therapy for treating sJIA or AOSD. In embodiments, the decreased frequency of administration is ⅛ the frequency of administration recommended for the anti-IL-1 therapy or the anti-IL-6 therapy for treating sJIA or AOSD. In embodiments, the decreased frequency of administration is 1/16 the frequency of administration recommended for the anti-IL-1 therapy or the anti-IL-6 therapy for treating sJIA or AOSD.

For example, the method of treatment may include administering half the dose of the anti-IL-1 therapy or the anti-IL-6 therapy at half the frequency typically recommended for treating sJIA or AOSD. In another example, for an anti-IL-1 therapy or an anti-IL-6 therapy that is administered daily, the dose can be altered by administering half the dose or administering the therapy every other day (e.g. at half the frequency).

In embodiments, the altered dose of the anti-IL-1 therapy or the anti-IL-6 therapy is 0.1 mg/kg to 4.5 mg/kg of anakinra. In embodiments, the altered dose of the anti-IL-1 therapy or the anti-IL-6 therapy is 0.5 mg/kg to 4.5 mg/kg of anakinra. In embodiments, the altered dose of the anti-IL-1 therapy or the anti-IL-6 therapy is 1 mg/kg to 4.5 mg/kg of anakinra. In embodiments, the altered dose of the anti-IL-1 therapy or the anti-IL-6 therapy is 1.5 mg/kg to 4.5 mg/kg of anakinra. In embodiments, the altered dose of the anti-IL-1 therapy or the anti-IL-6 therapy is 2 mg/kg to 4.5 mg/kg of anakinra. In embodiments, the altered dose of the anti-IL-1 therapy or the anti-IL-6 therapy is 2.5 mg/kg to 4.5 mg/kg of anakinra. In embodiments, the altered dose of the anti-IL-1 therapy or the anti-IL-6 therapy is 3 mg/kg to 4.5 mg/kg of anakinra. In embodiments, the altered dose of the anti-IL-1 therapy or the anti-IL-6 therapy is 3.5 mg/kg to 4.5 mg/kg of anakinra. In embodiments, the altered dose of the anti-IL-1 therapy or the anti-IL-6 therapy is 4 mg/kg to 4.5 mg/kg of anakinra.

In embodiments, the altered dose of the anti-IL-1 therapy or the anti-IL-6 therapy is 0.1 mg/kg to 4 mg/kg of anakinra. In embodiments, the altered dose of the anti-IL-1 therapy or the anti-IL-6 therapy is 0.1 mg/kg to 3.5 mg/kg of anakinra. In embodiments, the altered dose of the anti-IL-1 therapy or the anti-IL-6 therapy is 0.1 mg/kg to 3 mg/kg of anakinra. In embodiments, the altered dose of the anti-IL-1 therapy or the anti-IL-6 therapy is 0.1 mg/kg to 2.5 mg/kg of anakinra. In embodiments, the altered dose of the anti-IL-1 therapy or the anti-IL-6 therapy is 0.1 mg/kg to 2 mg/kg of anakinra. In embodiments, the altered dose of the anti-IL-1 therapy or the anti-IL-6 therapy is 0.1 mg/kg to 1.5 mg/kg of anakinra. In embodiments, the altered dose of the anti-IL-1 therapy or the anti-IL-6 therapy is 0.1 mg/kg to 1 mg/kg of anakinra. In embodiments, the altered dose of the anti-IL-1 therapy or the anti-IL-6 therapy is 0.1 mg/kg to 0.5 mg/kg of anakinra. In embodiments, the altered dose of the anti-IL-1 therapy or the anti-IL-6 therapy is 0.1 mg/kg, 0.5 mg/kg, 1 mg/kg, 1.5 mg/kg, 2 mg/kg, 2.5 mg/kg, 3 mg/kg, 3.5 mg/kg, 4 mg/kg or 4.5 mg/kg of anakinra.

In embodiments, the decreased frequency of administration of the anti-IL-1 therapy or the anti-IL-6 therapy is administration of anakinra every two days. In embodiments, the decreased frequency of administration of the anti-IL-1 therapy or the anti-IL-6 therapy is administration of anakinra every three days. In embodiments, the decreased frequency of administration of the anti-IL-1 therapy or the anti-IL-6 therapy is administration of anakinra every 4 days. In embodiments, the decreased frequency of administration of the anti-IL-1 therapy or the anti-IL-6 therapy is administration of anakinra every 5 days. In embodiments, the decreased frequency of administration of the anti-IL-1 therapy or the anti-IL-6 therapy is administration of anakinra every 6 days. In embodiments, the decreased frequency of administration of the anti-IL-1 therapy or the anti-IL-6 therapy is administration of anakinra once a week. In embodiments, the decreased frequency of administration of the anti-IL-1 therapy or the anti-IL-6 therapy is administration of anakinra once every two weeks. In embodiments, the decreased frequency of administration of the anti-IL-1 therapy or the anti-IL-6 therapy is administration of anakinra once every three weeks. In embodiments, the decreased frequency of administration of the anti-IL-1 therapy or the anti-IL-6 therapy is administration of anakinra once every four weeks.

In embodiments, the altered dose of the anti-IL-1 therapy or the anti-IL-6 therapy is 0.1 mg/kg to 3 mg/kg of canakimumab. In embodiments, the altered dose of the anti-IL-1 therapy or the anti-IL-6 therapy is 0.1 mg/kg to 2.5 mg/kg of canakimumab. In embodiments, the altered dose of the anti-IL-1 therapy or the anti-IL-6 therapy is 0.1 mg/kg to 2 mg/kg of canakimumab. In embodiments, the altered dose of the anti-IL-1 therapy or the anti-IL-6 therapy is 0.1 mg/kg to 1.5 mg/kg of canakimumab. In embodiments, the altered dose of the anti-IL-1 therapy or the anti-IL-6 therapy is 0.1 mg/kg to 1 mg/kg of canakimumab. In embodiments, the altered dose of the anti-IL-1 therapy or the anti-IL-6 therapy is 0.1 mg/kg to 0.5 mg/kg of canakimumab.

In embodiments, the altered dose of the anti-IL-1 therapy or the anti-IL-6 therapy is 0.5 mg/kg to 3 mg/kg of canakimumab. In embodiments, the altered dose of the anti-IL-1 therapy or the anti-IL-6 therapy is 1 mg/kg to 3 mg/kg of canakimumab. In embodiments, the altered dose of the anti-IL-1 therapy or the anti-IL-6 therapy is 1.5 mg/kg to 3 mg/kg of canakimumab. In embodiments, the altered dose of the anti-IL-1 therapy or the anti-IL-6 therapy is 2 mg/kg to 3 mg/kg of canakimumab. In embodiments, the altered dose of the anti-IL-1 therapy or the anti-IL-6 therapy is 2.5 mg/kg to 3 mg/kg of canakimumab. In embodiments, the altered dose of the anti-IL-1 therapy or the anti-IL-6 therapy is 0.1 mg/kg, 0.5 mg/kg, 1 mg/kg, 1.5 mg/kg, 2 mg/kg, 2.5 mg/kg or 3 mg/kg canakimumab.

In embodiments, the decreased frequency of administration of the anti-IL-1 therapy or the anti-IL-6 therapy is administration of canakimumab every 5 weeks. In embodiments, the decreased frequency of administration of the anti-IL-1 therapy or the anti-IL-6 therapy is administration of canakimumab every 6 weeks. In embodiments, the decreased frequency of administration of the anti-IL-1 therapy or the anti-IL-6 therapy is administration of canakimumab every 7 weeks. In embodiments, the decreased frequency of administration of the anti-IL-1 therapy or the anti-IL-6 therapy is administration of canakimumab every 8 weeks. In embodiments, the decreased frequency of administration of the anti-IL-1 therapy or the anti-IL-6 therapy is administration of canakimumab every 9 weeks. In embodiments, the decreased frequency of administration of the anti-IL-1 therapy or the anti-IL-6 therapy is administration of canakimumab every 10 weeks. In embodiments, the decreased frequency of administration of the anti-IL-1 therapy or the anti-IL-6 therapy is administration of canakimumab every 11 weeks. In embodiments, the decreased frequency of administration of the anti-IL-1 therapy or the anti-IL-6 therapy is administration of canakimumab every 12 weeks.

In embodiments, the altered dose of the anti-IL-1 therapy or the anti-IL-6 therapy is 0.5 mg/kg to 10 mg/kg of tocilizumab. In embodiments, the altered dose of the anti-IL-1 therapy or the anti-IL-6 therapy is 1 mg/kg to 10 mg/kg of tocilizumab. In embodiments, the altered dose of the anti-IL-1 therapy or the anti-IL-6 therapy is 1.5 mg/kg to 10 mg/kg of tocilizumab. In embodiments, the altered dose of the anti-IL-1 therapy or the anti-IL-6 therapy is 2 mg/kg to 10 mg/kg of tocilizumab. In embodiments, the altered dose of the anti-IL-1 therapy or the anti-IL-6 therapy is 2.5 mg/kg to 10 mg/kg of tocilizumab. In embodiments, the altered dose of the anti-IL-1 therapy or the anti-IL-6 therapy is 3 mg/kg to 10 mg/kg of tocilizumab. In embodiments, the altered dose of the anti-IL-1 therapy or the anti-IL-6 therapy is 3.5 mg/kg to 10 mg/kg of tocilizumab. In embodiments, the altered dose of the anti-IL-1 therapy or the anti-IL-6 therapy is 4 mg/kg to 10 mg/kg of tocilizumab. In embodiments, the altered dose of the anti-IL-1 therapy or the anti-IL-6 therapy is 4.5 mg/kg to 10 mg/kg of tocilizumab. In embodiments, the altered dose of the anti-IL-1 therapy or the anti-IL-6 therapy is 5 mg/kg to 10 mg/kg of tocilizumab. In embodiments, the altered dose of the anti-IL-1 therapy or the anti-IL-6 therapy is 5.5 mg/kg to 10 mg/kg of tocilizumab. In embodiments, the altered dose of the anti-IL-1 therapy or the anti-IL-6 therapy is 6 mg/kg to 10 mg/kg of tocilizumab. In embodiments, the altered dose of the anti-IL-1 therapy or the anti-IL-6 therapy is 6.5 mg/kg to 10 mg/kg of tocilizumab. In embodiments, the altered dose of the anti-IL-1 therapy or the anti-IL-6 therapy is 7 mg/kg to 10 mg/kg of tocilizumab. In embodiments, the altered dose of the anti-IL-1 therapy or the anti-IL-6 therapy is 7.5 mg/kg to 10 mg/kg of tocilizumab. In embodiments, the altered dose of the anti-IL-1 therapy or the anti-IL-6 therapy is 8 mg/kg to 10 mg/kg of tocilizumab. In embodiments, the altered dose of the anti-IL-1 therapy or the anti-IL-6 therapy is 8.5 mg/kg to 10 mg/kg of tocilizumab. In embodiments, the altered dose of the anti-IL-1 therapy or the anti-IL-6 therapy is 9 mg/kg to 10 mg/kg of tocilizumab. In embodiments, the altered dose of the anti-IL-1 therapy or the anti-IL-6 therapy is 9.5 mg/kg to 10 mg/kg of tocilizumab.

In embodiments, the altered dose of the anti-IL-1 therapy or the anti-IL-6 therapy is 0.5 mg/kg to 9.5 mg/kg of tocilizumab. In embodiments, the altered dose of the anti-IL-1 therapy or the anti-IL-6 therapy is 0.5 mg/kg to 9 mg/kg of tocilizumab. In embodiments, the altered dose of the anti-IL-1 therapy or the anti-IL-6 therapy is 0.5 mg/kg to 8.5 mg/kg of tocilizumab. In embodiments, the altered dose of the anti-IL-1 therapy or the anti-IL-6 therapy is 0.5 mg/kg to 8 mg/kg of tocilizumab. In embodiments, the altered dose of the anti-IL-1 therapy or the anti-IL-6 therapy is 0.5 mg/kg to 7.5 mg/kg of tocilizumab. In embodiments, the altered dose of the anti-IL-1 therapy or the anti-IL-6 therapy is 0.5 mg/kg to 7 mg/kg of tocilizumab. In embodiments, the altered dose of the anti-IL-1 therapy or the anti-IL-6 therapy is 0.5 mg/kg to 6.5 mg/kg of tocilizumab. In embodiments, the altered dose of the anti-IL-1 therapy or the anti-IL-6 therapy is 0.5 mg/kg to 6 mg/kg of tocilizumab. In embodiments, the altered dose of the anti-IL-1 therapy or the anti-IL-6 therapy is 0.5 mg/kg to 5.5 mg/kg of tocilizumab. In embodiments, the altered dose of the anti-IL-1 therapy or the anti-IL-6 therapy is 0.5 mg/kg to 4 mg/kg of tocilizumab. In embodiments, the altered dose of the anti-IL-1 therapy or the anti-IL-6 therapy is 0.5 mg/kg to 3.5 mg/kg of tocilizumab. In embodiments, the altered dose of the anti-IL-1 therapy or the anti-IL-6 therapy is 0.5 mg/kg to 3 mg/kg of tocilizumab. In embodiments, the altered dose of the anti-IL-1 therapy or the anti-IL-6 therapy is 0.5 mg/kg to 2.5 mg/kg of tocilizumab. In embodiments, the altered dose of the anti-IL-1 therapy or the anti-IL-6 therapy is 0.5 mg/kg to 2 mg/kg of tocilizumab. In embodiments, the altered dose of the anti-IL-1 therapy or the anti-IL-6 therapy is 0.5 mg/kg to 1.5 mg/kg of tocilizumab. In embodiments, the altered dose of the anti-IL-1 therapy or the anti-IL-6 therapy is 0.5 mg/kg to 1 mg/kg of tocilizumab.

In embodiments, the decreased frequency of administration of the anti-IL-1 therapy or the anti-IL-6 therapy is administration of tocilizumab every 3 weeks. In embodiments, the decreased frequency of administration of the anti-IL-1 therapy or the anti-IL-6 therapy is administration of tocilizumab every 4 weeks. In embodiments, the decreased frequency of administration of the anti-IL-1 therapy or the anti-IL-6 therapy is administration of tocilizumab every 5 weeks. In embodiments, the decreased frequency of administration of the anti-IL-1 therapy or the anti-IL-6 therapy is administration of tocilizumab every 6 weeks. In embodiments, the decreased frequency of administration of the anti-IL-1 therapy or the anti-IL-6 therapy is administration of tocilizumab every 7 weeks. In embodiments, the decreased frequency of administration of the anti-IL-1 therapy or the anti-IL-6 therapy is administration of tocilizumab every 8 weeks. In embodiments, the decreased frequency of administration of the anti-IL-1 therapy or the anti-IL-6 therapy is administration of tocilizumab every 9 weeks. In embodiments, the decreased frequency of administration of the anti-IL-1 therapy or the anti-IL-6 therapy is administration of tocilizumab every 10 weeks.

The method may include administering the anti-IL-1 therapy or the anti-IL-6 therapy in combination with an additional pharmaceutical composition. The additional pharmaceutical composition may treat the disease or condition (e.g. sJIA, AOSD, etc.) initially treated by the anti-IL-1 therapy or the anti-IL-6 therapy. The additional pharmaceutical treatment may not cause delayed hypersensitivity reactions in the subject receiving the anti-IL-1 therapy or an anti-IL-6 therapy, thus allowing for administration of decreased dosage or frequency of the anti-IL-1 therapy or an anti-IL-6 therapy to the subject. The additional pharmaceutical composition may treat the delayed drug hypersensitivity reaction, thus allowing continuation of the anti-IL-1 therapy or said anti-IL-6 therapy. In embodiments, the additional pharmaceutical composition is intravenous gamma globulin (IVIG), calcineurin inhibitors, Janus kinase (JAK) inhibitors, TNF inhibitors, corticosteroids or T-cell inhibitors. In embodiments, the calcineurin inhibitor is cyclosporine or tacrolimus. In embodiments, the calcineurin inhibitor is cyclosporine. In embodiments, the calcineurin inhibitor is tacrolimus. In embodiments, the Janus kinase (JAK) inhibitor is tofacitinib, baricitinib, ruxolitinib, or upadacitinib. In embodiments, the Janus kinase inhibitor is tofacitinib. In embodiments, the Janus kinase inhibitor is baricitinib. In embodiments, the Janus kinase inhibitor is ruxolitinib. In embodiments, the TNF inhibitor is adalimumab. In embodiments, the additional pharmaceutical composition is oral or parenteral dosing regimens of corticosteroids or T-cell inhibitors. In embodiments, the T-cell inhibitor is abatacept. In embodiments, the additional pharmaceutical composition is an anti-IL-5 therapy. In embodiments, the additional pharmaceutical composition is a cytokine blocker or a therapeutic for treatment of allergic diseases. In embodiments, the additional pharmaceutical composition is a corticosteroid preparation. In embodiments, the additional pharmaceutical composition is methotrexate. In embodiments, the additional pharmaceutical composition is leflonomide. In embodiments, the pharmaceutical compositions provided herein may be used singly with the anti-IL-1 therapy or the anti-IL-6 therapy. In embodiments, the pharmaceutical compositions provided herein may be used in various combinations with the anti-IL-1 therapy or the anti-IL-6 therapy.

The methods provided herein are contemplated for treatment of inflammatory conditions in subjects at risk of drug-related DHR associated with particular HLA-DRB1*15 alleles. Thus, in an aspect is provided a method of treating a subject in need of an anti-IL-1 therapy or an anti-IL-6 therapy. The method includes (a) detecting an HLA-DRB1*15 allele in a biological sample received from the subject in need of the anti-IL-1 therapy or the anti-IL-6 therapy; and (b) administering an alternative therapy to the subject.

In embodiments, the alternative therapy may treat the disease or condition initially treated by the anti-IL-1 therapy or the anti-IL-6 therapy. The alternative therapy may not cause delayed hypersensitivity reaction in the subject in need of the anti-IL-1 therapy or an anti-IL-6 therapy, thus allowing for treatment of the disease while avoiding delayed hypersensitivity reaction. In embodiments, the alternative therapy may treat or prevent delayed drug hypersensitivity reaction, thus allowing co-administration of the anti-IL-1 therapy or the anti-IL-6 therapy and the alternative therapy. In embodiments, the alternative therapy may treat or prevent delayed drug hypersensitivity reaction, thus allowing administration of the anti-IL-1 therapy or the anti-IL-6 therapy following administration of the alternative therapy.

In embodiments, the alternative therapy is intravenous gamma globulin (IVIG), calcineurin inhibitors, Janus kinase inhibitors, TNF inhibitors, corticosteroids or T-cell inhibitors. In embodiments, the calcineurin inhibitor is cyclosporine or tacrolimus. In embodiments, the calcineurin inhibitor is cyclosporine. In embodiments, the calcineurin inhibitor is tacrolimus. In embodiments, the Janus kinase inhibitor is tofacitinib, baricitinib or ruxolitinib. In embodiments, the Janus kinase inhibitor is tofacitinib. In embodiments, the Janus kinase inhibitor is baricitinib. In embodiments, the Janus kinase inhibitor is ruxolitinib. In embodiments, the TNF inhibitor is adalimumab, etanercept, or infliximab. In embodiments, the TNF inhibitor is adalimumab. In embodiments, the TNF inhibitor is etanercept. In embodiments, the TNF inhibitor is infliximab. In embodiments, the alternative therapy is oral or parenteral dosing regimens of corticosteroids or T-cell inhibitors. In embodiments, the T-cell inhibitor is abatacept. In embodiments, the alternative therapy is an IL-5 inhibitor therapy. In embodiments, the alternative therapy is a cytokine blocker or a therapeutic for treatment of allergic diseases. In embodiments, the alternative therapy is a T cell costimulation modulator. In embodiments, the T cell costimulation modulator is abatacept. In embodiments, the alternative therapy is methotrexate. In embodiments, the alternative therapy is leflonomide. In embodiments, the alternative therapy provided herein may be used singly. In embodiments, the alternative therapy provided herein may be used various combinations.

Applicants discovered that the presence of particular HLA-DRB1*15 alleles is associated with DHR in subjects receiving anti-IL-1 and anti-IL-6 therapies. Thus, the methods provided herein may be used for determining risk of drug related delayed hypersensitivity in subjects who are in need of, or are receiving, anti-IL-1 and/or anti-IL-6 therapies. Provided herein are, inter alia, methods of determining risk of drug related delayed hypersensitivity in a subject. The method includes detection of certain human leucocyte antigen (HLA) alleles that are associated with risk of drug hypersensitivity related to classes of therapeutics. Thus, in an aspect a method of identifying a subject at risk of hypersensitivity related to an anti-IL-1 therapy or an anti-IL-6 therapy is provided. The method includes detecting an HLA-DRB1*15 allele in a biological sample received from the subject.

In an aspect is provided a method of determining whether a subject is at risk of hypersensitivity related to an anti-IL-1 therapy or an anti-IL-6 therapy. The method includes determining whether an HLA-DRB1*15 allele is present in a biological sample received from the subject, wherein the presence of said HLA-DRB1*15 allele in said biological sample indicates said subject is at risk of hypersensitivity related to said anti-IL-1 therapy or said anti-IL-6 therapy.

In another aspect a method of analyzing a biological sample received from a subject receiving an anti-IL-1 therapy or an anti-IL-6 therapy is provided. The method includes detecting an HLA-DRB1*15 allele in the biological sample received from the subject receiving the anti-IL-1 therapy or the anti-IL-6 therapy.

In another aspect a method of analyzing a biological sample received from a subject in need of an anti-IL-1 therapy or an anti-IL-6 therapy is provided. The method includes detecting an HLA-DRB1*15 allele in the biological sample received from the subject in need of the anti-IL-1 therapy or the anti-IL-6 therapy.

In an aspect is provided a method for preparing a deoxyribonucleic acid (DNA) fraction from a subject receiving an anti-IL-1 therapy or an anti-IL-6 therapy useful for genotyping. The method includes: (a) extracting DNA from a biological sample from the subject receiving the anti-IL-1 therapy or the anti-IL-6 therapy; (b) producing a fraction of the DNA extracted in (a) thereby producing a DNA fraction; and (c) determining whether the DNA fraction includes an HLA-DRB1*15 allele.

In another aspect is provided a method for preparing a deoxyribonucleic acid (DNA) fraction from a subject in need of an anti-IL-1 therapy or an anti-IL-6 therapy useful for genotyping. The method includes: (a) extracting DNA from a biological sample from the subject in need of the anti-IL-1 therapy or the anti-IL-6 therapy; (b) producing a fraction of the DNA extracted in (a) thereby producing a DNA fraction; and (c) determining whether the DNA fraction includes an HLA-DRB1*15 allele.

For the methods provided herein, "extracting DNA" refers to processes well known in the art to purify or otherwise separate or isolate a nucleic acid (e.g. DNA) from a mixture (e.g. a cell lysate). In embodiments, extracting DNA includes purifying DNA to substantial purity to allow for DNA sequencing. In embodiments, step (c) includes sequencing the DNA to determine whether the DNA fraction includes an HLA-DRB1*15 allele. In embodiments, sequencing is next-generation sequencing. In embodiments, step (c) includes reverse sequence-specific oligonucleotide (rSSO) DNA genotyping. In embodiments, step (c) includes determining HLA genotype from whole exome sequencing (WES) data.

For the methods provided herein, in embodiments, the HLA-DRB1*15 allele is an HLA-DRB1*15:01 allele, HLA-DRB1*15:03 allele and/or a HLA-DRB1*15:06 allele. In embodiments, the HLA-DRB1*15 allele is an HLA-DRB1*15:01 allele. In embodiments, the HLA-DRB1*15 allele is an HLA-DRB1*15:03 allele. In embodiments, the HLA-DRB1*15 allele is an HLA-DRB1*15:06 allele. For the methods provided herein, the HLA-DRB1*15 allele is not an HLA-DRB1*15:02 allele.

For the methods provided herein, in embodiments, the method includes direct detection or indirect detection of an HLA-DRB1*15 allele. In embodiments, the detection is direct detection. In embodiments, the detection is indirect detection. In embodiments, the indirect detection includes detection of a genetically linked surrogate, such as, but not limited to a HLA-DRB5 allele (e.g. DRB5*01:01). In embodiments, the genetically linked surrogate is an HLA allele in the same haplotype as an HLA-DRB1*15 allele. In embodiments, HLA-DRB1*15:01 is indirectly detected by detecting a HLA-DRB5 allele. In embodiments, HLA-DRB1*15:03 is indirectly detected by detecting a HLA-DRB5 allele. In embodiments, HLA-DRB1*15:06 is indirectly detected by detecting a HLA-DRB5 allele. In embodiments, HLA-DRB1*15:01 is indirectly detected by detecting HLA-DRB5*01:01. In embodiments, HLA-DRB1*15:03 is indirectly detected by detecting HLA-DRB5*01:01. In embodiments, HLA-DRB1*15:06 is indirectly detected by detecting HLA-DRB5*01:01.

Thus, for the methods provided herein, in embodiments, determining whether an HLA-DRB1*15 allele is present includes determining whether a genetically linked surrogate is present. In embodiments, determining whether a HLA-DRB1*15 allele is present includes determining whether a HLA-DRB5 allele is present. In embodiments, determining whether HLA-DRB1*15:01 is present includes determining whether an HLA-DRB5 allele is present. In embodiments, determining whether HLA-DRB1*15:03 is present includes determining whether an HLA-DRB5 allele is present. In embodiments, determining whether HLA-DRB1*15:06 is present includes determining whether an HLA-DRB5 allele is present. In embodiments, determining whether HLA-DRB1*15:01 is present includes determining whether HLA-DRB5*01:01 is present. In embodiments, determining whether HLA-DRB1*15:03 is present includes determining whether HLA-DRB5*01:01 is present. In embodiments, determining whether HLA-DRB1*15:06 is present includes determining whether HLA-DRB5*01:01 is present.

The methods provided herein, including embodiments thereof, are contemplated to be useful for treating or preventing inflammatory disease. Thus, for the methods provided herein, in embodiments, the subject has inflammatory disease. In embodiments, the inflammatory disease is systemic juvenile idiopathic arthritis (sJIA), adult onset Still's disease (AOSD), rheumatoid arthritis, childhood polyarticular juvenile arthritis, macrophage activation syndrome (MAS), a monogenic disorder causing an auto-inflammation disorder, an undifferentiated auto-inflammatory syndrome with over-activation of the inflammasome, cytokine storm syndrome, type 2 diabetes, gout, multiple sclerosis, asthma, pericarditis, ST-segment elevation, myocardial infarction, heart failure with reduced ejection fraction, a rheumatic disease, a malignancy or a genetic disease. In embodiments, the inflammatory disease is sJIA. In embodiments, the inflammatory disease is AOSD. In embodiments, the inflammatory disease is rheumatoid arthritis. In embodiments, the inflammatory disease is childhood polyarticular juvenile arthritis. In embodiments, the inflammatory disease is MAS. In embodiments, the inflammatory disease is a monogenic disorder causing an auto-inflammation disorder. In embodiments, the inflammatory disease is an undifferentiated auto-inflammatory syndrome with over-activation of the inflammasome. In embodiments, the inflammatory disease is cytokine storm syndrome. In embodiments, the inflammatory disease is type 2 diabetes. In embodiments, the inflammatory disease is gout. In embodiments, the inflammatory disease is multiple sclerosis. In embodiments, the inflammatory disease is asthma. In embodiments, the inflammatory disease is pericarditis. In embodiments, the inflammatory disease is ST-segment elevation. In embodiments, the inflammatory disease is myocardial infarction. In embodiments, the inflammatory disease is heart failure with reduced ejection fraction. In embodiments, the inflammatory disease is a rheumatic disease. In embodiments, the inflammatory disease is a malignancy. In embodiments, the malignancy is lung cancer. In embodiments, the inflammatory disease is a genetic disease. In embodiments, the genetic disease is a hereditary autoinflammatory disorder.

In some instances, the macrophage activation syndrome (MAS) occurs de novo in the context of an inflammatory or rheumatologic condition, due to a malignancy, during a drug reaction, or due to an infection (e.g. COVID-19). In some instances, the cytokine storm syndrome is associated with sJIA, AOSD, systemic lupus erythematosus (SLE), COVID-19, multi-inflammatory syndrome in children (MIS-C), CAR-T therapy, dermatomyositis (juvenile and adult), rheumatic diseases, malignancies, or other infection-associated settings. In embodiments, the cytokine storm is primary hemophagocytic lymphohistocytosis (HLH) or secondary HLH. In embodiments, the cytokine storm is primary HLH. In embodiments, the cytokine storm is secondary HLH.

For the methods provided herein, in embodiments, the subject has a delayed hypersensitivity disorder. In embodiments, the delayed hypersensitivity disorder is drug-related.

For the methods provided herein, in embodiments, the subject has sJIA, AOSD or Kawasaki disease. In embodiments, the subject has sJIA. In embodiments, the subject has AOSD. In embodiments, the subject has Kawasaki disease.

For the methods provided herein, in embodiments, the anti-IL-1 therapy or the anti-IL-6 therapy is anakinra therapy, canakinumab therapy, rilonacept therapy, tocilizumab therapy, sarilumab therapy, or satralizumab therapy. In embodiments, the anti-IL-1 therapy or the anti-IL-6 therapy is anakinra therapy. In embodiments, the anti-IL-1 therapy or the anti-IL-6 therapy is canakinumab therapy. In embodiments, the anti-IL-1 therapy or the anti-IL-6 therapy is rilonacept therapy. In embodiments, the anti-IL-1 therapy or the anti-IL-6 therapy is tocilizumab therapy. In embodiments, the anti-IL-1 therapy or the anti-IL-6 therapy is sarilumab therapy. In embodiments, the anti-IL-1 therapy or the anti-IL-6 therapy is satralizumab therapy.

Additional Embodiments

In embodiments, provided herein is a method of treating a subject receiving an anti-IL-1 therapy or an anti-IL-6 therapy, the method including: (a) detecting an HLA-DRB1*15 allele in a biological sample received from said subject receiving said anti-IL-1 inhibitor therapy or said anti-IL-6 inhibitor therapy; and (b) discontinuing said anti-IL-1 inhibitor therapy or said anti-IL-6 inhibitor therapy, administering an altered dose of said anti-IL-1 inhibitor therapy or said anti-IL-6 inhibitor therapy to said subject, or administering said anti-IL-1 inhibitor therapy or said anti-IL-6 inhibitor therapy in combination with an additional pharmaceutical composition.

In other embodiments, provided herein is a method of treating a subject in need of an anti-IL-1 therapy or an anti-IL-6 therapy, the method including (a) detecting an HLA-DRB1*15 allele in a biological sample received from said subject in need of said anti-IL-1 inhibitor therapy or said anti-IL-6 inhibitor therapy; and administering an anti-IL-1/IL-6 alternative therapy to said subject.

In embodiments, provided herein is a method of identifying a subject at risk of hypersensitivity related to an anti-IL-1 therapy or an anti-IL-6 therapy, the method including detecting an HLA-DRB1*15 allele in a biological sample received from the subject.

In embodiments, provided herein is a method of determining whether a subject is at risk of hypersensitivity related to an anti-IL-1 therapy or an anti-IL-6 therapy, the method including determining whether an HLA-DRB1*15 allele is present in a biological sample received from the subject, wherein the presence of said HLA-DRB1*15 allele in the biological sample indicates said subject is at risk of hypersensitivity related to the anti-IL-1 therapy or the anti-IL-6 therapy.

In embodiments, provided herein is a method of analyzing a biological sample received from a subject receiving an anti-IL-1 therapy or an anti-IL-6 therapy, the method including detecting an HLA-DRB1*15 allele in said biological sample received from said subject receiving said anti-IL-1 inhibitor therapy or said anti-IL-6 inhibitor therapy.

In embodiments, provided herein is a method of analyzing a biological sample received from a subject in need of an anti-IL-1 therapy or an anti-IL-6 therapy, the method including detecting an HLA-DRB1*15 allele in said biological sample received from said subject in need of said anti-IL-1 therapy or said anti-IL-6 therapy.

In embodiments, provided herein is a method for preparing a deoxyribonucleic acid (DNA) fraction from a subject receiving an anti-IL-1 therapy or an anti-IL-6 therapy useful for genotyping, the method including (a) extracting DNA from a biological sample from said subject receiving said anti-IL-1 therapy or said anti-IL-6 therapy; (b) producing a fraction of the DNA extracted in (a) thereby producing a DNA fraction; and (c) determining whether said DNA fraction comprises an HLA-DRB1*15 allele.

In embodiments, provided herein is a method for preparing a deoxyribonucleic acid (DNA) fraction from a subject in need of an anti-IL-1 therapy or an anti-IL-6 therapy useful for genotyping, the method including (a) extracting DNA from a biological sample from said subject in need of said anti-IL-1 therapy or said anti-IL-6 therapy; (b) producing a fraction of the DNA extracted in (a) thereby producing a DNA fraction; and (c) determining whether said DNA fraction comprises an HLA-DRB1*15 allele.

In embodiments, the methods herein include that the HLA-DRB1*15 allele is an HLA-DRB1*15:01 allele, HLA-DRB1*15:03 allele and/or a HLA-DRB1*15:06 allele.

In embodiments, the HLA-DRB1*15 allele is not an HLA-DRB1*15:02 allele.

In embodiments, the subject has an inflammatory disease.

In embodiments, the subject has systemic juvenile idiopathic arthritis, adult onset Still's disease or Kawasaki disease.

In embodiments, the anti-IL-1 therapy or said anti-IL-6 therapy is anakinra therapy, canakinumab therapy, rilonacept therapy, tocilizumab therapy, sarilumab therapy, or satralizumab therapy.

In embodiments, provided herein is a method of treating a subject receiving a therapy comprising administration of a pharmaceutical composition, the method including (a) detecting an HLA-DRB1*15 allele in a biological sample received from said subject receiving said therapy; and (b) discontinuing said therapy, administering an altered dose of said pharmaceutical composition to said subject in place of said pharmaceutical composition.

In embodiments, provided herein is a method of treating a subject in need of a therapy comprising administration of a pharmaceutical composition, the method including (a) detecting an HLA-DRB1*15 allele in a biological sample received from said subject in need of said therapy; and (b) administering a pharmaceutical composition alternative to the subject.

In embodiments, provided herein is a method of identifying a subject at risk of hypersensitivity related to a therapy comprising administration of a pharmaceutical composition, the method including detecting an HLA-DRB1*15 allele in a biological sample received from the subject.

In embodiments, provided herein is a method of determining whether a subject is at risk of hypersensitivity related to a therapy comprising administration of a pharmaceutical composition, the method including determining whether an HLA-DRB1*15 allele is present in a biological sample received from said subject, wherein the presence of the HLA-DRB1*15 allele in the biological sample indicates said subject is at risk of hypersensitivity related to the therapy.

In embodiments, provided herein is a method of analyzing a biological sample received from a subject receiving a therapy comprising administration of a pharmaceutical composition, the method comprising detecting an HLA-DRB1*15 allele in the biological sample received from said subject receiving said therapy.

In embodiments, provided herein is a method of analyzing a biological sample received from a subject in need of a therapy comprising administration of a pharmaceutical composition, the method comprising detecting an HLA-DRB1*15 allele in said biological sample received from said subject in need of said therapy.

In embodiments, provided herein is a method for preparing a deoxyribonucleic acid (DNA) fraction from a subject receiving a therapy comprising administration of a pharmaceutical composition wherein said DNA fraction is useful for genotyping, the method including (a) extracting DNA from a biological sample from said subject receiving said therapy; (b) producing a fraction of the DNA extracted in (a) thereby producing a DNA fraction; and (c) determining whether said DNA fraction comprises an HLA-DRB1*15 allele.

In embodiments, provided herein is a method for preparing a deoxyribonucleic acid (DNA) fraction from a subject in need of a therapy comprising administration of a pharmaceutical composition wherein said DNA fraction is useful for genotyping, the method including (a) extracting DNA from a biological sample from said subject in need of said therapy; (b) producing a fraction of the DNA extracted in (a) thereby producing a DNA fraction; and (c) determining whether said DNA fraction comprises an HLA-DRB1*15 allele.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Introduction to Exemplary Experiments

Applicants recently described systemic JIA patients who developed a high-fatality diffuse lung disease (DLD) while on IL-1 or IL-6 inhibitors. Severe, drug-related delayed hypersensitivity reactions (DHR) were observed in a significant subset. Because alleles of the human leukocyte antigen (HLA) loci can mediate DHR, Applicants investigated HLA genotype association with these DHR. Applicants typed subjects treated with these inhibitors: 34 sJIA/DHR/DLD, 11 sJIA/DHR without DLD, 18 drug-tolerant sJIA, and 19 Kawasaki disease (KD) patients in an anti-IL-1(anakinra) trial. Genotypes from a large sJIA case/control cohort were also accessed.

Applicants first compared White subjects with sJIA/DHR to 550 ancestry-matched sJIA subjects. Striking enrichments of HLA-DRB1*15:01, HLA-DQA1*01:02, and DQB1*06:02, alleles in near-complete linkage (White individuals) were found. HLA-DRB1*15:01 (as haplotype proxy) was increased in White sJIA subjects with DHR/DLD versus sJIA drug-tolerant controls and was observed upon inclusion of sJIA+DHR-only and KD+DHR White subjects. In the entire cohort regardless of ancestry, 75% carried HLA-DRB1*15:01 or the structurally related DRB1*15:03 and DRB1*15:06, which were absent among drug-tolerant subjects ($p=5\times10^{-13}$; Odds Ratio lower bound=20.11).

Patients who harbor HLA-DRB1*15 alleles are at high risk of developing DHR related to anti-IL-1/IL-6. Applicants' data also suggest DHR maybe a trigger/enhancer of DLD in sJIA patients and support performing prospective HLA screening in sJIA, its adult-onset counterpart, and other inflammatory conditions where these drugs are used, such as KD.

Example 2: Hypersensitivity Reactions to IL-1 and IL-6 Inhibitors are Linked to Common HLA-DRB1*15 Alleles Severe delayed hypersensitivity reactions (DHR) are observed in association with various drugs that are otherwise highly efficacious. Particular human leukocyte antigen (HLA) class I and/or class II alleles are associated with DHR risk for particular drugs, allowing screening of patients to inform clinical decision making.

Figure 1B:
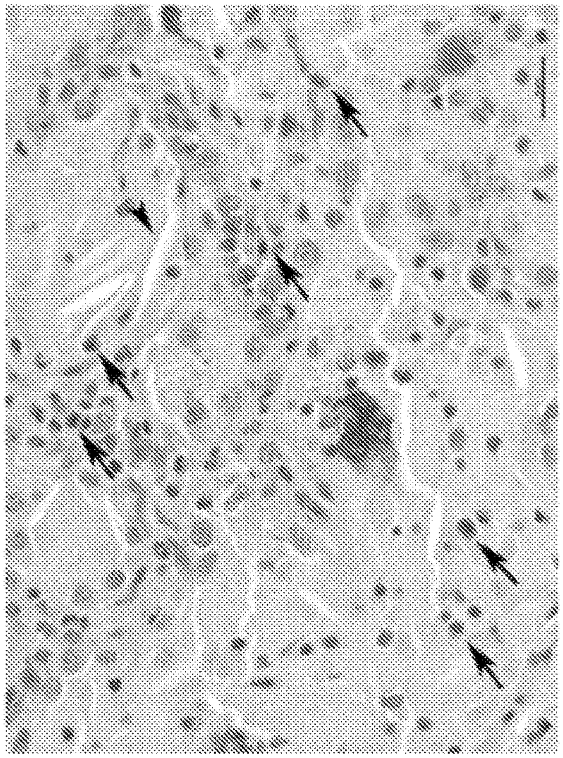
FIG. 1A-1H Clinical features in cases with delayed hypersensitivity reaction (DHR).
Figure 1A:
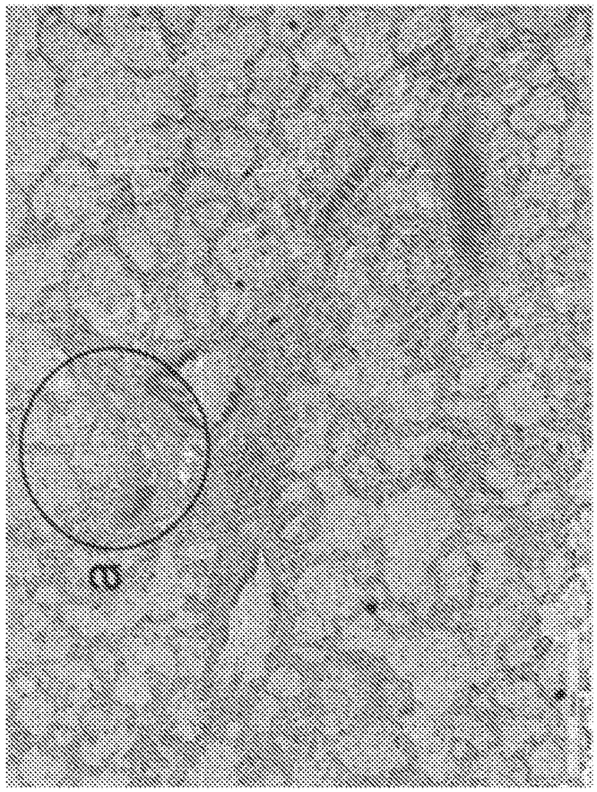
Figure 1D:
Figure 1C:
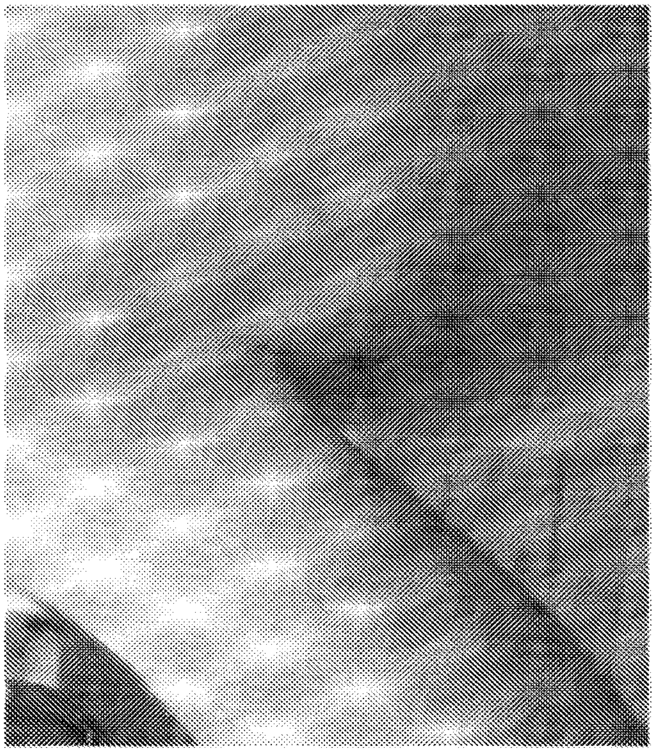
Figure 1F:
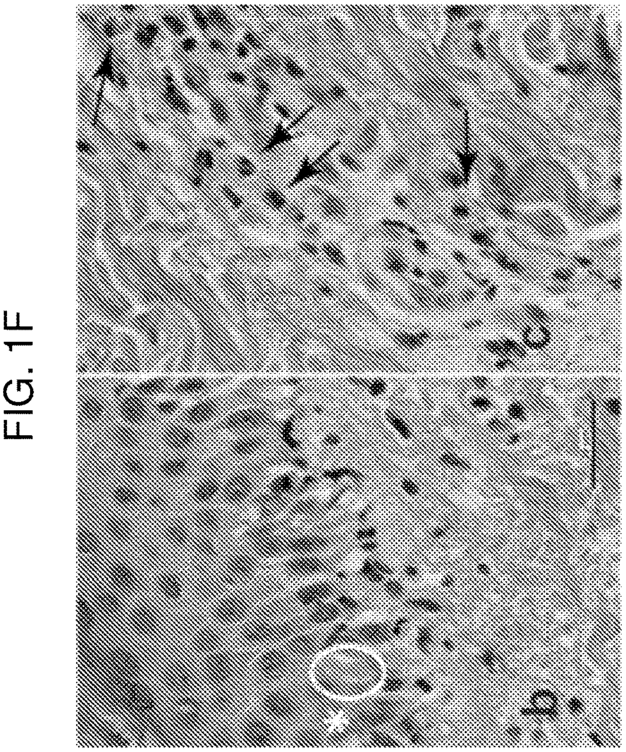
Figure 1E:
Figure 1H:
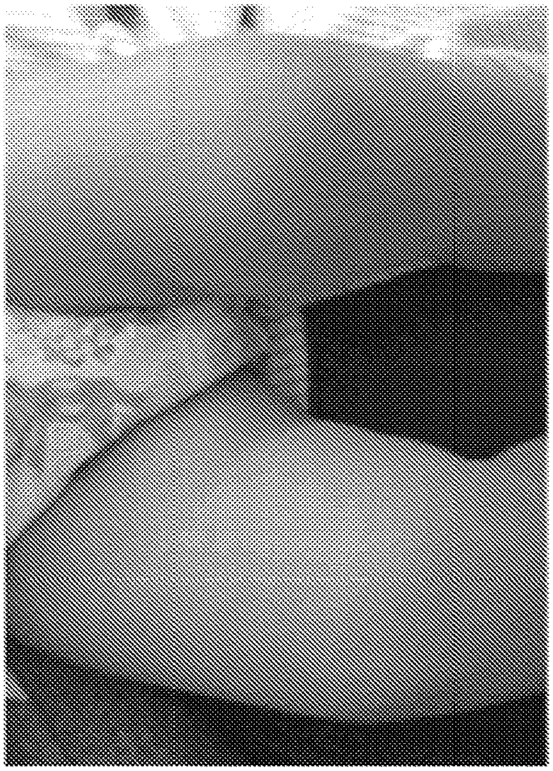
Figure 1G:
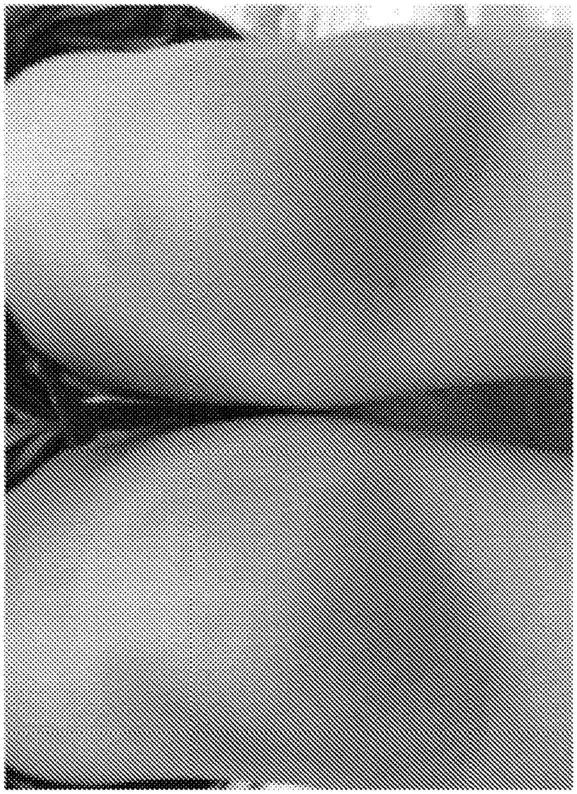
Figure 2B:
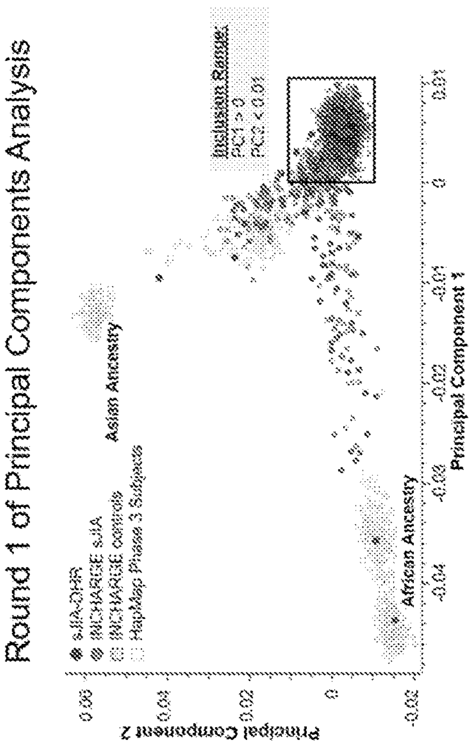
FIGS. 2A-2D Ancestral matching of INCHARGE sJIA GWAS cases and controls with sJIA-DHR subjects by principal component analysis.
Figure 2A:
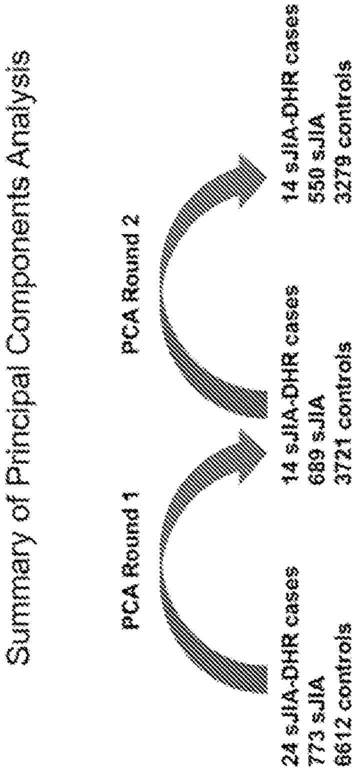
Figure 2D:
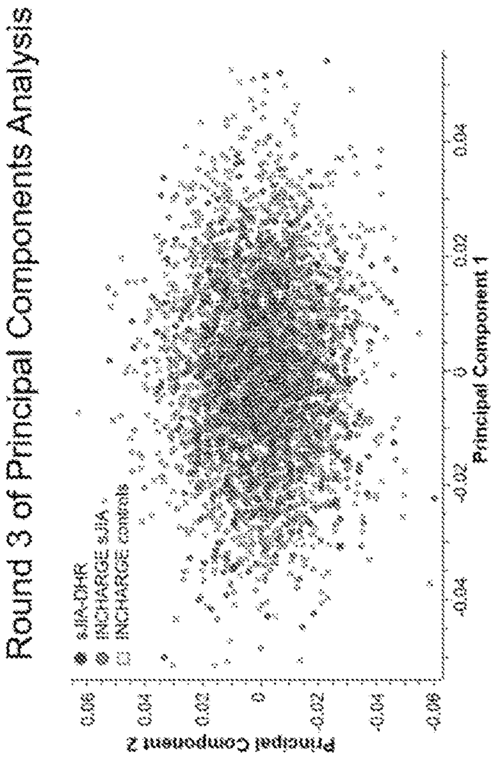
Figure 2C:
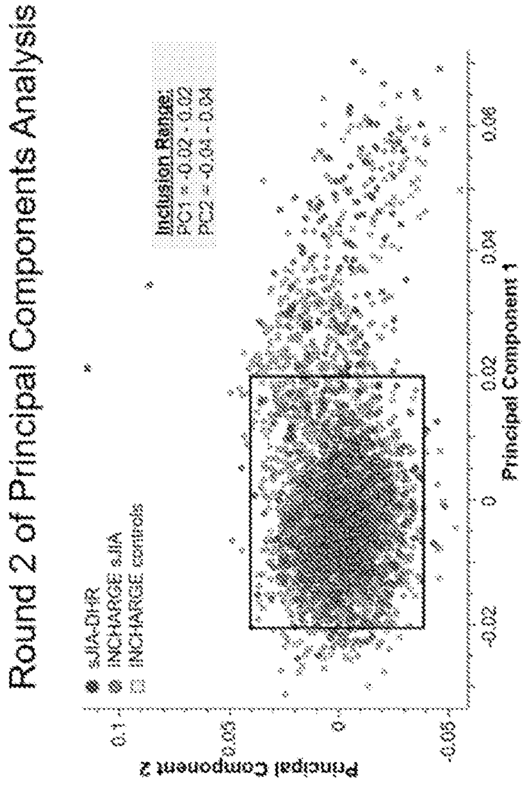
Figure 3A:
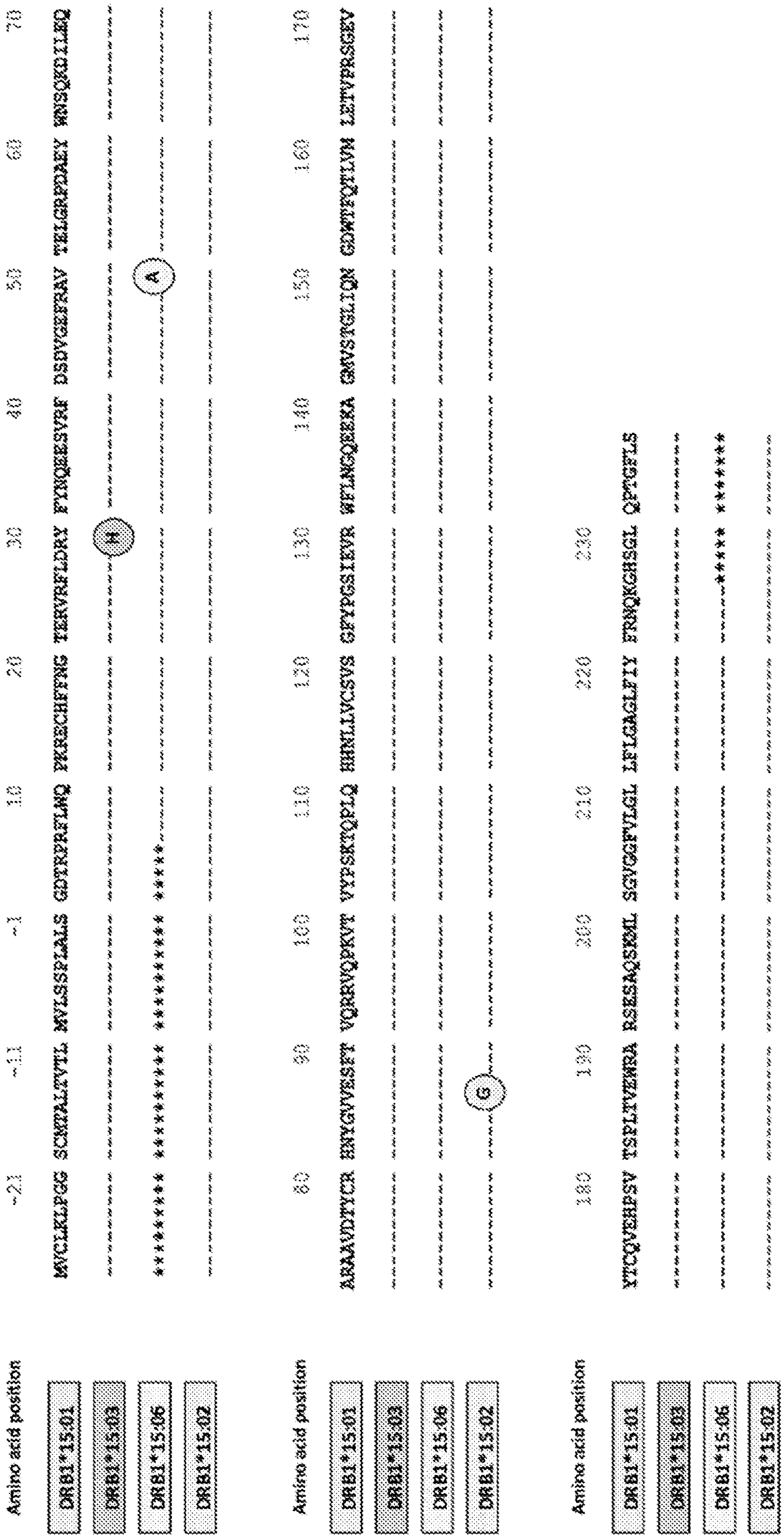
Figure 3C:
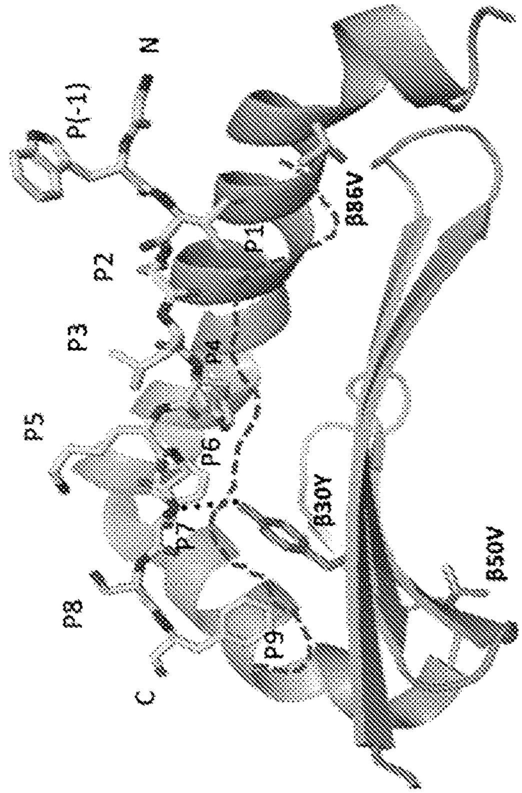
Figure 3B:
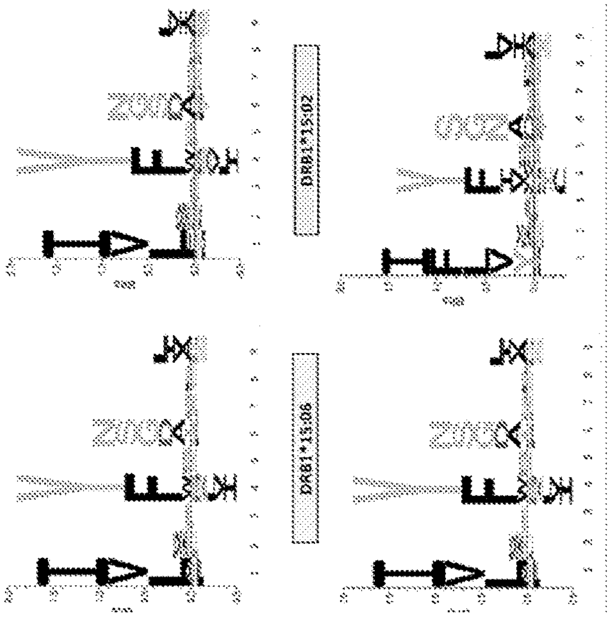

As described herein, the present inventors observed drug reaction and eosinophilic systemic syndrome (DRESS), a form of DHR, in patients with Still's disease receiving IL-1 or IL-6 inhibitor therapy, complicated by a novel, parenchymal, diffuse lung disease (DLD). The term "Still's disease" includes the full age continuum of systemic juvenile idiopathic arthritis (sJIA) and adult onset Still's disease (AOSD). Although the term "sJIA" is used below, the cohort included both sJIA and AOSD patients. Therefore, the data described herein should be understood as encompassing the lung pathology as a variant of pulmonary alveolar proteinosis (FIGS. 1A and 1B), and DHR features included rashes (FIGS. 1C-1H) and eosinophilia. The associated drugs were IL-1 and IL-6 inhibitors. To determine whether risk of this drug-related DHR was HLA-associated, Applicants accessed genotypes from a large, multi-ethnic Still's case/control cohort and from 34 sJIA subjects with DLD/DHR, 11 with DHR without DLD, and 18 carefully screened, drug-tolerant sJIA controls. Methods, ancestry/HLA data (Tables 3 and 4) and additional information on clinical features (Tables 5 and 6) are provided herein.

Applicants first compared White subjects in the sJIA/DHR/DLD subgroup to 550 ancestry-matched sJIA subjects without known DLD and to 3279 ancestry-matched healthy controls. Conspicuous enrichments for HLA-DRB1*15:01, HLA-DQA1*01:02 and HLA-DQB1*06:02 (Table 1A), alleles in near-complete linkage in White individuals were found. Using White sJIA/all-DHR cases increased this haplotype-associated risk, linking it to DHR, as opposed to DLD. As expected, HLA-DRB1*11/HLA-DQB1*03:01, the sJIA-associated haplotype, was present in sJIA cases with and without DHR (Table 7).

Using HLA-DRB1**15:01 as a haplotype proxy, Applicants found a high frequency (75%) of this allele in White sJIA subjects with DHR with or without DLD vs 0% in drug-tolerant controls (Table 1B). To determine whether HLA-linked DHR required Still's-specific immune dysfunction, Applicants studied a small cohort (n=19) of children with Kawasaki disease (KD) in a Phase I/IIa trial of anakinra. Including White KD subjects with/without suspected anakinra reaction (sAR) yielded the same striking results (Table 1B).

The addition of Non-White cases provided 49 subjects with DHR, of which a remarkable 37 carried HLA-DRB1*15:01 or the closely related *15:03 and *15:06; this allelic group was completely absent among drug-tolerant controls (Table 1B). Notably, HLA-DRB1*15:02, which differs from HLA-DRB1*15:01 by one amino acid that influences peptide-binding (FIG. 6), was not associated with DHR. Analysis of the sJIA-DHR/KD-sAR group across ancestries, where patterns of linkage disequilibrium differ, suggested the operative locus is HLA-DRB1 or HLA-DRB5, as Applicants find reduced effect for alleles at other loci on this haplotype (Table 1B).

Figure 5:
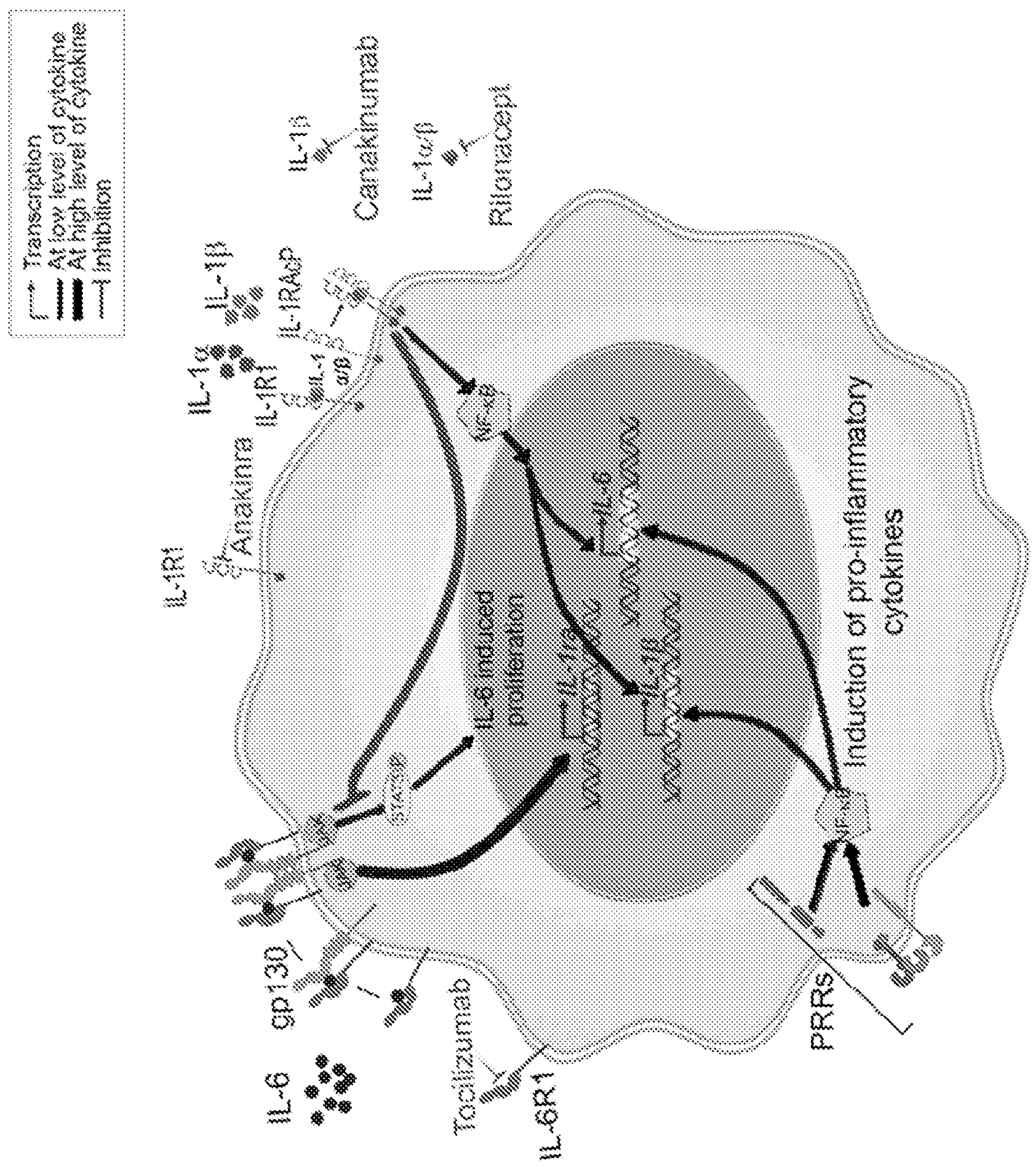
FIG. 5 Cross-talk between IL-1 and IL-6 pathways in inflammation. This diagram reflects the interdependence of cytokines IL-1 and IL-6 and their cross-talk during an immune response. Cells detect infection or other inflammatory signals by extracellular (Toll-like receptor, Dectin1) or intracellular (NOD-like receptor) pathogen recognition receptors (PRR) and induce production of inflammatory cytokines including IL-1 beta, IL-6 in an NF-κB dependent pathway. IL-6 binds to IL-6 receptor 1 (IL-6R1) and gp130 to activate JAK/STAT3 pathway, which regulates immune responses and cell homeostasis. At higher concentrations, IL-6 also induces expression of IL-1 receptor antagonist (IL-1RA), blocking IL-1 biological activities. IL-1 (α/β) binds to IL-1R1 and IL-1 receptor accessory protein (IL-1RAcP) to promote expression of pro-inflammatory cytokines in an NF-κB dependent pathway. At higher concentrations, IL-1 blocks the IL-6 mediated JAK/STAT3 pathway). At lower concentrations, IL-1 and IL-6 promote inflammation, whereas at higher concentrations they suppress each other's activities. With pre-existing inflammation, including elevated IL-6, signaling through pattern recognition receptors (PRR) induces higher IL-1 beta release and inhibits IL-1RA secretion, promoting the inflammation. Treatment of inflammatory conditions with specific inhibitors reduces the activity of these cytokines in an interdependent way.

An unusual aspect of this DHR/HLA association is that the risk spans several inhibitors with different chemical structures (FIG. 4). These findings raise the possibility that an excipient common to these drugs and/or a molecule increased by inhibition of the IL-1/IL-6 network (FIG. 5) creates a stimulatory HLA class II molecule, which activates CD4+ T cells. The immune dysregulation in sJIA and KD likely underlies the failure to restrain this T cell response, possibly compounded by the effects of the drugs.

Applicants' findings highlight the need for surveillance for DReSS associated with IL-1/IL-6 inhibitors, which is often missed, especially when it occurs during active systemic inflammatory disease. Importantly, DHR in sJIA may initiate or substantially contribute to DLD (Table 5). Carriers of the risk alleles are common [27% (White), 15% (Hispanic), 27% (Black) and 16% (Asians) in US populations]. Results described herein argue for consideration of prospective HLA screening in sJIA and its adult-onset counterpart. For other emergent inflammatory conditions for which these drugs are used, including COVID-19 and MIS-C, eosinophil and atypical lymphocyte counts should be monitored.

Example 3: Materials and Methods

HLA genotypic data was collected on a total of 82 subjects from 31 institutions. The subjects fell into 4 diagnostic subgroups. 28 subjects had the combination of systemic juvenile idiopathic arthritis (sJIA), diffuse lung disease (DLD) and delayed hypersensitivity reaction (DHR) to one or more of anakinra, canakinumab, rilonacept and tocilizumab used as treatment in sJIA. These patients met an operational sJIA case definition, developed by expert consensus as a modification of the ILAR (International League of Associations for Rheumatology) sJIA classification criteria. In addition, 5 subjects with the combination of sJIA-like disease (managed clinically like sJIA, but not meeting modified ILAR criteria), DLD and DHR were added to this group, as was 1 subject with DLD, DHR and adult onset Still's disease (AOSD), the adult counterpart of sJIA. 10 sJIA patients and 1 sJIA-like patient, all with DHR related to IL-1 or IL-6 inhibitors but without DLD, comprised the second subgroup. sJIA patients in the third subgroup were drug-tolerant greater than 1 year on IL-1 or IL-6 inhibitors and lacked DLD. The fourth subgroup, (n=19) met American Heart Association criteria for KD. In the KD trial, anakinra doses ranged from 2 to 8 mg/kg/day. Patients were treated with daily subcutaneous injections for two weeks and then re-evaluated by echocardiogram. If the aneurysms were persistent, then treatment was continued for an additional 4 weeks for a total duration of 6 weeks. Ancestry data were provided by case reporters based on parents' response and then selection from a list of categories (White, Black, Latinx, Asian, South Asian, Middle Eastern, noting mixed parentage).

Demographic data, including ancestry for all 82 subjects, are shown on Tables 3-6. For some analyses, comparator populations were sJIA cases without known lung disease and healthy control subjects (both previously genotyped) from the International Childhood Arthritis Genetics Consortium (INCHARGE) genome-wide association study.

Clinical Data Collection

Clinical information on the majority of sJIA subjects was collected using REDCap electronic capture tools, hosted at Stanford University or by direct communication with the physician case reporter; for patients evaluated at the NIH, data were collected and extracted using the NIH Clinical Trials Database (CTDB). The diagnosis of delayed drug hypersensitivity reaction (DHR) in sJIA subjects was based on physician determination at the treating institution or on classification as definite or probable drug reaction with eosinophilia and systemic syndrome (DReSS), using the validated RegiSCAR for DRESS. sJIA or AOSD drug-tolerant controls had experienced uneventful treatment with anti-IL-1/anti-IL-6 for ≥1 year and discontinued steroids during this treatment or experienced ≥6 weeks of steroid dose of <0.2 mg/kg/day. sJIA controls were classified clinically as drug tolerant prior to determining HLA. A KD case of suspected anakinra reaction (KD-sAR) was defined by development of eosinophilia during treatment with anakinra compared with study baseline. Inclusion required an absolute eosinophil count (AEC) ≥500 with an increase of ≥50% over pre-treatment value at study baseline. Eosinophilia was required since KD subjects were not steroid treated during anakinra. Atypical lymphocytes and rash consistent with drug eruption were considered supportive if present. Further data for RegiSCAR scoring was unavailable. KD drug-tolerant controls were those exposed to anakinra without developing eosinophilia. Subjects were sorted into cases or controls, by a board-certified allergist (VS), prior to determination of HLA. In Table 3 (cases), IL-1 or IL-6 inhibitors implicated as associated with DHR are listed (DHR). In Table 4 (controls), any inhibitor used is indicated (drug exposure).

Diffuse lung disease (DLD) required either lung tissue diagnosis of variant pulmonary alveolar proteinosis/endogenous lipoid pneumonia (vPAP/ELP) or diffuse bilateral pulmonary interstitial abnormalities on chest CT, both as previously described. Cases were categorized as DHR/DLD if DLD developed during the course of drug treatment. Among 46 previously reported sJIA cases with lung disease after drug clinical data gathered from the time of drug institution until the recognition of lung disease confirms that all 19 with available genetic information are DHR/DLD and are included in this analysis. Clinical data are shown on Tables 5 and 6.

Histologic Evaluation

In cases in which lung pathology (biopsy or autopsy) was available for analysis by a pediatric pulmonary pathologist (GD) (n=16), hematoxylin and eosin (H&E) slides were reviewed and major histologic features were assessed. All cases demonstrated the histologic pattern of vPAP/ELP characterized by alveolar filling with eosinophilic proteinaceous material admixed with a variable degree of cholesterol clefts and foamy macrophages. Some degree of inflammation (neutrophils, lymphocytes, plasma cells, eosinophils) was frequently present as well as wall thickening of pulmonary arteries. A semi quantitative grading scale was used to assess the number of eosinophils on H&E stain at ×20 magnification; at least 10 fields assessed. Zero=no eosinophils, 1=scattered eosinophils in few fields, 2=scattered eosinophils in many fields with rare aggregates, 3=scattered eosinophils in most fields with several aggregates, 4=numerous aggregates of eosinophils. 3 cases were graded 0; 5 cases at 1; 8 cases at 2-3. All subjects with tissue graded 0 were on high dose (1-2 mg/kg/day) steroids (not shown).

DNA Extraction Methods

Different DNA extraction methods were used, as follows. Genomic DNA (gDNA) was extracted from peripheral blood samples of subjects recruited at Stanford University using the QIAsymphony DNA Mini Kit (based on silica matrix solid-phase purification) automated protocol and performed according to the manufacturer's instructions (Qiagen, Hilden, Germany). For subjects recruited at the NIH, gDNA was extracted from peripheral blood samples using the Maxwell 16 DNA Purification Kits and the automated Maxwell 16 instrument, according to manufacturer's instructions (Promega, Madison, WI, United States). For the patients with Kawasaki disease, gDNA was extracted from peripheral blood samples using the Wizard Genomic DNA purification kit following the manufacturer's instructions (Promega, Madison, WI, USA). In the case of formalin-fixed paraffin-embedded (FFPE) samples, gDNA was extracted using the QIAamp DNA FFPE tissue kit (Qiagen, Hilden, Germany) following the Stanford Molecular Pathology laboratory's standard protocol. Quantity and quality of extracted DNA samples were either measured by spectrophotometry using the NanoDrop 2000 instrument (Thermo Fisher Scientific, Waltham, MA, USA) or by fluorometric quantification of double-stranded DNA using a Qubit 3 instrument (Thermo-Fisher Scientific, Waltham, MA, USA).

HLA Genotyping

HLA Genotyping Via Next-Generation Sequencing (NGS)

DNA samples were typed for HLA class I (HLA-A, HLA-B and HLA-C) and class II (HLA-DPA1, HLA-DPB1, HLA-DQA1, HLA-DQB1, HLA-DRB1, HLA-DRB3, HLA-DRB4, and HLA-DRB5) loci using the MIA FORA NGS FLEX high-throughput semi-automated typing protocol (Immucor, Inc., Norcross, GA, USA) and performed following the manufacturer's instructions. This NGS method allowed full-length coverage for HLA class I genes and extensive coverage for class II genes amplified by long range PCR. After DNA library preparation steps, pooled sample libraries were sequenced at a final concentration of 1.3 pM spiked with 20 pM PhiX on the Illumina MiniSeq instrument using 150 cycle paired-end kits (Illumina, Inc., San Diego, CA). NGS sequencing reads stored as .fastq files were uploaded into the MIA FORA NGS FLEX v4.5 HLA genotyping software (Immucor, Norcross, GA) for: building phased consensus sequences; establishing their respective alignment to reference sequences (according to IPD-IMGT/HLA v3.36.0 database, and, in addition, to MIA FORA FLEX internal reference database of cloned and in-silico HLA allele sequences).

HLA Genotyping Via Reverse Sequence-Specific Oligonucleotide (rSSO) DNA Typing Method As an alternative to NGS HLA typing method, some extracted DNA samples were tested for HLA-DQA1, HLA-DQB1, HLA-DRB1, HLA-DRB3, HLA-DRB4, and HLA-DRB5 loci via reverse sequence-specific oligonucleotide (rSSO) DNA typing method using the LABType SSO HLA semi-automated typing protocol (One Lambda, Inc., Canoga Park, CA) and following the manufacturer's instructions. HLA genotyping data obtained by rSSO was according to IPD-IMGT/HLA v3.37.0 release database.

HLA Genotyping from WES Data 36 subjects had whole exome sequencing (WES) data from which HLA genotype was extracted. WES data from 14 subjects were analyzed at Stanford using HLAreporter. In brief, a preliminary high-efficiency mapping of the reads was achieved using Burrows-Wheeler Aligner (BWA) against a comprehensive reference panel generated from all known HLA alleles in the IMGT/HLA database followed by a de novo assembly of gene-specific mapped reads to contigs using Targeted Assembly of Short Sequence Reads (TASR). Typically, contigs with an average coverage-depth of ≥5-fold were picked for HLA allele assignment. Subsequently, these contigs were matched stepwise against reference databases of HLA alleles, followed by HLA allele calling for HLA-A, -B, -C, -DRB1, -DRB3/4/5, -DQA1, -DQB1, -DPB1. Similarly, WES data from 21 subjects were analyzed at the NIH using HLA:LA, a highly accurate graph-based method for extracting HLA alleles from exome and low-coverage whole genome sequencing data. Briefly, input reads were linearly aligned to Population Reference Graph (PRG) reference haplotypes, which include eight GRCh38 MHC haplotypes and all IMGT exonic and genomic sequences, using BWA-MEM. Linear alignments were projected onto the PRG and the alignments were optimized in a stepwise process. Contigs overlapping the MHC were identified using nucmer, and each contig was annotated according to the HLA haplotype with the highest alignment score. HLA sequences were extracted according to genomic position, and HLA typing was performed by minimum edit distance-based matching with the IMGT database. Three subjects were analyzed at both Stanford and the NIH, with identical results. WES data from 1 subject and both parents were analyzed at The Children's Hospital of Philadelphia (DM) using Explore (Omixon, Budapest, Hungary). Briefly, the fastq files were filtered in Explore for reads deriving from 35 HLA genes/pseudogenes within the MHC (HLA-A, B, C, DMA, DMB, DOA, DOB, DPA1, DPA2, DPB1, DPB2, DQA1, DQB1, DRA, DRB1, DRB2, DRB3, DRB4, DRB5, DRB6, DRB7, DRB8, DRB9, E, F, G, H, J, K, L, T, U, V, W, Y). The filtered reads were then analyzed using Explore, targeting the same panel of MHC genes using both an exon-only and full gene analysis modes. Genotype data was reported for classical HLA loci (HLA-A, B, C, DPA1, DPB1, DQA1, DQB1, DRB1, DRB3, DRB4, and DRB5). Discrepancies between the two methods were resolved manually. Haplotype analysis of the trio confirmed the genotype of the patient. All analysis was conducted using the IMGT/HLA database version 3.38.0. For subjects from the INCHARGE sJIA GWAS cohort, HLA alleles at the 8 classical HLA loci were determined by HLA imputation with SNP2HLA software.

Data Analysis

Association testing of HLA alleles with INCHARGE sJL4 GWAS cohort: To test the hypothesis that one or more HLA alleles was associated with a hypersensitivity reaction in a subset of drug-exposed sJIA patients (sJIA-DHR), Applicants compared the prevalence of HLA alleles in subjects with sJIA-DHR to those of subjects with sJIA, overall. To do this, Applicants utilized the largest available sJIA cohort, the INCHARGE sJIA case-control collection genetic architecture]. sJIA cases and healthy controls from the INCHARGE collection matching the genetic ancestry of the sJIA-DHR subjects were identified and selected using a principal component analysis (PCA)-based approach with SNP & Variation Suite 8 (SVS8; Golden Helix, Bozeman, MT, USA), as previously described. Briefly, SNP genotype data from 1) the full INCHARGE cohort, 2) the HapMap phase 3 reference populations and 3) the subset of sJIA-DLD/DHR subjects with whole exome sequence WES data were combined. The intersecting set of SNPs were filtered to exclude linkage disequilibrium ($r^2<0.3$) and SNPs with minor allele frequency below 0.05. Principal components (PCs) were calculated for the resultant set of SNPs and visual inspection of PC plots was used to identify and exclude ancestral outliers. This produced a tight cluster of INCHARGE sJIA cases (n=550) and control subjects (n=3279), together with every subject of self-reported European ancestry from sJIA-DHR group (14 sJIA-DHR, 12 with DLD/DHR). Genomic control inflation factors (lGC) were calculated, ranging between 1.000 and 1.05, demonstrating that these groups were genetically well-matched to both the INCHARGE sJIA cases and healthy control subjects. Association testing by logistic regression was carried out in SVS8 using numerically encoded HLA alleles under the dominant model in both the sJIA-DHR/DLD (n=12) and sJIA-DHR (n=14) subsets (FIG. 7A).

Ten additional sJIA-DHR subjects of self-reported European ancestry, including 6 with DLD, lacked SNP or sequencing data and were not included in the ancestral matching process. Given the perfect concordance of self-reported European/White ancestry with cluster membership among the group evaluated by PCA, Applicants added these 10 sJIA-DHR subjects of "self-reported white" ancestry to the case groups and repeated association testing by logistic regression in the sJIA-DHR/DLD group (n=18) and the sJIA-DHR group (n=24). Finally, Applicants removed the ancestral restriction from the analysis and used association testing by logistic regression to compare all subjects with sJIA-DHR (n=45) to the full set of sJIA cases (n=773) or controls (n=6812) from the INCHARGE GWAS. Association testing results were corrected for multiple comparisons (p=0.05/163 HLA alleles tested for association), leading Applicants to define a statistically significant association in this analysis as p<3.07E-04. The results of logistic regression were expressed as beta coefficients, from which odds ratios and 95% confidence intervals were derived.

Association testing of HLA-DRB1*15:01 in drug-treated patients: To examine the a priori assumption that HLA-DRB1*15:01 is associated with a hypersensitivity reaction in drug-treated patients, Applicants employed a 2×2 contingency table using Fisher's exact test. All analyses were conducted in the R environment for statistical computing and p-values and odds ratios with 95% confidence intervals were obtained using the 'epitools' package. The analysis considered three primary comparisons: 1) sJIA-DHR/DLD vs. drug tolerant sJIA patients treated with drug with no DHR; 2) all sJIA-DHR (with or without DLD) vs. sJIA patients treated with drug with no DHR; and 3) all sJIA and KD patients with DHR vs. drug tolerant sJIA and KD patients treated with drug with no DHR. Each of these three analyses was conducted in two overlapping cohorts: First, only in patients who self-identified as White/European ancestry, and second, in all patients regardless of self-identification. Additionally, Applicants tested for association of drug reaction in all patients (sJIA and KD) and across all ancestries with alleles commonly associated with the HLA-DRB1*15:01 haplotype: HLA-DQA1*01:02; HLA-DQB1*06:02. Because these alleles are in complete linkage disequilibrium (LD) in White subjects, analysis across diverse ancestral groups, where patterns of LD are observed to break down, serve to identify the causative locus.

TABLES 1A and 1B

HLA class II associations with delayed drug hypersensitivity related to IL-1 and IL-6 inhibitors

| Comparison | | | | | | | | |
|---|---|---|---|---|---|---|---|---|
| Case | Control | Ancestry | HLA allele[1] | Case n(%) | Control n(%) | P value | OR | 95% CI |
| Table 1A. | | | | | | | | |
| sJIA-DHR/DLD[2] | INCHARGE sJIA[3] | European | HLA-DRB1*15:01 | 11/12 (92%) | 130/550 (24%) | 7.0E−07 | 36 | 4.5-277.9 |
| | | | HLA-DQB1*06:02 | 11/12 (92%) | 128/550 (23%) | 6.0E−07 | 36 | 4.6-283.6 |
| | | | HLA-DQA1*01:02 | 11/12 (92%) | 188/550 (34%) | 3.0E−05 | 21 | 2.7-165.3 |
| sJIA: all DHR[5] | | | HLA-DRB1*15:01 | 13/14 (93%) | 130/550 (24%) | 4.0E−08 | 42 | 5.4-324.1 |
| | | | HLA-DQB1*06:02 | 13/14 (93%) | 128/550 (23%) | 4.0E−08 | 43 | 5.6-330.8 |
| | | | HLA-DQA1*01:02 | 13/14 (93%) | 188/550 (34%) | 5.0E−06 | 25 | 3.2-192.8 |
| Table 1B. | | | | | | | | |
| sJIA-DHR/DLD | drug tolerant sJIA[6] | White/ European[7] | HLA-DRB1*15:01 | 14/18 (78%) | 0/11 (0%) | 5.0E−05 | Inf | 5.21-Inf |
| sJIA: all DHR | drug tolerant sJIA | | HLA-DRB1*15:01 | 18/24 (75%) | 0/11 (0%) | 3.0E−05 | Inf | 5.12-Inf |
| sJIA-DHR + KD-sAR[8] | drug tolerant sJIA + KD[9] | | HLA-DRB1*15:01 | 19/26 (73%) | 0/12 (0%) | 2.0E−05 | Inf | 5.32-Inf |
| sJIA-DHR/DLD | drug tolerant sJIA | All[10] | HLA-DRB1*15:XX[11] | 26/34 (76%) | 0/18 (0%) | 4.0E−08 | Inf | 10.45-Inf |
| sJIA: all DHR | drug tolerant sJIA | | HLA-DRB1*15:XX | 34/45 (76%) | 0/18 (0%) | 1.0E−08 | Inf | 10.69-Inf |
| sJIA-DHR + KD-sAR | drug tolerant sJIA + KD | | HLA-DRB1*15:XX | 37/49 (76%) | 0/33 (0%) | 3.0E−13 | Inf | 20.70-Inf |
| | | | HLA-DRB5*01:01 | 25/31 (80%) | 1/27 (4%) | 9.0E−10 | 95.41 | 11.7-4460.5 |
| | | | HLA-DQB1*06:02 | 34/49 (69%) | 1/33 (3%) | 2.0E−10 | 73.12 | 10.3-3189.8 |
| | | | HLA-DQA1*01:02 | 37/47 (79%) | 7/33 (21%) | 3.0E−07 | 13.16 | 4.14-47.65 |

OR, odds ratio;
95% CI, 95% confidence interval;
sJIA, systemic juvenile idiopathic arthritis;
KD: Kawasaki disease;
DHR: delayed hypersensitivity reaction;
diffuse lung disease (DLD);
sAR; suspected anakinra reaction (delayed type, not anaphylaxis);
[1]HLA class I typing was also done on a large proportion of the subjects, but did not show any independent associations (not shown);
[2]sJIA-DHR/DLD: cases with sJIA, delayed hypersensitivity reaction (DHR) and diffuse lung disease (DLD);
[3]INCHARGE sJIA: sJIA cases without known lung disease from the International Childhood Arthritis Genetics Consortium (INCHARGE) genome-wide association study;
[4]European ancestry, matched by principal component analysis (see Methods and FIG.s 2A-2D);
[5]JIA with DHR, with and without DLD; significant: After correction for multiple comparisons, a statistically significant association in part A is $p < 3.07E-04$;
[6]Drug tolerant sJIA: sJIA controls with ≥1 year of uneventful exposure to IL-1/IL-6 inhibitors;
[7]Self-identified ancestry;
[8]sJIA with DHR, with and without DLD, plus KD with suspected anakinra reaction (sAR);
[9]sJIA controls with ≥1 year of uneventful exposure to IL-1/IL-6 inhibitors and KD controls without features of DHR during anakinra;
[10]All subjects, regardless of self-identified ancestry;
[11]HLA-DRB1*15:01 + HLA-DRB1*15:03 + HLA-DRB1*15:06.

TABLE 2

| Definitions of ancestry groups Ancestry groups | |
|---|---|
| Group | Definition |
| White | Self-identification as White or White European |
| Middle Eastern | Egypt, Oman, Yemen, Qatar, United Arab Emirates, Iran, Bahrain, Syria, Jordan, Turkey, Lebanon, Saudi Arabia, Kuwait, Iraq, Israel |
| Hispanic | Self-identification as Hispanic, Latinx, Central or South American |
| South Asian | Afghanistan, India, Pakistan, Bangladesh, Sri Lanka, Nepal, Bhutan, Maldives |
| Asian | Central, Northern, Eastern, Western and South Eastern Asia |
| Black | Self-identification as Black or Black-African |

In Tables 3, 4, 5 and 6, sections with data on cases are indicated by a bold number (n) and those with data on controls are indicated by a bold italicized number (n). For Tables 3 and 5, footnotes are provided on the page following the table.

TABLE 3

| HLA-DQ and -DR in cases with delayed hypersensitivity reaction (DHR) | | | | | | |
|---|---|---|---|---|---|---|
| n | Ancestry1 | DQA1 | DQB1 | DRB1 | DRB3/4/5/Absent2 | DHR3, 4 |
| Cases with DHR and diffuse lung disease (DLD) developing during treatment (sJIA-DHR/DLD) | | | | | | |
| 1 | White | *01:02/*01:02 | *06:02/*06:04 | *15:01/*13:02 | DRB5*01:01/DRB3*03:01 | A |
| 2 | White | *01:02/*05:01 | *06:02/*03:01 | *15:01/*11:04 | DRB5*01:01/DRB3*02:02 | A T |
| 3 | White | *05:01/*05:01 | *02:01/*03:01 | *03:01/*11:01 | nd | A |
| 4 | White | *01:02/*01:02 | *06:02/*06:02 | *15:01/*15:01 | DRB5*01:01/DRB5*01:01 | A |
| 5 | White | *01:02/*05:01 | *06:02/*03:01 | *15:01/*11:01 | DRB5*01:01/DRB3*03:02 | A |
| 6 | White | *01:02/*05:01 | *06:02/*03:01 | *15:01/*12:01 | DRB5*01:01/DRB3*02:11 | A |
| 7 | White | *01:02/*01:02 | *06:02/*06:02 | *15:01/*15:01 | DRB5*01:01/DRB5*01:01 | A C |
| 8 | White | *01:01/*05:05 | *03:01/*05:01 | *01:02/*11:06 | nd | A |
| 9 | White | *01:02/*05:05 | *06:02/*03:01 | *15:01/*13:03 | nd[5] | A |
| 10 | White | *01:02/*01:02 | *06:02/*06:02 | *15:01/*15:01 | nd[5] | A C |
| 11 | White | *01:02/*01:02 | *06:02/*06:02 | *15:01/*15:01 | DRB5*01:01/DRB5*01:01 | T |
| 12 | White | *01:02/*01:02 | *06:02/*06:02 | *15:01/*15:01 | DRB5*01:01/DRB5*01:01 | A (probable) |
| 13 | White | *01:02/*05:01 | *06:02/*03:01 | *15:01/*13:03 | DRB5*01:01/DRB3*01:01 | T |
| 14 | White | *01:02/*05:01 | *06:02/*03:01 | *15:01/*11:01 | nd[5] | A |
| 15 | White | *01:02/*05:01 | *06:02/*03:01 | *15:01/*11:01 | nd[5] | C |
| 16 | White | *03:03/*05:05 | *03:01/*03:01 | *04:07/*11:01 | DRB4*01:03/DRB3*02:02 | A (probable) |
| 17 | White | *01:02/*03:01 | *06:02/*03:02 | *15:01/*04:04 | nd[5] | A (probable) |
| 18 | White | *01:02/*05:01 | *06:02/*03:01 | *15:01/*11:01 | nd[5] | A (probable) |
| 19 | White | nd | *06:02/*03:01 | *15:01/*11:01 | nd[5] | C T A |
| 20 | White | *01:02/*05:05 | *06:02/*03:01 | *15:01/*11:04 | DRB5*01:01/DRB3*02:02 | A |
| 21 | White | *01:02/*01:04 | *06:02/*05:03 | *15:01/*14:54 | DRB5*01:01/DRB3*02:02 | C |
| 22 | Native American/ White | *01:04/*05:03 | *05:03/*03:01 | *14:54/*14:02 | DRB3*02:02/DRB3*01:01 | A |
| 23 | Middle Eastern/ White | *01:02/*05:01 | *06:02/*03:01 | *15:01/*11:01 | DRB5*01:01/DRB3*02:02 | A |
| 24 | Middle Eastern | *01:02/*05:01 | *03:01/*03:01 | *11:04/*13:03 | nd | C T A |
| 25 | Hispanic/ White | *05:05/*05:03 | *03:01/*03:01 | *13:03/*14:02 | nd | A |
| 26 | Hispanic | *01:02/*05:01 | *06:02/*03:01 | *13:03/*11:01 | DRB3*02:02/DRB3*01:01 | C T |
| 27 | Hispanic | *01:02/*04:01 | *06:02/*04:02 | *15:01/*08:02 | DRB5*01:01/Absent | A |
| 28 | Hispanic | nd | *06:02/*04:02 | *15:01/*08:02 | DRB5*01:01/Absent | A |
| 29 | Hispanic | *01:02/*05:03 | *06:02/*03:01 | *15:01/*14:02 | DRB5*01:01/DRB3*03:01 | A T |
| 30 | South Asian/ White | *01:02/*06:01 | *06:02/*03:01 | *15:01/*12:02 | DRB5*01:01/DRB3*03:01 | A T |
| 31 | South Asian | *01:02/*05:05 | *05:02/*03:01 | *15:06/*11:04 | DRB5*01:01/DRB3*pos[6] | A C |
| 32 | South Asian | *01:02/*01:03 | *06:01/*06:01 | *15:01/*15:01 | nd[5] | A C R T |
| 33 | South Asian/Asian | *01:02/*06:01 | *05:02/*03:01 | *15:01/*12:02 | DRB5*01:01/DRB3*03:01 | C |
| 34 | Black/ White | *01:02/nd[7] | *06:02/nd[7] | *15:01/nd[7] | DRB5*01:01/nd[7] | A |
| 35 | Black/ White | *01:02/*01:02 | *06:02/*06:02 | *15:01/*11:01 | DRB5*01:01/DRB3*02:02 | A T |
| 36 | Black | *01:02/*05:01 | *06:02/*03:01 | *15:03/*13:03 | DRB5*01:01/DRB3*01:01 | A |
| 37 | Black | *01:02/*04:01 | *06:02/*04:02 | *15:03/*03:02 | nd[5] | A T |

TABLE 3-continued

HLA-DQ and -DR in cases with delayed hypersensitivity reaction (DHR)

| n | Ancestry1 | DQA1 | DQB1 | DRB1 | DRB3/4/5/Absent2 | DHR3, 4 |
|---|---|---|---|---|---|---|
| 38 | Black | *01:02/*01:02 | *06:02/*05:01 | *15:01/*15:03 | DRB5*01:01/DRB5*01:01 | A |
| 39 | Black | *04:01/*05:05 | *03:19/*03:01 | *08:04/*08:06 | Absent/Absent | C R |
| Cases with DHR without DLD (sJIA-DHR/DLD) | | | | | | DHR[3, 4] |
| 1 | White | *01:02/*05:05 | *06:02/*03:01 | *15:01/*11:04 | nd[5] | A |
| 2 | White | *01:03/*02:01 | *06:01/*02:02 | *07:01/*08:03 | DRB4*01:03/Absent | A |
| 3 | White | *01:02/*01:02 | *06:02/*06:02 | *15:01/*15:01 | DRB5*01:01/DRB5*01:01 | A |
| 4 | White | *01:01/*03:01 | *03:02/*05:01 | *01:01/*04:02 | nd | R A T |
| 5 | White | *01:02/*05:01 | *06:02/*03:01 | *15:01/*13:03 | nd[5] | A C R (probable) |
| 6 | White | *01:02/*03:01 | *06:02/*03:02 | *15:01/*04:01 | nd[5] | A C |
| 7 | White | *01:02/*04:01 | *06:02/*04:02 | *15:01/*08:04 | DRB5*01:01/Absent | A (probable) |
| 8 | White | *01:02/*01:01 | *06:02/*05:01 | *15:01/*01:01 | DRB5*01:01/Absent | C |
| 9 | Middle Eastern | *01:02/*05:05 | *03:01/*05:02 | *15:06/*13:03 | DRB5*01:01/DRB3*01:01 | A |
| 10 | Hispanic | *01:02/*05:05 | *06:02/*03:01 | *15:01/*13:03 | DRB5*01:01/DRB3*01:01 | A |
| 11 | Hispanic | nd | *06:02/*06:03 | *11:01/*13:01 | nd | A C T |
| 12 | Asian | *01:02/*05:01 | *06:02/*02:01 | *15:01/*03:01 | nd[5] | T A C |
| 13 | Asian | *01:02/*01:02 | *05:02/*05:02 | *15:01/*15:01 | nd[5] | A C |
| 14 | South Asian | *01:03/*05:05 | *06:01/*03:01 | *15:01/*11:01 | DRB5*01:01/DRB3*02:02 | A |
| 15 | South Asian | *01:03/*06:01 | *06:01/*03:01 | *15:01/*12:02 | DRB5*01:01/DRB3*03:01 | A C R T |
| 16 | Black | *01:02/*01:05 | *06:02/*05:01 | *12:01/*11:01 | DRB3*01:01/DRB3*02:02 | T |
| sJIA with suspected anakinra reaction (sJIA-sAR) | | | | | | |
| 1 | Black | *01:02/*04:01 | *06:02/*04:02 | *15:03/*03:02 | DRB5*01:01/DRB3*01:01 | A |
| Kawasaki disease cases with features of suspected anakinra reaction (KD-sAR)[8] | | | | | | sAR[4] |
| 1 | White | *01:02/*03:01 | *06:02/*03:02 | *15:01/[4]04:02 | DRBS*01:01/DRB4*01:03 | A |
| 2 | White | *01:01/*05:05 | *03:01/*05:01 | *01:01/*12:01 | Absent/DRB3*02:02 | A |
| 3 | Hispanic | *01:02/.01:01 | *06:02/*05:01 | *15:03/.01:01 | DRBS*01:01/Absent | A |
| 4 | White/Asia | *01:02/*05:05 | *06:02/*03:01 | *15:01/*13:03 | DRBS*01:01/DRB3*01:01 | A |

nd, not determined;
DHR, delayed hypersensitivity reaction;
sAR, suspected anakinra reaction (delayed type, not anaphylaxis);
Underline indicates DHR/sAR risk alleles;
HLA class I were typed in the majority of these subjects, and analysis found no independent association with DHR (not shown);
[1]Ancestry self-identification as White, Hispanic, South Asian, Asian or Black, with mixed parentage noted;
[2]Absent: Absence of HLA-DRB3/4/5 when HLA-DRB1*01/*08/*10 are present[18];
[3]DHR by clinical diagnosis and/or 'definite' by RegiSCAR[7]; (probable): 'probable' by RegiSCAR, each with continuous high dose steroids, 1 with drug-induced liver injury and limited other data;
[4]Drugs implicated: A, anakinra C, canakinumab R, rilonacept, T, tocilizumab, DRB5*01:01 is tightly linked to DRB1*15:01, *15:03, *15:06;
[6]Does not genotype due to crossmapping;
[7]Imputed as one DRB1*15:01 haplotype by single nucleotide polymorphism (SNP); ;
[8]Details provided on Table 6.

TABLE 4

HLA-DQ and -DR in drug tolerant controls

| n | Ancestry[1] | DQA1 | DQB1 | DRB1 | DRB3/4/5/Absent[2] | Drug exposure[3] |
|---|---|---|---|---|---|---|
| sJIA controls with ≥1 year of uneventful exposure to IL-1/IL-6 inhibitors (sJIA-drug tolerant) | | | | | | |
| 1 | White | *01:01/*02:01 | *05:01/*03:03 | *01:01/*07:01 | Absent/DRB4*01:03 | A C T |
| 2 | White | *01:02/*03:03 | *04:02/*06:04 | *13:02/*04:04 | DRB3*03:01/DRB4*01:03 | A C |
| 3 | White | *03:03/*04:02 | *03:01/*04:02 | *04:01/*08:01 | DRB4*01:03/Absent | A T |
| 4 | White | *01:01/*05:05 | *03:01/*05:01 | *01:01/*11:04 | Absent/DRB3*02:02 | A |
| 5 | White | *01:01/*03:01 | *03:05/*05:01 | *01:01/*04:03 | Absent/DRB4*01:03 | A C |
| 6 | White | *05:01/*05:01 | *02:01/*03:01 | *03:01/*11:04 | nd | C |
| 7 | White | *01:02/*05:01 | *02:01/*06:01 | *03:01/*13:02 | nd | C |
| 8 | White | *01:02/*05:01 | *02:01/*06:04 | *03:01/*13:02 | nd | C |
| 9 | White | *03:01/*03:01 | *03:02/*06:11 | *04:04/*04:05 | nd | A C |
| 10 | White | *01:01/*03:01 | *03:02/*05:01 | *01:01/*04:04 | nd | C |
| 11 | White | *03:01/*05:01 | *03:01/*03:01 | *04:01/*11:01 | nd | T |
| 12 | White | *02:01/*02:01 | *02:02/*03:03 | *07:01/*07:01 | DRB3*01:01/DRB4*01:03 | A |
| 13 | White | *03:01/*05:01 | *02:01/*03:02 | *03:01/*04:04 | DRB4*01:01/DRB3*01:01 | A C T |
| 14 | White | *05:05/*01:04 | *03:01/*05:03 | *11:04/*14:54 | DRB3*02:02/DRB3*02:02 | A C T |
| 15 | White | *02:01/*03:03 | *03:02/*03:03 | *04:01/*07:01 | DRB4*01:03N/DRB4*01:03 | A |
| 16 | White | *01:03/*05:01 | *02:01/*06:03 | *03:01/*13:01 | DRB3*01:01/DRB3*02:02 | T |

TABLE 4-continued

| n | Ancestry[1] | DQA1 | DQB1 | DRB1 | DRB3/4/5/Absent[2] | Drug exposure[3] |
|---|---|---|---|---|---|---|
| HLA-DQ and -DR in drug tolerant controls | | | | | | |
| 17 | White | *01:03/*03:03 | *03:01/*06:03 | *04:01/*13:01 | DRB3*02:02/DRB4*01:03 | A |
| 18 | White | *05:01/*05:05 | *02:01/*03:01 | *03:01/*11:01 | DRB3*02:02/DRB3*02:02 | AT |
| 19 | White | *01:02/*02:01 | *03:03/*06:04 | *07:01/*13:02 | DRB4*01:03/DRB3*03:01 | T |
| 20 | Hispanic | *02:01/*03:01 | *02:02/*03:02 | *04:01/*07:01 | DRB4*01:03/DRB4*01:01 | C |
| 21 | Hispanic | *01:02/*01:01 | *05:01/*05:01 | *13:02/*13:02 | DRB3*03:01/DRB3*03:01 | A C R T |
| 22 | Hispanic | *04:01/*04:01 | *04:02/*04:02 | *08:02/*08:02 | Absent/Absent | AT |
| 23 | Hispanic | *03:03/*04:01 | *03:02/*04:02 | *08:02/*04:01 | Absent/DRB4*01:03 | A |
| 24 | South Asian | *03:01/*03:03 | *03:01/*03:02 | *04:01/*04:04 | DRB4*01:03/DRB4*01:03 | A C |
| 25 | Asian | *02:01/*06:01 | *02:02/*03:01 | *07:01/*12:02 | DRB4*01:03/DRB3*03:01 | A C R T |
| 26 | Asian | *01:02/*05:01 | *02:01/*06:04 | *03:01/*13:02 | DRB3*02:02/DRB3*03:01 | A |
| 27 | Black | *03:01/*03:03 | *02:02/*03:02 | *04:03/*09:01 | DRB4*01:03/DRB4*01:03 | T |
| 28 | Black | *01:02/*02:01 | *06:02/*02:02 | *15:03/*13:03 | DRB5*01:01/DRB3*02:02 | A |
| 29 | Black | *01:02/*01:01 | *05:01/*06:04 | *15:03/*13:02 | DRB5*01:01/DRB3*03:01 | A |
| 30 | Black | *01:02/*03:03 | *06:02/*02:02 | *09:01/*11:01 | DRB4*01:01/DRB3*02:02 | A |
| Kawasaki disease controls without features of DHR during anakinra (KD-anakinra tolerant)[4] | | | | | | |
| 1 | White | *03:01/*03:01 | *03:02/*03:02 | *04:01/*04:01 | DRB4*01:03/DRB4*01:03 | A |
| 2 | Hispanic | *03:01/*05:05 | *03:01/*03:02 | *01:03/*04:02 | DRB4*01:03/Absent | A |
| 3 | Hispanic | *01:01/*05:01 | *02:01/*05:01 | *01:03/*03:01 | Absent/DRB3*02:02 | A |
| 4 | Hispanic | *03:03/*04:01 | *03:02/*04:02 | *04:05/*08:02 | DRB4*01:03/Absent | A |
| 5 | Hispanic | *02:01/*05:05 | *02:02/*03:01 | *07:01/*16:02 | DRB4*01:03/DRB5*02:02 | A |
| 6 | Hispanic | *01:03/*03:01 | *03:02/*06:02 | *04:07/*13:01 | DRB3*02:02/DRB4*01:03 | A |
| 7 | Hispanic | *04:01/*05:05 | *03:01/*04:02 | *08:02/*16:02 | Absent/DRB5*02:02 | A |
| 8 | Hispanic | *03:01/*04:01 | *03:02/*04:02 | *03:02/*04:04 | DRB3*01:62/DRB4*01:03 | A |
| 9 | Hispanic/ White | *05:01/*05:05 | *02:01/*03:01 | *03:01/*16:02 | DRB3*01:01/DRB5*02:02 | A |
| 10 | Asian | *01:03/*01:03 | *06:01/*06:03 | *08:03/*13:01 | Absent/DRB3*01:01 | A |
| 11 | Asian | *01:02/*05:01 | *02:01/*05:02 | *03:01/*15:02 | DRB5*01:01/DRB3*02:02 | A |
| 12 | Asian | *01:03/*06:01 | *03:01/*06:01 | *12:02/*15:02 | DRB5*01:02/DRB3*03:01 | A |
| 13 | Asian/ White | *03:01/*05:01 | *02:01/*03:02 | *03:01/*04:03 | DRB3*02:02/DRB4*01:03 | A |
| 14 | Black | *03:01/*03:03 | *03:01/*03:02 | *04:01/*04:04 | DRB4*01:03/DRB4*01:03 | A |
| 15 | Black | *01:02/*02:01 | *02:02/*05:02 | *13:03/*16:02 | DRB3*02:02/DRB5*02:21 | A |

HLA class I loci were typed in the majority of these subjects (not shown);

[1]Ancestry self-identification as White, Hispanic, South Asian, Asian or Black, with mixed parentage noted;

[2]Absent: Absence of HLA-DRB3/4/5 when HLA-DRB1*01/*08/*10 are present[18];

[3]A, anakinra; C, canakinumab; R, rilonacept; T, tocilizumab; Details provided in Table 6.

TABLE 5

| n | Illness | Sex[2] | HLA-DRB1*15 alleles[3] | Tocilizumab anaphylaxis[4] | Fatal[5] | Eosinophilia[6] | Atypical rash[7] | Face or neck rash[8] | v PAP/ELP[9] | PH[10] |
|---|---|---|---|---|---|---|---|---|---|---|
| Clinical features in sJIA cases and controls[1] | | | | | | | | | | |
| sJIA cases with DHR and diffuse lung disease (DLD) developing during treatment (sJIA-DHR/DLD)[1] | | | | | | | | | | |
| 1 | sJIA | F | 1 | 1 | 0 | 1 | 1 | 0 | no biopsy | 0 |
| 2 | sJIA | F | 1 | 0 | 0 | 2 | 1 | 1 | no biopsy | 1 |
| 3 | sJIA | F | 0 | 1 | 1 | 2 | 1 | 0 | 1 | 1 |
| 4 | sJIA | M | 1 | 1 | 1 | 2 | 1 | 1 | 1 | 0 |
| 5 | sJIA | F | 1 | 1 | 0 | 2 | 1 | na | 1 | 0 |
| 6 | sJIA-like | F | 1 | not exposed | 0 | 1 | 1 | na | 1 | 0 |
| 7 | sJIA | F | 1 | not exposed | 0 | 2 | 1 | 1 | 1 | 0 |
| 8 | sJIA | F | 0 | 1 | 1 | 2 | 1 | 1 | no biopsy | 1 |
| 9 | sJIA | F | 1 | not exposed | 1 | 2 | 1 | 1 | no biopsy | 0 |
| 10 | sJIA | M | 1 | 0 | 0 | 2 | 1 | 1 | no biopsy | 0 |
| 11 | sJIA | F | 1 | 1 | 0 | 1 | no atypical rash reported[12] | | 1 | 0 |
| 12 | sJIA | M | 1 | 0 | 0 | na | 1 | na | no biopsy | 0 |
| 13 | sJIA | F | 1 | 0 | 0 | 1 | 1 | 1 | 1 | 1 |
| 14 | sJIA | F | 1 | 0 | 0 | 2 | 1 | 0 | no biopsy | 0 |
| 15 | sJIA | F | 1 | not exposed | 0 | 1 | 1 | na | 1 | 0 |
| 16* | sJIA | F | 0 | 0 | 0 | 1 | no atypical rash reported[12] | | no biopsy | 0 |
| 17* | sJIA | F | 1 | 1 | 0 | 0 | 1 | na | no biopsy | 0 |
| 18 | sJIA | F | 1 | 0 | 0 | 0 | 1 | 1 | no biopsy | 0 |
| 19 | sJIA | F | 1 | 0 | 0 | 1 | 1 | 1 | no biopsy | 0 |
| 20 | sJIA | M | 1 | 0 | 0 | 2 | 1 | na | no biopsy | 0 |
| 21 | sJIA-like | F | 0 | not exposed | 0 | 2 | 1 | 1 | no biopsy | 0 |
| 22 | sJIA-like | F | 1 | not exposed | 0 | na | 1 | 1 | 1 | 0 |

TABLE 5-continued

Clinical features in sJIA cases and controls[1]

| | | | | | | | | | | |
|---|---|---|---|---|---|---|---|---|---|---|
| 23 | sJIA | F | 0 | 1 | 0 | 2 | 1 | 1 | 1 | 1 |
| 24 | sJIA | F | 0 | 1 | 1 | 1 | 1 | 1 | 1 | 0 |
| 25 | sJIA-like | F | 0 | 0 | 0 | 2 | 1 | na | 1 | 0 |
| 26 | sJIA | F | 1 | 0 | 0 | 1 | 1 | 1 | 1 | 0 |
| 27 | sJIA | F | 1 | not exposed | 0 | 2 | 1 | 1 | no biopsy | 0 |
| 28 | sJIA-like | F | 1 | 0 | 0 | 1 | 1 | 1 | no biopsy | 0 |
| 29 | sJIA | M | 1 | 0 | 0 | 1 | 1 | 1 | 1 | 0 |
| 30 | sJIA | M | 1 | not exposed | 0 | 1 | 1 | na | 1 | 0 |
| 31 | sJIA | M | 1 | 1 | 0 | 2 | 1 | 1 | 1 | 0 |
| 32 | sJIA | F | 1 | 1 | 0 | 1 | 1 | na | 1 | 0 |
| 33 | sJIA-like | F | 1 | 0 | 1 | 2 | 1 | 1 | 1 | 0 |
| 34 | sJIA | F | 1 | 0 | 0 | 2 | 1 | na | 1 | 0 |
| 35 | sJIA | M | 1 | 0 | 1 | 2 | 1 | na | 1 | 0 |
| 36 | AOSD | F | 1 | 0 | 0 | 2 | na | na | no biopsy | 0 |
| 37 | sJIA | F | 1 | 0 | 0 | 2 | 1 | 0 | no biopsy | 1 |
| 38 | sJIA | F | 0 | 1 | 0 | 2 | 1 | 1 | no biopsy | 1 |

sJIA cases with DHR without DLD (sJIA-DHR)[13]

| | | | | | | | | |
|---|---|---|---|---|---|---|---|---|
| 1 | sJIA | F | 1 | 0 | 0 | 1 | 1 | 1 |
| 2 | sJIA | F | 0 | 0 | 0 | 2 | 1 | 1 |
| 3 | sJIA | F | 1 | not exposed | 0 | 1 | 1 | 1 |
| 4 | sJIA-like | F | 0 | 0 | 0 | 1 | 1 | 1 |
| 5 | sJIA | M | 1 | 1 | 0 | 2 | 1 | 1 |
| 6 | sJIA | M | 1 | not exposed | 0 | 2 | 1 | 1 |
| 7 | sJIA | M | 1 | 0 | 0 | 1 | 1 | 0 |
| 8 | sJIA | F | 1 | 0 | 0 | 0 | no atypical rash reported[12] | |
| 9 | sJIA | F | 1 | not exposed | 0 | 2 | 1 | 0 |
| 10 | sJIA | M | 1 | not exposed | 0 | 1 | 1 | 0 |
| 11 | sJIA | F | 0 | 0 | 0 | 0 | 1 | 1 |
| 12 | sJIA | M | 1 | 0 | 0 | 1 | 1 | 1 |
| 13 | sJIA | F | 1 | 0 | 0 | 2 | 1 | 1 |
| 14 | sJIA | F | 1 | not exposed | 0 | 1 | 1 | 1 |
| 15 | sJIA | M | 1 | 0 | 0 | 0 | 1 | 1 |
| 16 | sJIA | F | 0 | 0 | 0 | 2 | 1 | na |

sJIA Controls (sJIA drug-tolerant)[1]

| n | Illness | Sex[2] | HLA-DRB1*15 alleles[3] | Tocilizumab anaphylaxis[4] | Fatal | Eosinophilia[5] | Atypical rash | Face or neck rash |
|---|---|---|---|---|---|---|---|---|
| 1 | sJIA | M | 0 | not exposed | 0 | 0 | 0 | 0 |
| 2 | sJIA | M | 0 | not exposed | 0 | 0 | 0 | 0 |
| 3 | sJIA | F | 0 | 0 | 0 | 0 | 0 | 0 |
| 4 | sJIA | M | 0 | not exposed | 0 | 0 | 0 | 0 |
| 5 | sJIA | F | 0 | not exposed | 0 | 0 | 0 | 0 |
| 6 | sJIA | M | 0 | not exposed | 0 | 0 | 0 | 0 |
| 7 | AOSD | F | 0 | not exposed | 0 | 0 | 0 | 0 |
| 8 | sJIA | F | 0 | not exposed | 0 | 0 | 0 | 0 |
| 9 | sJIA | M | 0 | not exposed | 0 | 0 | 0 | 0 |
| 10 | sJIA | F | 0 | not exposed | 0 | 0 | 0 | 0 |
| 11 | sJIA | F | 0 | not exposed | 0 | 0 | 0 | 0 |
| 12 | sJIA | F | 0 | not exposed | 0 | 0 | 0 | 0 |
| 13 | sJIA | F | 0 | 0 | 0 | 0 | 0 | 0 |
| 14 | sJIA | M | 0 | 0 | 0 | 0 | 0 | 0 |
| 15 | sJIA | F | 0 | not exposed | 0 | 0 | 0 | 0 |
| 16 | sJIA | F | 0 | 0 | 0 | 0 | 0 | 0 |
| 17 | sJIA | M | 0 | not exposed | 0 | 0 | 0 | 0 |
| 18 | sJIA | M | 0 | not exposed | 0 | 0 | 0 | 0 |
| 19 | AOSD | F | 0 | 0 | 0 | 0 | 0 | 0 |
| 20 | sJIA | M | 0 | 0 | 0 | 0 | 0 | 0 |
| 21 | sJIA | F | 0 | 0 | 0 | 0 | 0 | 0 |
| 22 | sJIA | F | 0 | 0 | 0 | 0 | 0 | 0 |
| 23 | sJIA | F | 0 | 0 | 0 | 0 | 0 | 0 |
| 24 | sJIA | M | 0 | not exposed | 0 | 0 | 0 | 0 |
| 25 | sJIA | F | 0 | not exposed | 0 | 0 | 0 | 0 |
| 26 | sJIA | F | 0 | 0 | 0 | 0 | 0 | 0 |
| 27 | sJIA | M | 0 | 0 | 0 | 0 | 0 | 0 |
| 28 | sJIA | F | 1 | not exposed | 0 | 0 | 0 | 0 |

TABLE 5-continued

| Clinical features in sJIA cases and controls[1] | | | | | | | | |
|---|---|---|---|---|---|---|---|---|
| 29 | sJIA | F | 1 | not exposed | 0 | 0 | 0 | 0 |
| 30 | sJIA | F | 0 | not exposed | 0 | 0 | 0 | 0 |

*Resolved lung disease 4-10 months after promptly stopping cytokine inhibitor (anakinra, tocilizumab, canakinumab) near the time DHR was first noted. Normal chest CT, echocardiogram and oxygen saturation. Improvement in these cases appears more complete than in reported cases with delayed withdrawal of the implicated medications; na = not available, 0 = absent, 1 = present, except for eosinophilia which is coded as per footnote 6 ([6]); Clinical features during treatment with the drug implicated in DHR;

[2]No significant difference for sex frequency between cases (sJIA-DHR/DLD + sJIA-DHR) and controls (sJIA drug-tolerant): F vs M: OR 1.5 (95% CI 0.47, 5.1), p = 0.47;

[3]Presence of HLA-DRB1*15:01, *15:03 or *15:06;

[4]Immediate anaphylactic reaction during tocilizumab administration; all subjects discontinued drug. This reaction is significantly enriched in sJIA/DLD vs reported incidence in trials in &BA[B]; it is not a DHR and is not associated with the DHR-associated DRB1* 15:01,*15:03, *15:06;

[5]Fatalities (7/7) occurred during continuation or restart of implicated medication. Time from DLD to data close ≥4 months;

[6]1 = peak absolute eosinophil count (AEC) > normal limit < 1500/ul(eosinophilic); 2 = AEC ≥ 1500/ul(hyper-eosinophilic).[25] For sJIA-DHR/DLD and sJIA-DHR, respectively, median (IQR) peak AEC = 2110/ul (1250, 3960) and 1105/ul (908, 2198) and % eosinophil = 19% (12, 31) and 16% (12, 23), despite known concurrent steroids in "50% of subjects;

[7]Non-evanescent rash, often intensely pruritic, variably including hyperpigmentation, eczema, angioedema, confluent erythema, serpiginous, vesicular and flagellate dermatologic patterns. Skin biopsy reports were provided for 10 cases (sJIA-DH R/DLD (6), OA-DHR(4)) each with pathologic features consistent with drug reaction including interface dermatitis, dyskeratosis, and eosinophilia.

[8]Rash involving the face or neck is highly prevalent (noted in "80%) in DRESS type drug related reactions.[26];

[9]Variant pulmonary alveolar proteinosis/endogenous lipoid pneumonia with notable presence of lymphocytoplasmic infiltrate and vascular changes.[8];

[10]Pulmonary hypertension by echocardiogram or cardiac cathertization;

[11]Time from first feature of DHR until recognition of DLD ranged from 1 month to 2.3 years;

[12]Both sJIA-DHR/DLD subjects without atypical rash experienced uninterrupted high dose steroid treatment;

[13]Median length of follow up from first feature of DHR to data close was 5.9 yrs (range 0.5, 8.7). 10/11 abandoned the implicated medication and have not developed DLD, followed 0.5-to 8.6 yrs after stopping. The remaining case has persistent eosinophilia on anakinra;

[14]Treated uneventfully for ≥1 yr. None with eosinophilia or non-evanescent atypical rash.

TABLE 6

Clinical features in Kawasaki disease cases and controls[1]

| n | Sex[2] | HLA-DRB1*15 Alleles[3] | Anakinra Duration (days) | Atypical Lymphocytes[4] | Eosinophilia[5] | Atypical rash[6] | Face or neck rash[7] |
|---|---|---|---|---|---|---|---|
| KD cases with features of suspected anakinra reaction (KD-sAR)[8] | | | | | | | |
| 1 | M | 1 | 39 | 1 | 1 | 0 | 0 |
| 2 | M | 0 | 41 | 1 | 1 | 0 | 0 |
| 3 | M | 1 | 42 | 1 | 1 | 1 | 1 |
| 4 | M | 1 | 13 | 0 | 1 | 0 | 0 |
| KD-anakinra tolerant | | | | | | | |
| 1 | M | 0 | 9 | 0 | 0 | 0 | |
| 2 | M | 0 | 41 | 0 | 0 | 0 | |
| 3 | M | 0 | 41 | 0 | 0 | 0 | |
| 4 | M | 0 | 17 | 0 | 0 | 0 | |
| 5 | M | 0 | 37 | 0 | 0 | 0 | |
| 6 | M | 0 | 10 | 0 | 0 | 0 | |
| 7 | M | 0 | 39 | 1 | 0 | 0 | |
| 8 | M | 0 | 11 | 0 | 0 | 0 | |
| 9 | M | 0 | 13 | 0 | 0 | 0 | |
| 10 | M | 0 | 46 | 0 | 0 | 0 | |
| 11 | F | 0 | 28 | 0 | 0 | 0 | |
| 12 | F | 0 | 12 | 0 | 0 | 0 | |
| 13 | F | 0 | 41 | 0 | 0 | 0 | |
| 14 | M | 0 | 43 | 0 | 0 | 0 | |
| 15 | M | 0 | 16 | 0 | 0 | 0 | |

KD-sAR, suspected anakinra reaction (delayed type, not anaphylaxis), 0 = absent, 1 = present, except for eosinophilia, coded as per footnote 5 ([5]);

[1]Clinical features during treatment with anakinra;

[2]No signifcant difference for sex frequency between KD-sAR and KD-anakinra tolerant (M vs F: OR 0.5 (95% CI 0.02, 11.4), p = 0.66);

[3]Presence of HLA-DRB1*15:01, *15:03 or *15:06;

[4]Atypical lymphocytes required a value >2% of WBC and increased >2% from baseline study visit, prior to anakinra;

[5]1 = AEC ≥ 500 and elevated ≥50% over baseline study value (eosinophilic); 2 = AEC ≥ 1500/ul and elevated ≥50% over baseline study value (hyper-eosinophilic)[25]. Elevated AEC ranged from 630/ul to 1071/ul (382% to infinite increase over study baseline);

[6]Non-evanescent rash began during anakinra treatment, described as intensely pruritic with erythema and localized swelling. Diagnosed clinically as an atopic dermatitis flare, although acuity and location were not typical. No biopsy obtained;

[7]Rash involving the face or neck is highly prevalent (noted in ~80%) in DRESS type drug related reactions[26];

[8]Data were incomplete for scoring by RegiSCAR. Data used to assess suspected anakinra reaction were appearance of new rash, eosinophilia and atypical lymphocyte counts at baseline study visit, during and after anakinra; Table 7: Association analysis for HLA alleles in sJIA-DHR subjects vs. INCHARGE sJIA cases and controls.

| a. Ancestrally-matched by PCA[1] | | Subjects with HLA allele of interest' | | | sJIA-DHR vs. INCHARGE sJIA | | sJIA-DHR vs. INCHARGE controls | |
|---|---|---|---|---|---|---|---|---|
| | Allele | sJIA-DHR | INCHARGE sJIA | INCHARGE controls | p-value | OR (95% CI) | p-value | OR (95% CI) |
| sJIA-DHR/DLD vs. European GWAS subjects | HLA-DRB1*15:01[3] | **11/12 (92%)** | ***130/550 (24%)*** | ***822/3279 (25%)*** | 6.56E−07 | 35.5 (4.5, 277.9) | 9.50E−07 | 32.9 (4.2, 255.1) |
| | HLA-DRB1.15:XX[4] | 11/12 (92%) | 130/550 (24%) | 823/3279 (25%) | 6.56E−07 | 35.5 (4.5, 277.9) | 9.62E−07 | 32.8 (4.2, 254.6) |
| | HLA-DQB1*06:02 | **11/12 (92%)** | ***128/550 (23%)*** | ***806/3279 (25%)*** | 5.56E−07 | 36.3 (4.6, 283.6) | 7.65E−07 | 33.8 (4.4, 261.8) |
| | HLA-DQB1 06:XX | 11/12 (92%) | 219/550 (40%) | 1391/3279 (42%) | 1.73E−04 | 16.6 (2.1, 129.7) | 3.05E−04 | 14.9 (1.9, 115.8) |
| | HLA-DQA1 01:02 | **11/12 (92%)** | ***188/550 (34%)*** | ***1148/3279 (35%)*** | 3.37E−05 | 21.1 (2.7, 165.3) | 3.73E−05 | 20.4 (2.6, 158.3) |
| | HLA-DRB1*11:01[5] | 4/12 (33%) | 103/550 (19%) | 313/3279 (10%) | 0.025 | 5.8 (1.3, 26.2) | 0.002 | 12.6 (2.8, 56.7) |
| | HLA-DQB1 03:01[5] | **5/12 (42%)** | ***240/550 (44%)*** | ***1072/3279 (33%)*** | 0.14 | 3.2 (0.6, 16.8) | 0.036 | 5.1 (1.0, 26.6) |
| Any sJIA-DHR[6] vs. European GWAS subjects | HLA-DRB1*15:01 | **13/14 (93%)** | **130/550 (24%)** | **822/3279 (25%)** | 4.48E−08 | 42 (5.4, 324.1) | 6.53E−08 | 38.9 (5 1, 297.5) |
| | HLA-DRB1*15:XX[4] | 13/14 (93%) | 130/550 (24%) | 823/3279 (25%) | 4.48E−08 | 42 (5.4, 324.1) | 6.63E−08 | 38.8 (5.1, 297.0) |
| | HLA-DQB1*06:02 | **13/14 (93%)** | ***128/550 (23%)*** | **806/3279 (25%)** | 3.70E−08 | 42.9 (5.6, 330.8) | 5.06E−08 | 39.9 (5.2, 305.4) |
| | HLA-DQB1*06:XX | 13/14 (93%) | 219/550 (40%) | 1391/3279 (42%) | 3.12E−05 | 19.6 (2.6, 151.3) | 5.91E−05 | 17.6 (2.3, 135.1) |
| | HLA-DQA1 01:02 | **13/14 (93%)** | ***188/550 (34%)*** | ***1148/3279 (35%)*** | 4.56E−06 | 25 (3.2, 192.8) | 4.95E−06 | 24.1 (3.2, 184.7) |
| | HLA-DRB1*11:01[5] | 4/14 (29%) | 103/550 (19%) | 313/3279 (10%) | 0.08 | 3.5 (0.9, 13.2) | 0.007 | 7.6 (2.0, 28.4) |
| | HLA-DQB1 03:01[5] | **6/14 (43%)** | ***240/550 (44%)*** | ***1072/3279 (33%)*** | 0.17 | 2.6 (0.6, 10.4) | 0.038 | 4.1 (1.0, 16.5) |

| b. Self-reported "White" analysis[1] | | Subjects with HLA allele of interest[2] | | | sJIA-DHR vs. INCHARGE OA | | sJIA-DHR vs. INCHARGE controls | |
|---|---|---|---|---|---|---|---|---|
| | Allele | sJIA-ILD/DHR | INCHARGE sJIA | INCHARGE controls | p-value | OR (95 CI) | 13-value | OR (95% CI) |
| "White" sJIA-DHR/DLD vs. European GWAS subjects | HLA-DRB1*15:01[3] | **14/18 (78%)** | ***130/550 (24%)*** | ***822/3279 (25%)*** | 2.03E−06 | 11.3 (3.7, 35.0) | 2.97E−06 | 10.5 (3.4, 31.9) |
| | HLA-DRB1*15:XX[4] | 14/18 (78%) | 130/550 (24%) | 823/3279 (25%) | 2.03E−06 | 11.3 (3.7, 35.0) | 3.02E−06 | 10.4 (3.4, 31.8) |
| | HLA-DQB1 06:02 | **13/18 (72%)** | ***128/550 (23%)*** | ***806/3279 (25%)*** | 1.67E−05 | 8.6 (3.0, 24.5) | 2.31E−05 | 8.0 (2.9, 22.4 |
| | HLA-DQB1 06:XX | 14/18 (78%) | 219/550 (40%) | 1391/3279 (42%) | 1.24E−03 | 5.3 (1.7, 16.3) | 2.28E−03 | 4.8 (1.6, 14.5) |

-continued

| a. Ancestrally-matched by PCA[1] | | Subjects with HLA allele of interest' | | | sJIA-DHR vs. INCHARGE sJIA | | sJIA-DHR vs. INCHARGE controls | |
|---|---|---|---|---|---|---|---|---|
| | Allele | sJIA-DHR | INCHARGE sJIA | INCHARGE controls | p-value | OR (95% CI) | p-value | OR (95% CI) |
| "White" any sJIA-DHR[6] vs. European GWAS subjects | HLA-DQA1*01:02 | **14/18 (78%)** | ***188/550 (34%)*** | ***1148/3279 (35%)*** | 1.97E−04 | 6.7 (2.2, 20.8) | 2.16E−03 | 6.5 (2.1, 19.8) |
| | HLA-DRB1*11:01[5] | 5/18 (28%) | 103/550 (19%) | 313/3279 (10%) | 0.1 | 2.7 (0.8, 8.5) | 0.005 | 5.9 (1.9, 18.2) |
| | HLA-Da B1 03:01[5] | **9/18 (50%)** | ***240/550 (44%)*** | ***1072/3279 (33%)*** | 0.066 | 2.9 0.9, 9.6 | 0.007 | 4.6 1.4, 15.1 |
| | HLA-DRB1.15:01[3] | **18/24 (75%)** | ***130/550 (24%)*** | ***822/3279 (25%)*** | 2.34E−07 | 9.7 (3.8, 25.0) | 3.33E−07 | 9 (3.5, 22.7) |
| | HLA-DRB1*15:XX[4] | 18/24 (75%) | 130/550 (24%) | 823/3279 (25%) | 2.34E−07 | 9.7 (3.8, 25.0) | 3.40E−07 | 9.0 (3.5, 22.6) |
| | HLA-DQB1 06:02 | **17/24 (71%)** | ***128/550 (23%)*** | ***806/3279 (25%)*** | 1.57E−06 | 8.0 (3.2, 19.7) | 2.12E−06 | 7.5 (3.1, 18.0) |
| | HLA-DQB1 06:XX | 19/24 (79%) | 219/550 (40%) | 1391/3279 (42%) | 1.16E−04 | 5.7 (2.1, 15.6) | 2.46E−04 | 5.2 (1.9, 13.8) |
| | HLA-DQA1*01:02 | **18/24 (75%)** | ***188/550 (34%)*** | ***1148/3279 (35%)*** | 6.56E−05 | 5.8 (2.3, 14.8) | 6.89E−05 | 5.6 (2.2, 14.1) |
| | HLA-DRB1*11:01[5] | 5/24 (21%) | 103/550 (19%) | 313/3279 (10%) | 0.43 | 1.5 (0.5, 4.4) | 0.037 | 3.4 (1.2, 9.5) |
| | HLA-DQB1 03:01[5] | **11/24 (46%)** | ***240/550 (44%)*** | ***1072/3279 (33%)*** | 0.22 | 1.8 (0.7, 4.5) | 0.025 | 2.8 (1.1 7.1) |

-continued

| c. All subjects analysis[1] | | Subjects with HLA allele of interest[2] | | | sJIA-DHR vs. INCHARGE sJIA | | sJIA-DHR vs. INCHARGE controls | |
|---|---|---|---|---|---|---|---|---|
| | Allele | sJIA-ID)/DHR | INCHARGE, JIA | INCHARGE controls | p-value | OR (95% CI) | p-value | OR (95% CI) |
| Any sJIA-DHR[6] vs. All GWAS Subjects[7] | HLA-DRB1.15:01[3] | **31/45 (69%)** | ***168/773 (22%)*** | ***1649/6812 (24%)*** | 6.91E−11 | so (so 20.2) | 3.13E−10 | 6.9 (3 7, 13) |
| | HLA-DRB1*15:XX[4] | 34/45 (76%) | 182/773 (24%) | 1656/6812 (24%) | 2.31E−13 | 10.8 (5.4, 21.8) | 1.89E+42 | 9.3 (4.7, 18.5) |
| | HLA-DQB1*06:02 | **29/45 (64%)** | ***171/773 (22%)*** | ***1617/6812 (24%)*** | 4.46E−09 | 6.4 (3.4, 12.0) | 8.15E−09 | 5.8 (3.2, 10.7) |
| | HLA-DQB1 06:XX | 34/45 (76%) | 296/773 (38%) | 2831/6812 (42%) | 7.84E−07 | 5.0 (2.5, 10.0) | 3.86E−06 | 4.3 (2.2, 8.6) |
| | HLA-DQA1 01:02 | **35/44 (80%)** | ***265/773 (34%)*** | ***1649/6812 (24%)*** | 2.21E−09 | 7.5 (3.5, 15.7) | 7.08E−10 | 7.5 (3.6, 15.7) |
| | HLA-DRB1*11:01[5] | 10/45 (22%) | 160/773 (21%) | 649/6812 (10%) | 0.808 | 1.1 (0.5, 2.3) | 0.012 | 2.7 (1.3, 5.5) |
| | HLA-DQB1*03:01[5] | **11/45 (24%)** | ***341/773 (44%)*** | ***2289/6812 (34%)*** | 0.007 | 0.4 (0.2, 0.8) | 0.183 | 0.6 (0.3, 1.3) |

OR, odds ratio;
95% Cl, 95% confidence interval;
p-value, p-value by logistic regression;
PCA, principal component analysis;
GWAS, genome wide association study;
INCHARGE, International Childhood Arthritis Genetics Consortium. The GWAS subjects included INCHARGE-SJIA and INCHARGE healthy controls, analyzed separately, as indicated;
[1]The combined INCHARGE cases and controls are referred to as GWAS subjects;
[2]Values expressed as n (%);
[3]HLA-DRB1*15:01 allele was not associated with sJIA in INCHARGE HLA association study (p = 0.59, OR 0.94 [95CI 0.77, 1.2]; unpublished data (MJO) associated with reference[15];
[4]Cases and controls compared for DRB1* 15:01 + 15:03 + 15:06;
[5]Allele was associated with sJIA in INCHARGE HLA association study[15];
[6]sJIA with DHR with or without DLD;
[7]All GWAS refers to all ancestries; Association of HLA alleles additional sJIA-DHR subjects and control subjects can be found online, which is incorporated by reference herein in their entirety and for all purposes.

Example 4: Severe Delayed Hypersensitivity Reactions Associated with IL-1 and IL-6 Inhibitors Link to Common HLA-DRB1*15 Alleles Adverse drug related reactions are one of the leading causes of morbidity and mortality worldwide. Among these reactions, severe, potentially fatal delayed hypersensitivity reactions (DHR) are underrecognized due to their complexity and variable presentation. Particularly during treatment of inflammatory illnesses, DHR may be misinterpreted as disease flares. The most serious types of DHR classify as severe cutaneous adverse reactions (SCAR), including drug reaction with eosinophilia and systemic symptoms (DRESS). Typical features of DRESS-type DHR are latency (days to months) after drug initiation, fever, extensive rash, hematologic manifestations (eosinophilia and atypical lymphocytosis), involvement of various deep organs, and often an extended time to recovery, even after the offending drug is stopped. Recognition of this serious drug reaction during complex illness is both imperative and challenging.

Increasingly, pharmacogenetic data link drug-specific reaction risk with particular human leukocyte antigen (HLA) class I and/or class II alleles. HLA associations with severe drug related reactions have proven to be substantially stronger with much higher odds ratios and more complete penetrance than most of the well-known HLA allelic disease associations in autoimmune disorders. In addition to providing clues to pathogenesis, the finding of an HLA/DHR association allows preventative HLA screening pre-prescription. Some well-characterized HLA associations are specific to alleles found primarily in particular populations; others have been linked to relatively common alleles with a wide global distribution. The cost/benefit ratio of HLA screening to prevent a serious drug reaction in at-risk individuals improves as the population frequency of the HLA risk allele increases.

HLA molecules function to present peptides to T cells through binding to T cell surface receptors for antigen. In some severe reactions, the offending drugs have been shown to interact directly with HLA molecules, which in turn stimulate T cell responses; the drug interaction also can alter the repertoire of peptides bound to HLA. Thus, HLA associations with severe DHR implicate T cells as immune effectors. This implication is corroborated by evidence from biopsies of DHR-associated skin rashes, which show infiltration of activated T cells.

Systemic juvenile idiopathic arthritis (sJIA) is a chronic inflammatory disease of childhood with unknown etiology; parenchymal lung disease is not a typical feature. DRESS was observed among a small group of sJIA patients who developed an unusual, non-infectious parenchymal diffuse lung disease (DLD) during treatment with inhibitors of IL-1 (anakinra, canakinumab, rilonacept) or of IL-6 (tocilizumab). It was hypothesized that DRESS reactions, with and without DLD, were underrecognized in sJIA and its adult counterpart, adult onset Still's disease (AOSD), which are currently considered a single disease, Still's disease, based on clinical and immunologic studies. Clinical features of these drug related reactions were characterized in Still's patients and to assess HLA alleles as candidate inherited risk factors for DRESS in association with these drugs. It was also hypothesized that an HLA-associated risk of delayed drug reaction might extend to other disease contexts.

Methods

Subjects

The Still's disease continuum includes systemic juvenile idiopathic arthritis (sJIA) patients and AOSD patients. Still's disease patients with probable drug reaction associated with anakinra, canakinumab, rilonacept and/or tocilizumab (cases) or with possible drug-tolerance after exposure to the same drugs (controls) were collected from 37 centers (US, Canada, Australia) through web-based and meeting-based solicitation. Additional Still's controls from the International Childhood Arthritis Genetics (INCHARGE) Consortium sJIA collection, the largest available sJIA cohort, and the ancestry-matched, INCHARGE healthy control population were used as sources of genetic data. A small (n=19) cohort of Kawasaki disease (KD) patients in a brief phase I/IIa trial of anakinra (NCT-02179853 FIGS. 6A and 6B 1) also provided cases and controls. In sum, 6 major groups of subjects were used.

Verification of Cases (Drug-Reactive) and Controls (Drug-Tolerant)

Clinical information required for case/control verification of the Still's disease subjects was collected by privacy-protected electronic database or by direct communication with the physician case reporter, under approved IRB protocols (see supplementary information). Still's subjects were verified as cases (n=66, 65 DRESS plus 1 Still's with suspected delayed anakinra reaction) or controls (drug-tolerant; n=65; hereafter called Still's controls), using a validated scoring system, the registry for severe cutaneous adverse reactions (RegiSCAR) for DRESS. The RegiSCAR system was validated in the setting of inflammatory diseases and uses clinical parameters allowing differentiation from active Still's disease. Classification of suspected anakinra reaction (sAR) in Still's (n=1 subject) required >2 occurrences of unexplained eosinophilia (AEC≥500) during treatment. Classification as drug-tolerant (Still's controls) required inhibitor treatment duration of >1 year, RegiSCAR score of <4, and discontinuation of steroids or ≥6 wks dosed at <0.2 mg/kg/day of prednisone equivalent; these criteria excluded those with long latency to DRESS or on sufficient steroids to blunt the reaction.

Data for full RegiSCAR scoring were unavailable for KD subjects. Classification of KD subjects as KD-sAR required eosinophilia ≥50% over pre-treatment, study baseline value. Presumed drug-tolerance in KD was defined as absence of eosinophilia during anakinra exposure (9-46 days). Still's and KD subjects were verified as case or control by a board-certified allergist (VS) prior to HLA determination.

Clinical and Demographic Data Collection

In addition to information for case/control verification, other clinical and demographic (sex, self-identified race) information on the 131 Still's disease subjects was collected. Laboratory data collected during treatment included eosinophil count, aspartate aminotransferase (AST) and alanine aminotransferase (ALT). Eosinophilia was defined as absolute number or percent of white blood cell count above the laboratory's upper limit of normal without other cause, e.g., allergic rhinoconjunctivitis in the absence of steroid treatment. AST/ALT elevation was defined as >2× the upper limit of normal more than once without infection or other non-DRESS cause, including macrophage activation syndrome (MAS). MAS was determined by the case reporter using Ravelli classification criteria.

HLA Genotyping Determination

Genomic DNA was extracted from blood or tissue, and HLA genotyping was performed by one of several methods. For those with limited DNA sample or clinically typed cases, HLA genotyping was limited to Class II [23% (15/64) of Still's-DRESS cases].

Statistical Analyses, Including HLA Association

As this is a case/control study, odds ratios (OR) was, their 95% confidence intervals and corresponding p-values to summarize the association of various clinical and genetic factors of interest with DRESS.

Six major groups of subjects were studied:

1. Still's DRESS cases: Still's disease patients with DRESS (n=66)
2. Still's controls: Still's disease patients without DRESS [drug-tolerant] (n=65)
3. INCHARGE childhood-onset Still's (sJIA) [European ancestry]: Still's disease patients with drug exposure unknown (n=550)
4. INCHARGE healthy controls [European ancestry]: Healthy subjects (n=3279)
5. KD-sAR cases: KD patients with suspected anakinra reaction [sAR] (n=4)
6. KD controls: KD patients without sAR (n=15)

Groups 3 and 4 (INCHARGE Still's controls and healthy controls) were constructed to rigorously ancestry-match a subset of Still's-DRESS cases with European ancestry (White) for unbiased HLA analysis. To this end, two rounds of principal component analysis (PCA) were performed. These used 24 Still's-DRESS cases with whole exome sequence (WES) data, INCHARGE European Still's cases (n=773) and European healthy controls (n=6612). Genomic control inflation factors ($\lambda_{GC}$) were determined to assess robustness of matching.

Analysis of Drug Exposure, Demographic and Clinical Features:

The frequency of exposure to individual inhibitors or any IL-1 inhibitor between Still's-DRESS cases and Still's controls (group 1 vs group 2) using Fisher's exact test was compared. The demographic and clinical characteristics between Still's-DRESS cases and Still's controls (group 1 vs group 2) was compared, using Fisher's exact test. The age of disease onset (<2.5, 2.5-10, 10-16, >16) was compared between Still's-DRESS cases and Still's controls (group 1 vs group 2) using proportional odds regression. These four analyses used the entire Still's case/control collection, excluding 1 or 2 subjects in some analyses of clinical features, due to missing data. In a sensitivity analysis, clinical characteristics were compared (eosinophilia, elevated LFTs and MAS) in the subgroups of Still's-DRESS cases and Still's controls with Still's onset age <16 years (subgroups of group 1 vs group 2) using Fisher's exact test.

HLA Association Analysis:

The analysis of HLA allele association with DRESS in association with the IL-1/IL-6 inhibitors was restricted to subjects who were genotyped for HLA (subsets within groups 1 and 2, as shown in FIG. 1, and the INCHARGE collection). HLA allele frequencies were compared between Still's-DRESS cases with European ancestry and INCHARGE Still's controls (European ancestry patients in group 1 vs group 3) or between Still's-DRESS cases with European ancestry and INCHARGE healthy controls (European ancestry patients in group 1 vs group 4). Specifically, classical class I and class II HLA alleles were analyzed by logistic regression with sex as a covariate. This multi-allelic HLA association analysis was repeated, comparing self-identified White Still's-DRESS cases and INCHARGE Still's controls (self-identified White patients in group 1 vs group 3) and comparing self-identified White Still's-DRESS cases and INCHARGE healthy controls (self-identified White patients in group 1 vs group 4). Bonferroni corrected P value significance threshold, adjusted for multiple comparisons (254 imputed HLA alleles tested), was $P<2.0\times10^{-4}$. The identified risk allele (DRB1*15:01) was also tested for association with risk of DRESS in association with individual inhibitors in self-identified White Still's-DRESS cases versus INCHARGE Still's controls (self-identified White patients in group 1 vs group 3) by logistic regression with sex as a covariate. The frequency of DRB1*15:01 was compared in self-identified White, Still's-DRESS cases and self-identified White Still's controls by Fisher's exact test (self-identified White patients in group 1 vs group 2). In a sensitivity analysis, the latter comparison was repeated using only subjects with sJIA onset age <16 years.

HLA-DRB1*11:01 frequencies were compared between Still's-DRESS cases with European ancestry and INCHARGE Still's controls (European ancestry patients in group 1 vs group 3), between Still's-DRESS cases with European ancestry and INCHARGE healthy controls (European ancestry patients in group 1 vs group 4), between Still's-DRESS cases self-reported as White and INCHARGE Still's controls (self-identified White patients in group 1 vs group 3) and between Still's-DRESS cases self-reported as White and INCHARGE healthy controls (self-identified White patients in group 1 vs group 4). All analyses used logistic regression, adjusting for sex and the Bonferroni corrected P value significance threshold.

We did not have enough non-White subjects for within ancestry comparisons. Therefore, we reported the allele frequencies in these comparisons without formal statistical analyses (e.g., KD-sAR cases vs KD controls and pooled Still's-DRESS+KD-sAR cases vs pooled Still's+KD-sAR controls). Also note that the observed proportion of Still's-DRESS cases in Still's disease subjects or the proportion of DLD cases within Still's-DRESS cases cannot be interpreted as estimates of the prevalence rates due to the case/control study design.

Figure 6A:
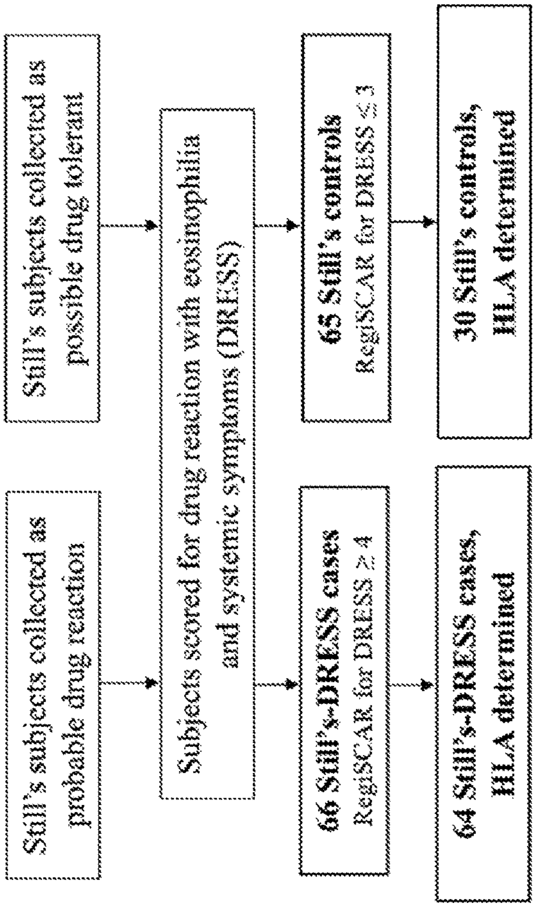
FIGS. 6A and 6B are images depicting the study design. Clinical information was collected on Still's disease subjects with and without clinical suspicion of drug reaction to inhibitors of IL-1 or IL-6 (FIG. 6A). Classification of Still's patients was verified by RegiSCAR scoring for DRESS.
Figure 6B:
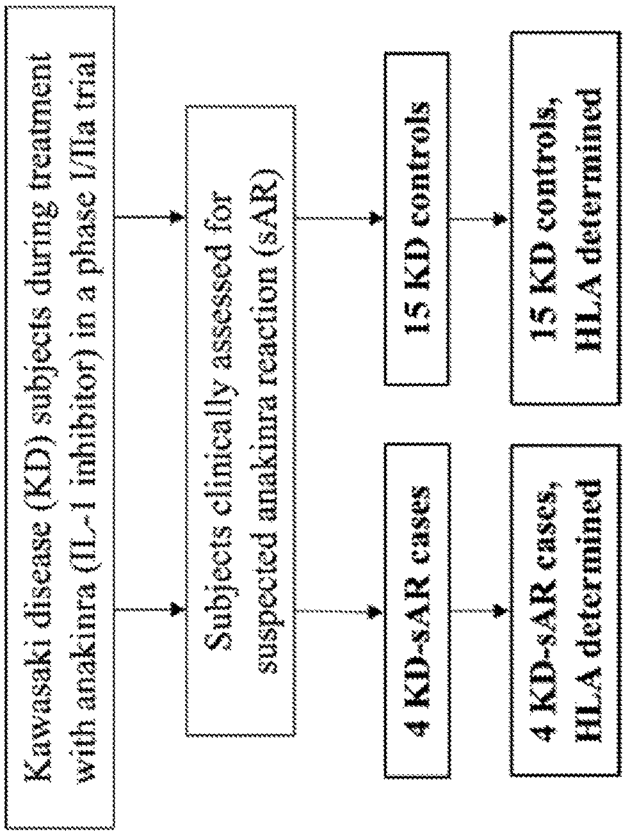

DRESS, Often Unrecognized, Occurred in a Subset of Still's Disease Patients Treated with IL-1 or IL-6 Inhibitors Cases of Still's disease subjects were collected with probable delayed hypersensitivity related to IL-1 inhibitors (anakinra, canakinumab, rilonacept) or an IL-6 inhibitor (tocilizumab) and Still's disease controls with probable drug tolerance. Classification of 66 subjects was confirmed as drug-reactive and 65 subjects as drug-tolerant, using specified criteria, including RegiSCAR/DRESS scoring (FIGS. 6A and 6B).

Almost all (65/66) drug-reactive cases were classified as DRESS; the single exception was classified as suspected anakinra reaction (sAR). The majority (89%) of DRESS patients classified as definite DRESS (FIG. 7); 7 subjects classified a probable DRESS and were included as cases per standard application of RegiSCAR/DRESS. A DRESS reaction was observed in association with anakinra, canakinumab and tocilizumab used alone, indicating that each is capable of triggering DRESS. 26/66 drug-reactive subjects reacted to multiple inhibitors. The frequency of drug reaction per exposed subject was not significantly enriched for IL-1 inhibitors compared to tocilizumab (anti-IL-6) or for a particular IL-1 inhibitor. For each implicated drug, the frequency of reactions/case was comparable to the frequency of exposures/control. These findings supported comparisons of the pooled Still's-DRESS cases to the pooled Still's controls in subsequent analyses.

The Still's-DRESS group and the Still's control group were similar in having broad ancestral distribution, as expected in Still's disease; they differed modestly in % male subjects. [32% vs 51%]. Clinical features did not vary systematically based on the particular drug exposure and were similar among Still's-DRESS patients across the age spectrum, with the exception of increased frequency of DLD in patients with very young onset Still's disease.

In Still's-DRESS cases, DRESS features appeared during treatment at FDA-approved doses for autoinflammatory diseases. Clinical DRESS differed from features of Still's flare and notably included eosinophilia and non-Still's rash (FIG. 8). Peripheral blood eosinophilia without other cause (e.g., pre-existing atopy) was observed in 57/65 (88%) cases. In >60% of cases, eosinophilia was pronounced despite concurrent steroids. Non-evanescent drug eruptions were observed in 63/66 (95%). In 42/48 (88%) providing detail, rash included facial rash and/or edema, which are typical of DRESS. Skin biopsy reports (12 cases) showed features of drug reaction/DRESS, including interface dermatitis, dyskeratosis and eosinophilia. In 49/65 (75%) Still's-DRESS cases, AST-ALT elevation was noted in the absence of MAS or other explanation. MAS during inhibitor treatment, which can be a manifestation of DRESS, was significantly more common in DRESS cases than in Still's controls ($p=1.9\times10^{-14}$). When MAS occurred during drug treatment, transient eosinophilia typically preceded this by months, consistent with evolution of DRESS-associated features.

The drug related reactions were often unrecognized, as reflected by continuation of inhibitor therapy after DRESS criteria were met. Only 17/66 (27%) Still's patients with DRESS stopped IL-1/IL-6 inhibitors for ≥3 months without re-introduction. In this group, rash, eosinophilia, and AST-ALT elevation resolved in all cases, consistent with resolution of DRESS. In addition, with removal of DRESS as a contributor, inflammation became easier to manage. For example, 10/17 (59%) discontinued steroids and only 2/17 cases required steroids >6 months after drug stop [median follow-up 14 months (IQR: 6, 36)]. By contrast, of 33 subjects who continued inhibitors after scoring as DRESS, 9 died and only 17% of survivors were off steroids, despite median follow-up of 27 months (IQR: 16, 53). Restarting suspended IL-1 inhibitors was associated with fatal MAS (4 of 6 cases) within two months.

Common HLA-DRB1*15 Alleles are Risk Factors for DHR Related to IL-1 and IL-6 Inhibitors To test for an HLA association with inhibitor-triggered DRESS, the subset of the Still's disease subjects (n=94/131) with available HLA data was studied. First, PCA analyses of the 24 Still's-DRESS subjects with WES data, yielded a tight cluster of every subject of White (European) ancestry (n=14) from the Still's-DRESS cohort, together with 550 INCHARGE sJIA subjects and 3279 INCHARGE healthy controls. Genomic control inflation factors (kcc) were 1.01-1.05, demonstrating robust matching. Comparing these groups revealed a striking enrichment for HLA-DRB1*15:01 ($p=2.7\times10^{-7}$; Table 8, which is part of a common European haplotype, HLA-DRB5*01:01~DRB1*15:01~DQA1*01:02~DQB1*06:02.

The strong HLA-DRB1*15:01 association was maintained when all self-identified White Still's-DRESS subjects (n=36) were compared to the European INCHARGE Still's (sJIA) cohort ($p=7.5\times10^{-13}$) (Table 8). An analysis of the 36 White subjects was performed, stratified by treatment group. The anakinra, canakinumab, and rilonacept groups were each enriched for HLA-DRB1*15:01, relative to the European INCHARGE Still's (sJIA) cohort. The tocilizumab group was not adequately powered to identify an association; however, the frequency of HLA-DRB1*15:01 among tocilizumab-reactive subjects (80%) was similar to the frequencies observed in the other groups (83-92%). The confidence intervals overlapped with one another, so the effect sizes are statistically indiscernible). No independent HLA class I association was found.

As the INCHARGE collection does not include data on drug tolerance, HLA frequency was compared in the self-identified White Still's-DRESS group to self-identified White Still's drug-tolerant controls (Table 8). Using HLA-DRB1*15:01 as a haplotype proxy, the comparison (83% vs 0%) showed a highly significant enrichment in the DRESS group ($p=6\times10^{-10}$) with a notable effect size (OR lower bound=16.05).

TABLE 8

HLA class II allele association with hypersensitivity related to IL-1 and IL-6 inhibitors

| HLA allele | Ancestry | Cases Still's-DRESS[2] | Controls Still's controls | Controls INCHARGE sJIA | P value[3] | OR (95% CI) |
|---|---|---|---|---|---|---|
| DRB1*15:01 | European vs European | 13/14 (93%) | | 130/550 (24%) | $2.7\times10^{-7}$ | 40.8 (5.3, 316) |
| | self-ID White vs European | 30/36 (83%) | | 130/550 (24%) | $7.5\times10^{-13}$ | 15.5 (6.3, 38.1) |
| DRB1*15:01[4] | self-ID White | 30/36 (83%) | 0/19 (0%) | | $6.3\times10^{-10}$ | Inf (16.05-Inf) |
| | self-ID non-White | 16/28 (57%) | 0/11 (0%) | | | |
| DRB1*15:XX[4] | | 21/28 (75%) | 2/11 (18%) | | | |
| Kawasaki disease | | KD-sAR | Drug-tolerant KD | | | |
| DRB1*15:01 | All | 2/4 (50%) | 0/15 (0%) | | | |
| DRB1*15:XX | All | 3/4 (75%) | 2/15 (13%)[5] | | | |
| Still's + Kawasaki disease | | Still's-DRESS + KD-sAR | Drug-tolerant Still's + KD | | | |
| DRB1*15:01 | All | 48/68 (71%) | 0/45 (0%) | | | |
| DRB1*15:XX | All | 54/68 (79%) | 4/45 (9%) | | | |
| DQB1*06:02 | All | 47/65 (72%) | 3/45 (7%) | | | |

DRESS, Drug reaction with eosinophilia and systemic symptoms classified per RegiSCAR;
INCHARGE, International Childhood Arthritis Genetics Consortium;
OR (95% CI), Odds ratio and 95% confidence interval;
European: Still's-DRESS cases were ancestry-matched by PCA to the INCHARGE Still's (sJIA) cohort;
self-ID, self-identified;
White, similar to European descent;
Inf, infinite;
KD, Kawasaki disease;
HLA-DRB1*15:XX, all HLA-DRB1*15 alleles

[1]In analyses omitting AOSD patients, similar results were obtained.

[2]Includes one case with suspected anakinra reaction (see methods).

[3]P value, top two rows are by logistic regression from multi-allelic comparison to the INCHARGE cohort; only DRB1*15:01 result is shown. Bonferroni corrected $P < 2.0\times10^{-4}$. P-value in third row is by Fisher's exact test, comparing Still's-DRESS to Still's controls for DRB1*15:01.

[4]Each HLA-DR allele group observed in self-identified White Still's DRESS subjects initially was interrogated for association; only HLA-DRB1*15 alleles showed significant association.

[5]HLA-DRB1*15:02 in two individuals, treated briefly (12d and 28d) with anakinra.

Another 28 subjects with Still's-DRESS and 11 who were Still's controls had self-identified ancestry other than White. Although the sample was insufficient to perform within-group analyses, a similarly striking pattern of HLA association. HLA-DRB1*15:01 was observed in 57% non-White subjects with DRESS and 0% of drug-tolerant controls (Table 8). Other alleles of the DRB1*15 family are more often present in non-White/European populations, and these appear to be associated with DRESS as well. Together, HLA-DRB1*15 alleles (specifically HLA-DRB1*15:01, *15:03, *15:06) were noted in 75% non-White subjects with Still's-DRESS compared to 18% Still's controls (Table 9). Comparing the subset of all Still's DRESS subjects who could be matched for ancestry with Still's controls also showed HLA-DRB1*15:XX enrichment in the DRESS versus drug-tolerant group (82% vs 7%; FIG. 9A-9D). No independent HLA class I association with Still's-DRESS was observed.

When the drug-reactive and drug-tolerant cohorts (all ancestries) were analyzed by drug subgroup, the carrier frequencies of HLA-DRB1*15:XX in drug-reactive cases were enriched in each subgroup and similar between groups. HLA-DRB1*15:XX was comparably enriched in DRESS subjects with and without DLD (82% vs 72%). Clinical features in DRESS subjects with and without the identified HLA risk alleles were similar.

The frequency of the sJIA-associated HLA-DRB1*11:01 allele was examined in the cohort. Unsurprisingly, frequencies of this allele in European and self-identified White Still's-DRESS cases were similar to the European INCHARGE Still's (sJIA) cases (Table 9) and increased compared to INCHARGE healthy controls (Table 9). HLA-DRB1*15:01 was not associated with Still's in the European INCHARGE cohort (Table 9). HLA-DRB1*11:01 frequency did not differ significantly between White Still's-DRESS cases and Still's controls. Overall, the results were consistent with the specificity of the HLA-DRB1*11 association for sJIA (young onset Still's) and of the HLA-DRB1*15 association for DRESS in Still's disease. The effect size (odds ratio) for the HLA-associated, inhibitor-related DRESS risk is substantially higher than for the HLA-associated Still's disease risk.

Lastly, it was found that the key clinical and genetic findings persisted when the AOSD subjects were removed from the analyses, supporting the comparison of aggregate Still's-DRESS cases to Still's disease controls.

Common HLA-DRB1*15 Alleles are Also Likely Risk Factors for Suspected Anakinra Reaction in KD To determine whether HLA-linked delayed drug hypersensitivity required Still's-specific immune dysfunction, a small cohort (n=19) of children with KD were studied in a trial of 2-6 weeks of anakinra treatment. Four had suspected delayed anakinra reaction (sAR). The same striking effect was observed, where 3/4 children with sAR carried HLA-DRB1*15 alleles (HILA-DRB 1*15:01 and *15:03), whereas a different HLA-DRB1*15 allele, HLA-DRB1*15:02, was observed in 2/15 apparently drug-tolerant children with KD (Table 8). Notably, HLA-DRB1*15:01 was not observed in any drug-tolerant subject. No class I association was observed.

High percentages of all DHIR subjects (Still's+KD) carried DRB1*15 alleles across all ancestries (FIGS. 9A-9D). While the HLA-DRB1*15:01~DQA1*01:02'~DQB1*06:02 haplotype is in near-complete linkage disequilibrium (LD) in European populations, analysis across ancestries, in which patterns of LD differ, can help to pinpoint the associated locus. Considering the entire Still's-DRESS+KD-sAR group, HLA-DRB1*15:01 was observed in 71% (46/64 Still's-DRESS subjects and 2/4 with KD-sAR) and was completely absent in drug-tolerant controls (table 1, S1a-b, S7a). In contrast, HLA-DQB1*06:02 was observed in 7% of controls, in the context of different haplotypes (table 1, S1a, S7a), suggesting HLA-DRB1 as the operative locus. It is important to note that HLA-DRB5*01:01, an allele of a secondary HLA-DRB locus, is found on nearly all haplotypes with HLA-DRB1*15. This was not ruled out as an effector or contributor to DHR risk.

DISCUSSION

Strong evidence in Still's disease patients for severe delayed hypersensitivity associated with anakinra, canakinumab, rilonacept (anti-IL-1) and tocilizumab (anti-IL-6) was uncovered. Delayed hypersensitivity reactions occurred with similar frequency after IL-1 or IL-6 inhibition and after any of the IL-1 inhibitors. These reactions met classification criteria for DRESS, a potentially fatal, eosinophilic systemic syndrome. DRESS can lead to organ failure and can stimulate MAS. Indeed, MAS can be the presenting sign of DRESS. MAS frequency in Still's-DRESS cases far exceeded MAS frequency in Still's controls or in published Still's disease series. MAS as part of DRESS in association

TABLE 9

HLA-DRB1*11:01 is Still's-associated in the Still's-DRESS cohort[1]

| HLA allele | Ancestry | Still's-DRESS | Still's controls | INCHARGE Still's (sJIA) | INCHARGE healthy controls | P value | OR (95% CI) |
|---|---|---|---|---|---|---|---|
| DRB1*11:01 | European | 4/14 (29%) | | 103/550 (19%) | | 0.43 | |
| | vs | | 2/19 (10%) | | | 0.36 | |
| | European | | | | 313/3279 (10%) | 0.095 | 3.7 (1.1-11.9)[2] |
| | INCHARGE | | | | | | |
| DRB1*11:01 | Self-ID | 7/35 (20%) | | 103/550 (19%) | | 0.051 | |
| | White vs | | 2/19 (10%) | | | 0.46 | |
| | European | | | | 313/3279 (10%) | 0.01 | 2.3 (1.0-5.2)[2] |
| | INCHARGE | | | | | | |
| DRB1*15:01 | European | | | 130/550 (24%) | 822/3279 (25%) | 0.59 | |

P value, by logistic regression with sex as a covariate for INCHARGE comparisons; OR (95% CI), Odds ratio and 95% confidence interval; sJIA, systemic juvenile idiopathic arthritis; DRESS, Drug reaction with eosinophilia and systemic symptoms classified per RegiSCAR; INCHARGE, International Childhood Arthritis Genetics Consortium; European, Still's-DRESS cases were ancestry-matched by PCA to Still's (sJIA) INCHARGE.

[2]Results are consistent with published data from INCHARGE consortium study of HLA association with sJIA. Drug exposure in INCHARGE sJIA subjects is unknown.

with inhibitors suggests a possible etiologic pathway distinct from that of Still's-associated MAS. In the relatively short-term exposure of KD patients to anakinra, a subset of patients also developed clinical manifestations consistent with drug reaction, arguing that these delayed hypersensitivity reactions can occur in conditions other than Still's disease.

Importantly, a genetic risk factor shared across the delayed reactions to these inhibitors was discovered, analyzed individually or as a group. A very strong association of the HLA-DRB1*15:01 allele and the linked HLA-DRB5*01:01 in White Still's subjects was observed. The numbers of Still's-DRESS cases, Still's controls and INCHARGE Still's (sJIA) controls allowed rigorous analysis of this ancestry group. The effect size was substantially greater than those seen in HLA/disease associations and instead is comparable to those observed in HLA associations with severe drug-related delayed hypersensitivity. Other drug-related HLA associations were initially detected in sample sizes similar to the one reported here and subsequently confirmed. A striking penetrance of the risk allele was detected, as evidenced by its complete absence in drug-tolerant controls and the highly significant p-values reported.

Although the relative scarcity of non-White subjects limited the sample, the findings also suggested that, in addition to HLA-DRB1*15:01, other alleles of the HLA-DRB1*15 family are linked to risk of inhibitor-triggered reaction in these populations. The distribution of subjects with HLA-DRB1*15:XX argues the risk applies across ancestry groups, as found in some other HLA/DHR associations. Carriers of DRB1*15:01, *15:03, *15:06 alleles are common [27% (White), 15% (Hispanic), 27% (Black) and 16% (Asians) in US populations]. The current cohort does not allow analysis of HLA-DRB1*15:02, a high frequency allele in Asian populations. Approximately 20% of the subjects with a drug reaction do not carry the risk alleles. It will be important to determine if other genetic factors confer risk, both in those with and those without the DRB1*15 risk alleles. Investigation of family history of drug reaction may be useful as regards other risk factors.

In Still's disease and KD, the drug related reactions are delayed type and differ from the immediate, anaphylactic reactions to tocilizumab observed in association with DLD in sJIA. Although some Still's subjects experienced both types of drug related reactions, most did not, and carriers of HLA-DRB1*15 alleles were not enriched among those with anaphylaxis to tocilizumab.

The HLA association had some interesting features: it is restricted to HLA class II, and it spans several inhibitors with different chemical structures.

The conditions for which these inhibitors may be used are a large and expanding group. Scattered reports of DRESS or hyper-eosinophilia with rash implicating these drugs in RA, polyarthritis, undifferentiated autoinflammatory disorder, giant cell arteritis and COVID-related cytokine storm were found. HLA typing was not included in these reports and will be important in future investigations. As an n of 1, the continuing case collection includes DRESS in a DRB1*15:01-positive individual with undifferentiated autoimmune disease.

Other than a few case reports, previous studies of IL-1 or IL-6 inhibitors do not mention DRESS. However, it is possible that the reaction was unrecognized. In a recent study of anakinra as first-line therapy for sJIA, 17% of subjects required high dose steroids for clinical deterioration or MAS. The pivotal trial of canakinumab for sJIA had a 19% non-response rate. A study of tocilizumab in RA had a 15% withdrawal rate for adverse events and/or failure to respond. In 24 COVID-19 patients treated with tocilizumab, post-treatment elevation of IL-6 levels identified the 25% who died. Further work is needed to determine if hypersensitivity contributes to the rates of drug failures.

There are several limitations to the study. First, the White Still's control group was small. This limitation was addressed by using the European INCHARGE Still's (sJIA) cohort as a comparator, although the drug tolerance status of these subjects is unknown. Notably, however, unidentified Still's-DRESS cases among these subjects would mean the high odds ratio observed is an underestimate of the true effect size. The number of Still's-DRESS cases with information for robust ancestry loci-matching with the INCHARGE controls was limited. Nonetheless, the highly significant association with HLA-DRB1*15 alleles was replicated in the total Still's-DRESS+sAR group (n=64), with and without self-identified ancestry matching, and in KD-sAR. It seems unlikely that the HLA link is indirect. Other limitations include those inherent to a retrospective observational design, such as missing data. For example, information to determine whether the DRESS subset had a higher frequency of herpes virus reactivation, particularly HHV-6, as reported in DRESS was lacking. The sample had under-representation of non-White subjects, limiting the genetic/HLA analyses. Currently, validation cohorts are being assembled for Still's-DRESS across ancestry groups.

The HLA association reported herein is at least equivalent in effect to the association of HLA-B*57:01 with hypersensitivity related to abacavir treatment with abacavir contraindicated in carriers of this risk allele and in the smaller group of risk-allele negative, drug-reactive patients. Similar to recent reports, onset of drug-related severe delayed reaction was observed as early as three days after first exposure but also after months of treatment.

The frequency of the risk alleles across populations, the strength of the HLA association, and reaction severity, argue for pre-prescription risk analysis. HLA testing is readily available and typically offered at reasonable cost.

CONCLUSIONS

Drug reaction with eosinophilia and systemic symptoms (DRESS), a severe delayed hypersensitivity reaction (DHR), is underrecognized, especially in inflammatory conditions. Secondary hemophagocytic lymphohistiocytosis, indistinguishable from macrophage activation syndrome (MAS), is reported in DRESS, and strong HLA allelic associations are common in severe, drug-related DHR. As shown herein, a subset of Still's patients develop DRESS in association with anakinra, canakinumab, rilonacept or tocilizumab. Moreover, MAS during treatment with inhibitors of IL-1 or IL-6 may be a manifestation of this DRESS reaction. Diffuse lung disease occurs in some Still's patients with this DRESS reaction. Finally, delayed hypersensitivity reactions related to inhibitors of IL-1 and IL-6 exhibited a striking association with a common HLA class II haplotype. The findings argue for consideration of HLA testing for pre-prescription risk assessment. Furthermore, as 20% of subjects with a reaction do not carry the risk alleles and relevance in other conditions is unknown, vigilance for a DRESS-type delayed reaction is recommended during treatment with these inhibitors, and DRESS-type reactions occur among patients treated with IL-1/IL-6 inhibitors and strongly associate with common HLA-DRB1*15 haplotypes. Consideration of pre-prescription HLA typing and vigilance for serious reactions to these drugs are warranted.

What is claimed is:

1. A method of treating a subject receiving, or in need of, an anti-IL-1 or an anti-IL-6 therapy, the method comprising detecting a human leukocyte antigen (HLA)-DRB1*15 allele or HLA-DRB5*01:01 allele in a biological sample of the subject; and for the subject receiving an anti-IL-1 or an anti-IL-6 therapy, performing an action selected from (i) discontinuing the anti-IL-1 or anti-IL-6 therapy, (ii) administering an altered dose of the anti-IL-1 or anti-IL-6 therapy; or (iii) administering the anti-IL-1 or an anti-IL-6 therapy in combination with an additional therapy; or for the subject in need of an anti-IL-1 or an anti-IL-6 therapy, administering an alternative to anti-IL-1 or an anti-IL-6 therapy to the subject, wherein the alternative therapy comprises one or more therapies selected from intravenous gamma globulin (IVIG), a calcineurin inhibitor, a Janus kinase (JAK) inhibitor, a TNF inhibitor, a corticosteroid, a T-cell inhibitor, and an IL-5 inhibitor therapy, wherein the anti-IL-1 or anti-IL-6 therapy is anakinra, canakinumab, rilonacept, tocilizumab, sarilumab, or satralizumab therapy, wherein the subject in need of an anti-IL-1 or anti-IL-6 therapy is a subject having an inflammatory disease selected from systemic juvenile idiopathic arthritis (sJIA), adult onset Still's disease (AOSD), Kawasaki disease (KD), polyarthritis, rheumatoid arthritis, undifferentiated autoinflammatory disorder, giant cell arteritis, and COVID-19 related cytokine storm.

2. The method of claim 1, wherein the HLA-DRB1*15 allele is an HLA-DRB1*15:01 allele, HLA-DRB1*15:03 allele or an HLA-DRB1*15:06 allele.

3. The method of claim 1, wherein the HLA-DRB5*01:01 allele is detected.

4. The method of claim 1, wherein the administering an altered dose of the anti-IL-1 or anti-IL-6 therapy comprises decreasing the dose or decreasing the frequency of administration, optionally wherein the decreased dose is 20% to 80% of the originally administered dose or the decreased frequency of administration is half the original frequency administered.

5. The method of claim 1, wherein the administering an anti-IL-1 or anti-IL-6 therapy in combination with an additional therapy comprises one or more additional therapies selected from methotrexate therapy, corticosteriod therapy, and a disease-modifying antirheumatic drug (DMARD) therapy.

6. The method of claim 1, wherein the calcineurin inhibitor is cyclosporine or tacrolimus.

7. The method of claim 1, wherein the Janus kinase inhibitor is tofacitinib, baricitinib, ruxolitinib, or upadacitinib.

8. The method of claim 1, wherein the TNF inhibitor is adalimumab.

9. The method of claim 1, wherein the T-cell inhibitor is abatacept.

* * * * *